United States Patent
Maras et al.

(10) Patent No.: US 10,335,394 B2
(45) Date of Patent: Jul. 2, 2019

(54) PROCESSES FOR PREPARING DOLUTEGRAVIR AND CABOTEGRAVIR AND ANALOGUES THEREOF

(71) Applicant: Lek Pharmaceuticals d.d., Ljubljana (SI)

(72) Inventors: Nenad Maras, Ljubljana (SI); Lovro Selic, Ljubljana (SI); Anja Cusak, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 15/542,756

(22) PCT Filed: Jan. 15, 2016

(86) PCT No.: PCT/EP2016/050716
§ 371 (c)(1),
(2) Date: Jul. 11, 2017

(87) PCT Pub. No.: WO2016/113372
PCT Pub. Date: Jul. 21, 2016

(65) Prior Publication Data
US 2017/0368040 A1    Dec. 28, 2017

(30) Foreign Application Priority Data
Jan. 16, 2015 (EP) .................... 15151449

(51) Int. Cl.
*C07D 498/14* (2006.01)
*A61K 31/4355* (2006.01)
*A61K 31/421* (2006.01)
*A61K 31/4985* (2006.01)

(52) U.S. Cl.
CPC ........ *A61K 31/4355* (2013.01); *A61K 31/421* (2013.01); *A61K 31/4985* (2013.01); *C07D 498/14* (2013.01)

(58) Field of Classification Search
CPC .................................................. A61K 31/4355
See application file for complete search history.

(56) References Cited

FOREIGN PATENT DOCUMENTS

| EP | 2-602-260 | * | 6/2013 |
| EP | 2602260 A1 | | 12/2013 |
| WO | 2006116764 A1 | | 11/2006 |
| WO | 2010068253 A1 | | 7/2010 |
| WO | 2011119566 A1 | | 9/2011 |

OTHER PUBLICATIONS

International Search Report and Written Opinion for PCT/EP2016/050716, dated Apr. 20, 2016, 15 pages.

* cited by examiner

*Primary Examiner* — Paul V Ward
(74) *Attorney, Agent, or Firm* — Luedeka Neely Group, P.C.

(57) ABSTRACT

The present invention relates to processes for preparing substances with antiviral activity, in particular the integrase inhibitors dolutegravir and cabotegravir and analogues thereof, as well as intermediates useful in the processes.

16 Claims, No Drawings

PROCESSES FOR PREPARING DOLUTEGRAVIR AND CABOTEGRAVIR AND ANALOGUES THEREOF

This application is a Section 371 national entry of PCT application PCT/EP2016/050716, Jan. 15, 2016. This application also claims the benefit of the earlier filing date of European patent application 15151449.4, filed Jan. 16, 2015.

FIELD OF THE INVENTION

The present invention relates to processes for preparing substances with antiviral activity, in particular the integrase inhibitors dolutegravir and cabotegravir and analogues thereof.

BACKGROUND OF THE INVENTION (4R,12aS)—N-[(2,4-Difluorophenyl)methyl]-3,4,6,8,12,12a-hexahydro-7-hydroxy-4-methyl-6,8-dioxo-2H-pyrido[1',2':4,5]pyrazino[2,1-b][1,3]oxazine-9-carboxamide (Formula A):

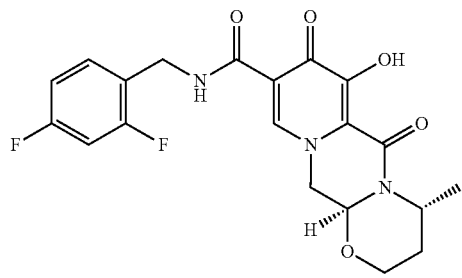

Formula A known by the INN name dolutegravir, is a new efficient antiviral agent from the group of HIV integrase inhibitors which is used in combination with some other antiviral agents for treatment of HIV infections, such as AIDS. The compound, which belongs to condensed polycyclic pyridines and was first disclosed in WO2006/116764, is marketed.

Another compound disclosed in WO2006/116764 is (3S,11aR)—N-[(2,4-difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide (Formula C):

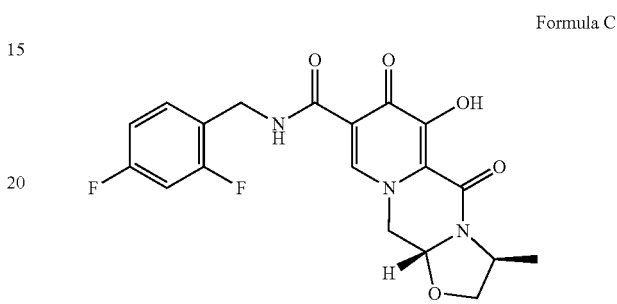

Formula C known by the INN name cabotegravir.

The complex structures of dolutegravir and cabotegravir present a synthetic challenge. The first description of the synthesis in WO2006/116764 shows a 16-steps synthesis (see Scheme A), which is industrially impractical due to its length and low overall yield.

Scheme A

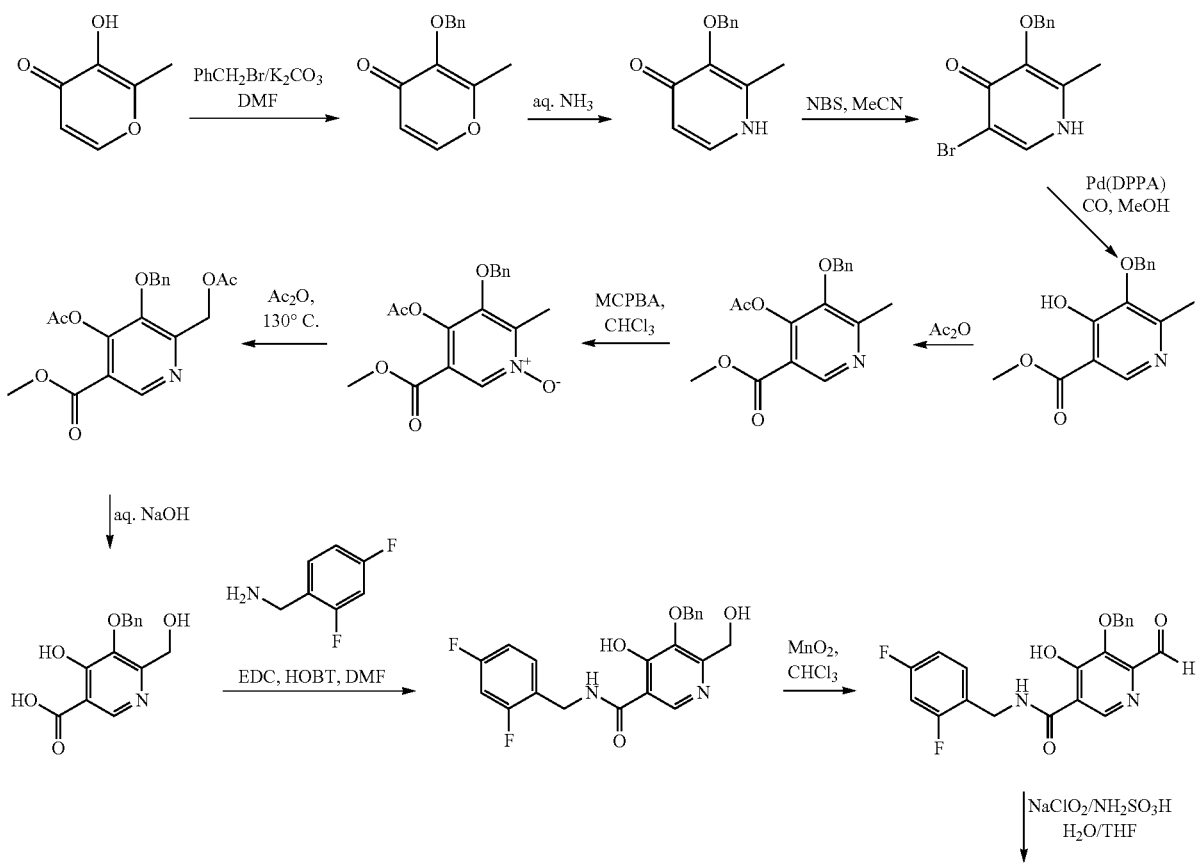

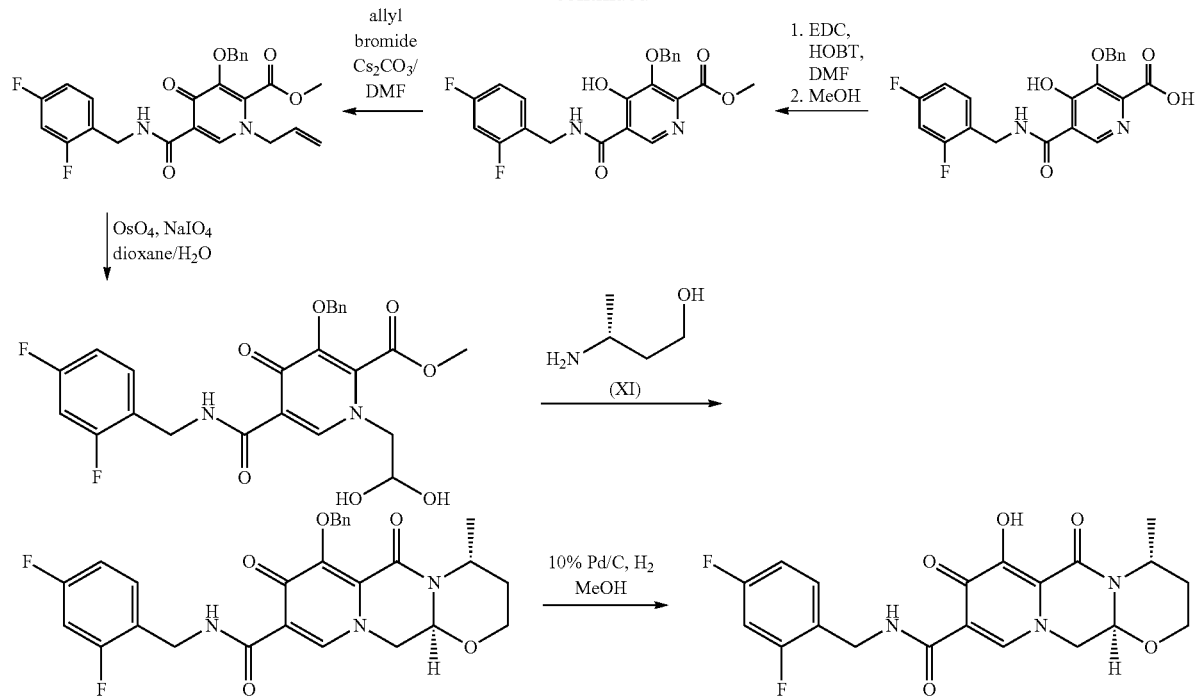

WO 2010/068253 and WO 2006/116764 describe an alternative synthesis. The 11-step synthesis, shown in Scheme B1 and Scheme B2, is based on bromination of the 9-position for further introduction of the carboxylic group. The synthesis relies on the use of expensive palladium catalysts and toxic selenium compounds. Furthermore, some variations of these approaches involve pyrone intermediates in several steps. In some cases pyrones are liquids which can complicate purification, while further reactions form complex mixtures.

Scheme B1

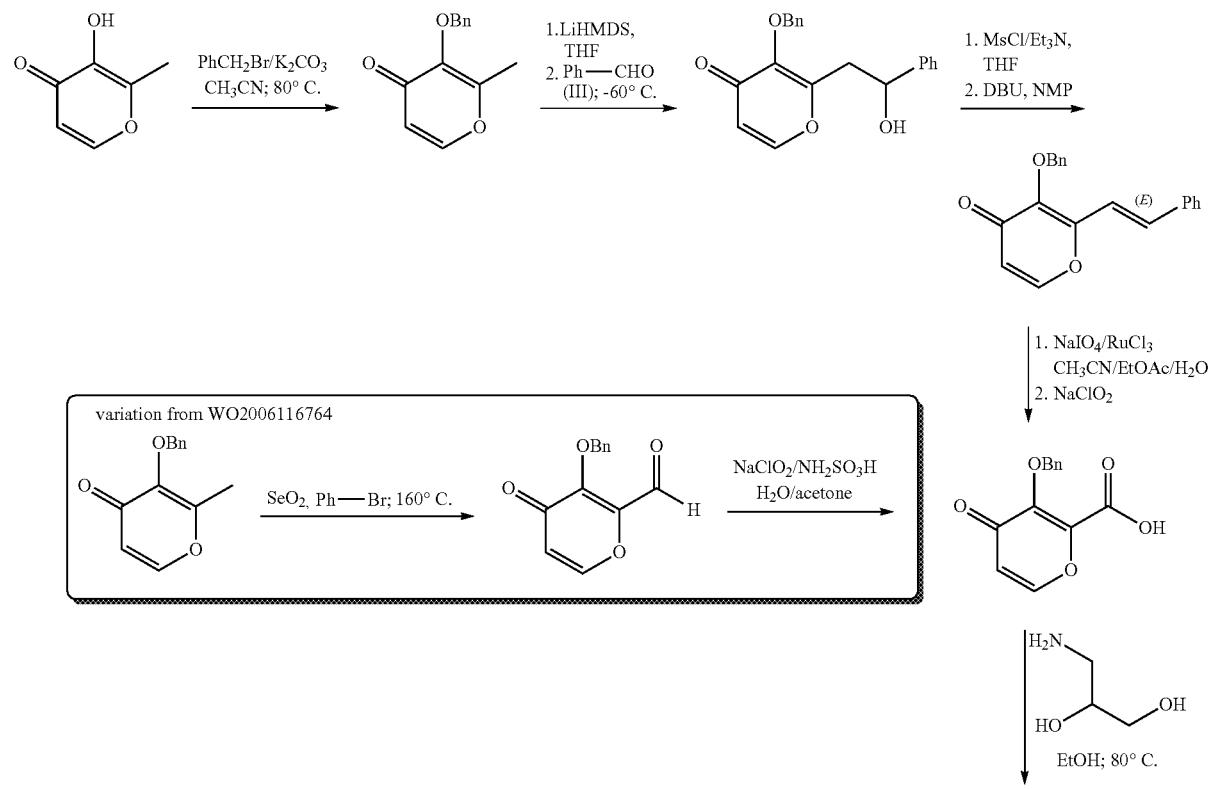

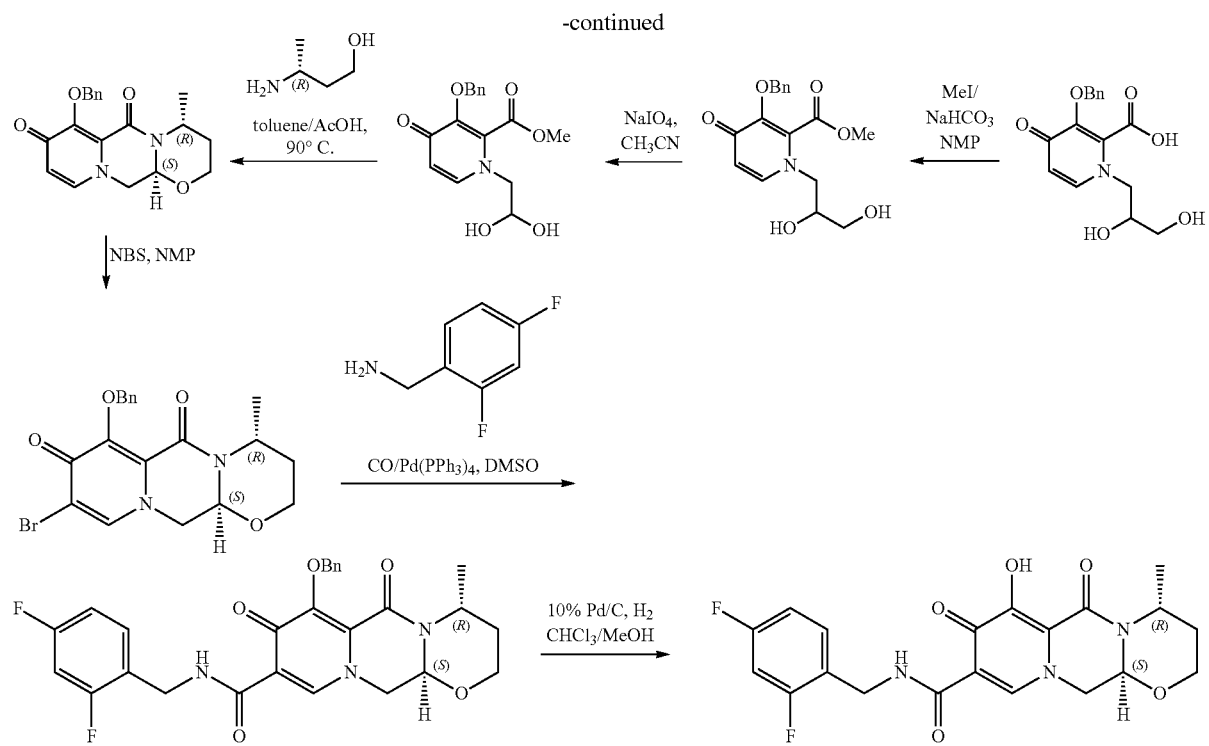

Scheme B2
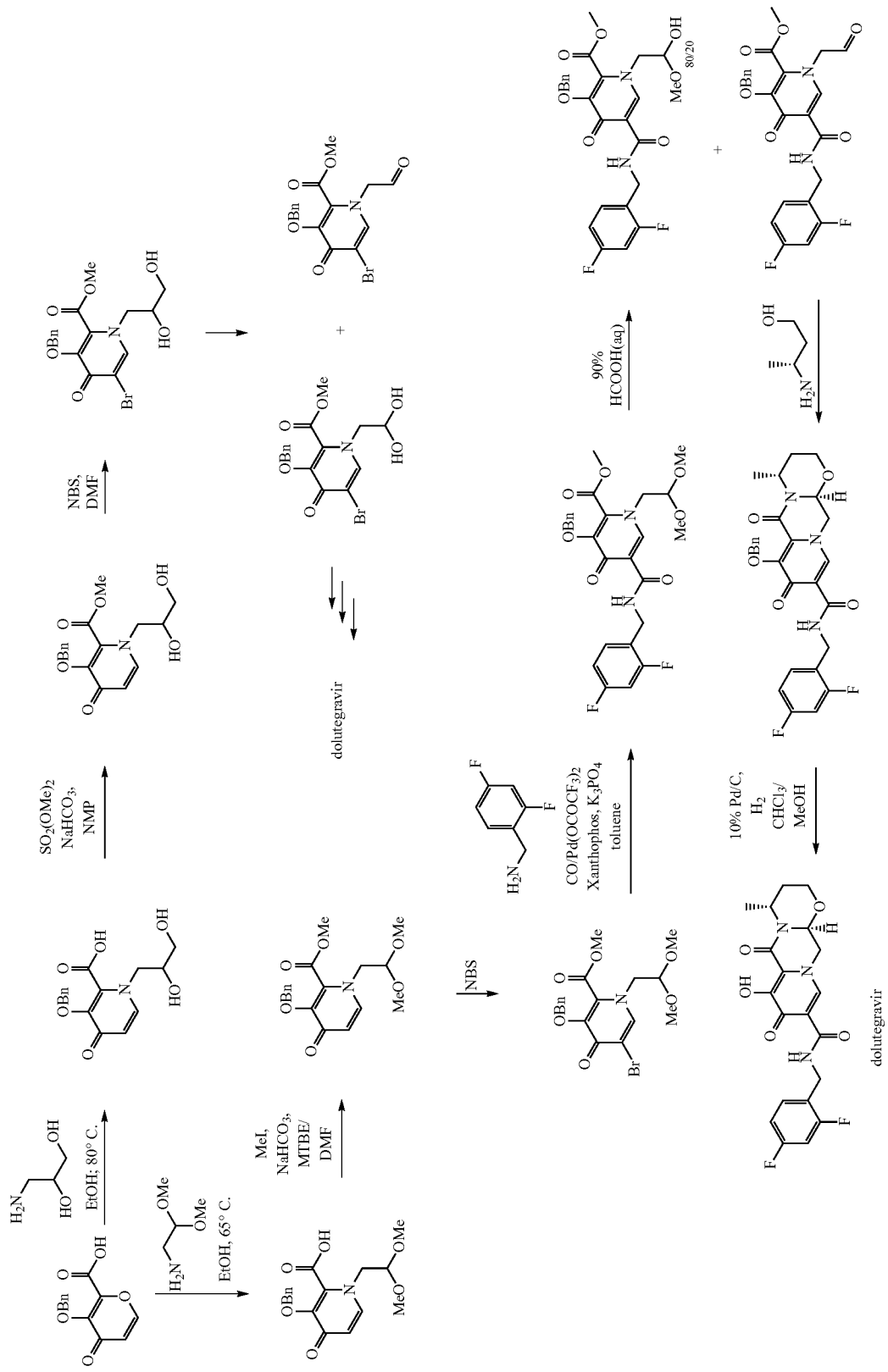

In further alternative syntheses, acetoacetates were used as starting materials. Such an approach is challenging in terms of introducing the hydroxy group in the 7-position. The variation in Scheme C1, described in WO2012/018065, starts from 4-benzyloxyacetoacetate. The procedure requires 9 steps, but use expensive reagents like palladium catalysts. Moreover, there is described a possibility of formation a co-crystal between an intermediate and hydroquinone, wherein however the additional step may diminish yields and make the process longer and time consuming.

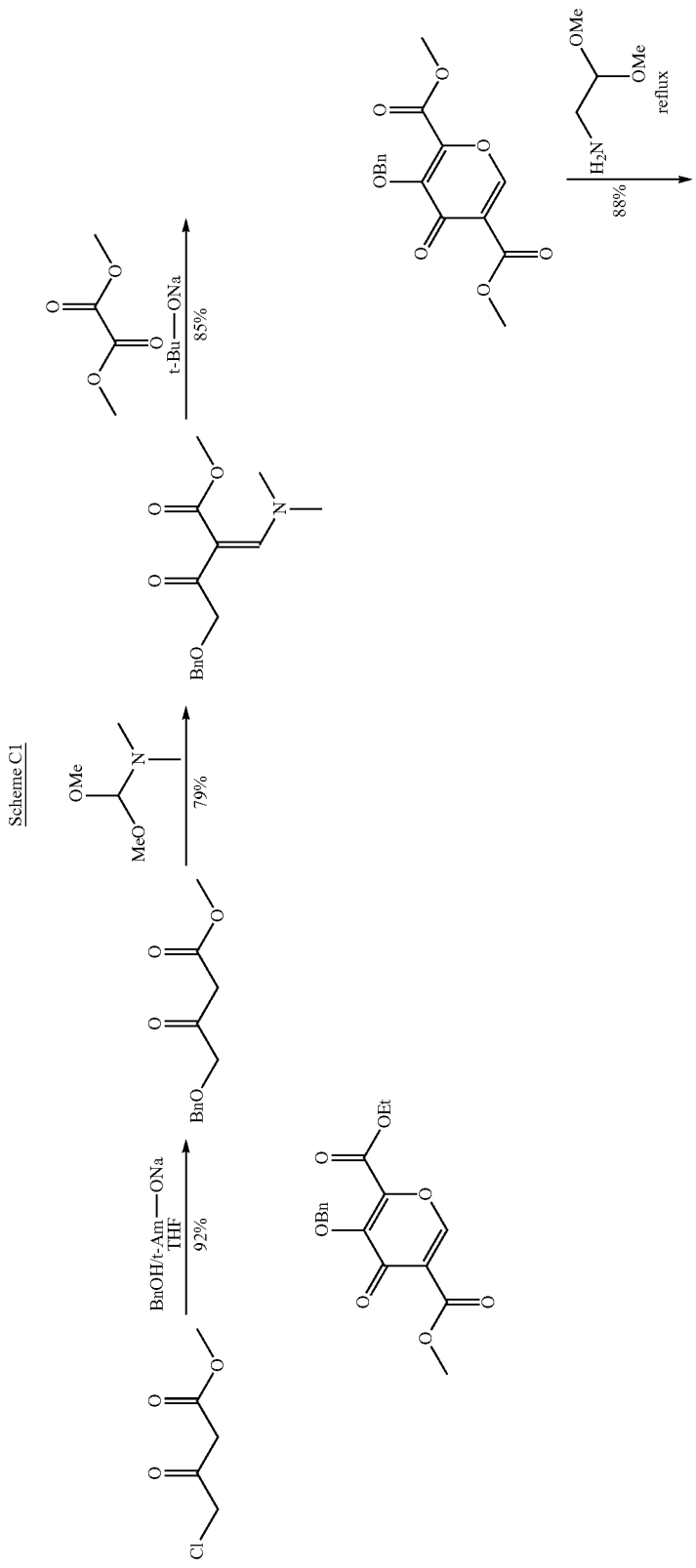

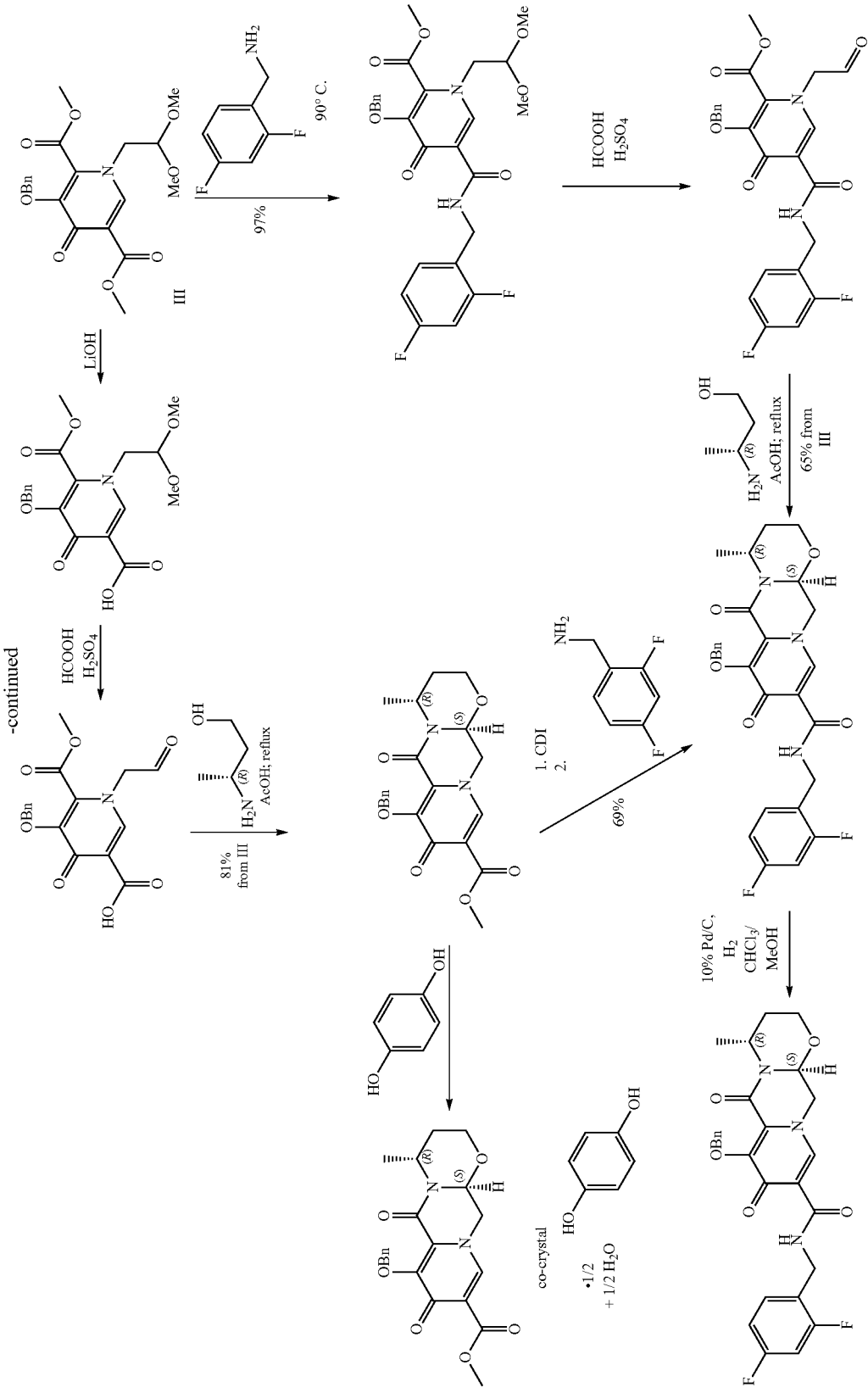

The variation in Scheme C2, described in WO2012/018065, starts from 4-chloroacetoacetate. The process is not optimal because of problems in steps which include pyrones and because of problems with conversion of 7-chloro to 7-hydroxy group which includes a disadvantageous use of silanolates with low yield (25%).

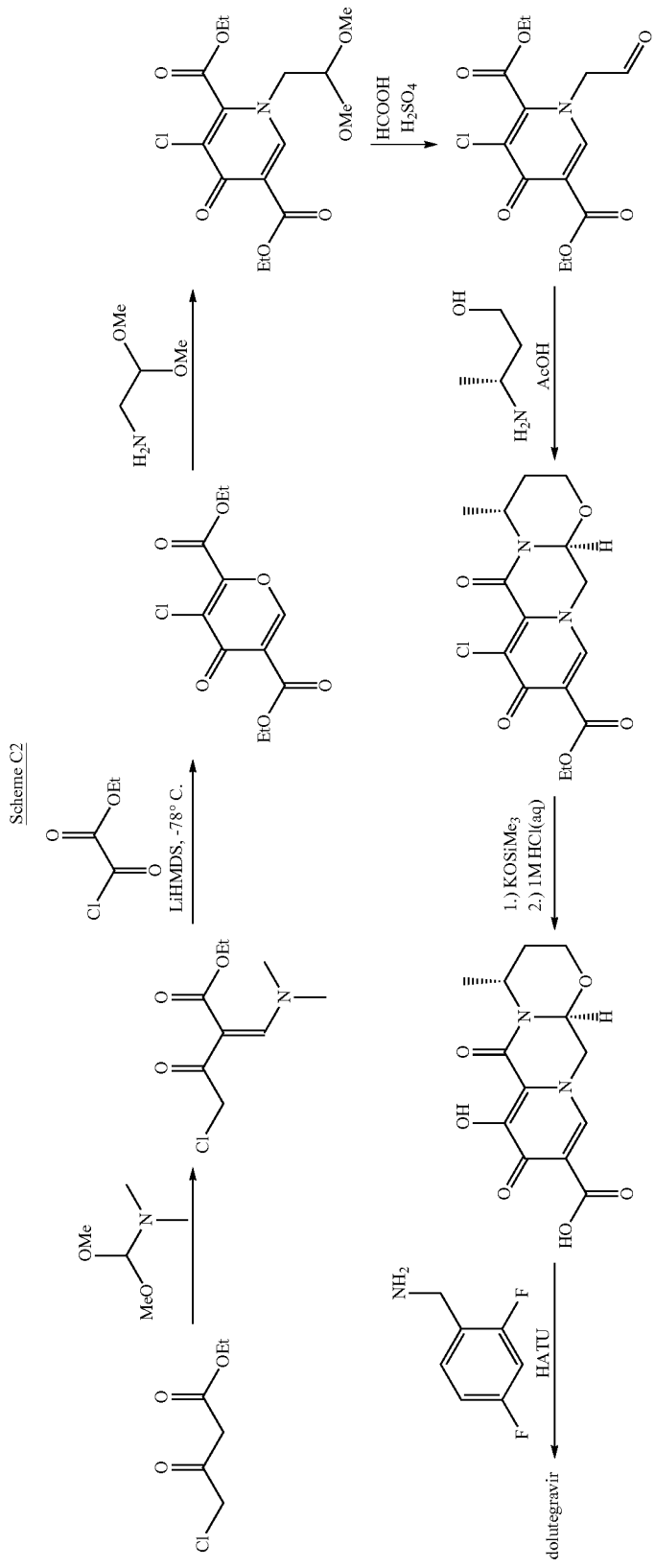
Scheme C2

The variation in Scheme C3, described in WO2011/119566, starts from unsubstituted acetoacetate. For the introduction of the 7-hydroxy group, bromination is used and substitution of bromo with hydroxy is performed by a use of silanolates. The substitution of the bromine is achieved in a 43% yield.

Scheme C3
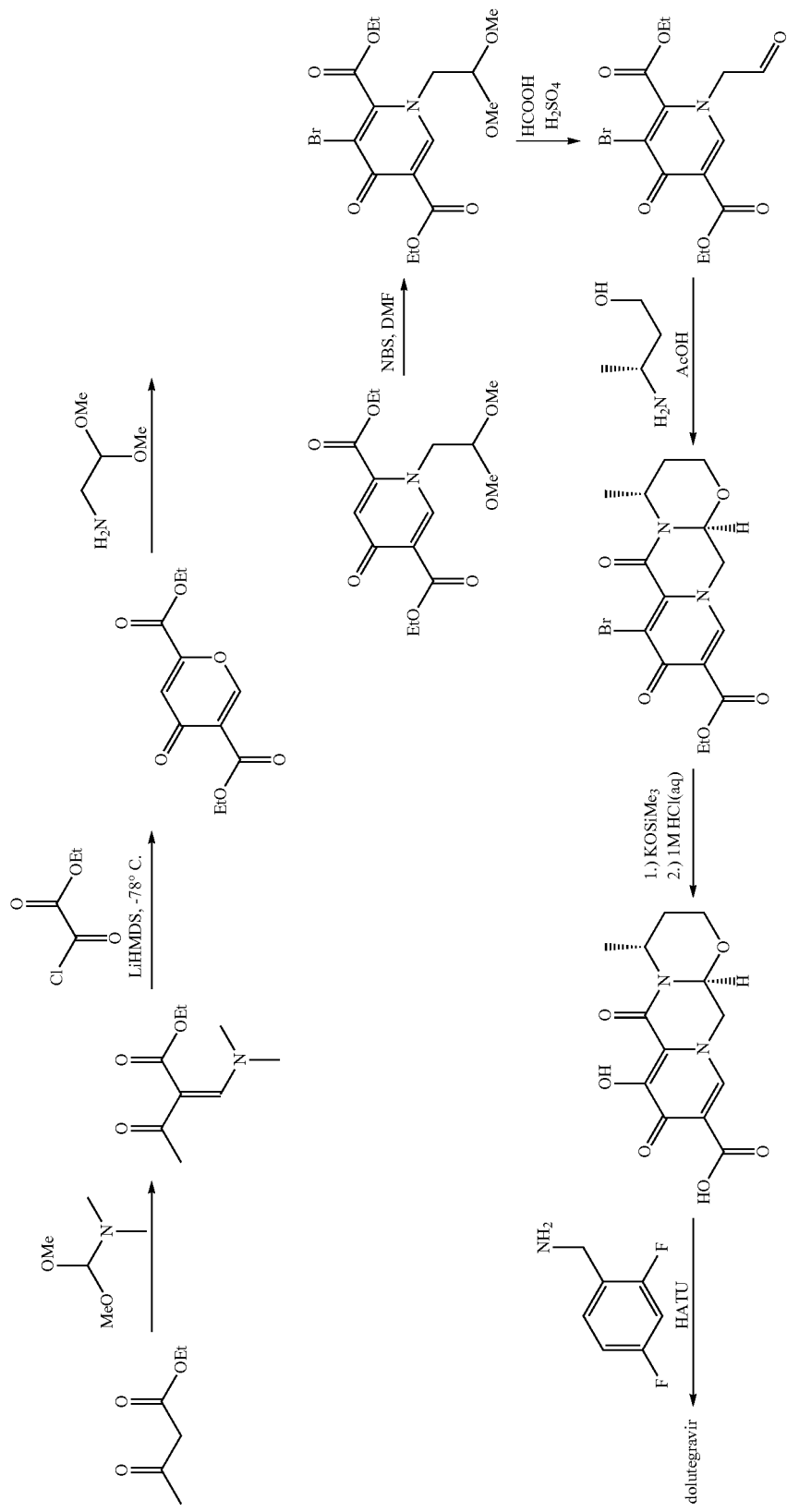

The variation in Scheme C4, described in WO2011/119566, starts from 4-methoxyacetoacetate aiming at preparing dolutegravir or cabotegravir. The process uses lithium bases to affect a difficult to control selective monohydrolysis of a diester.

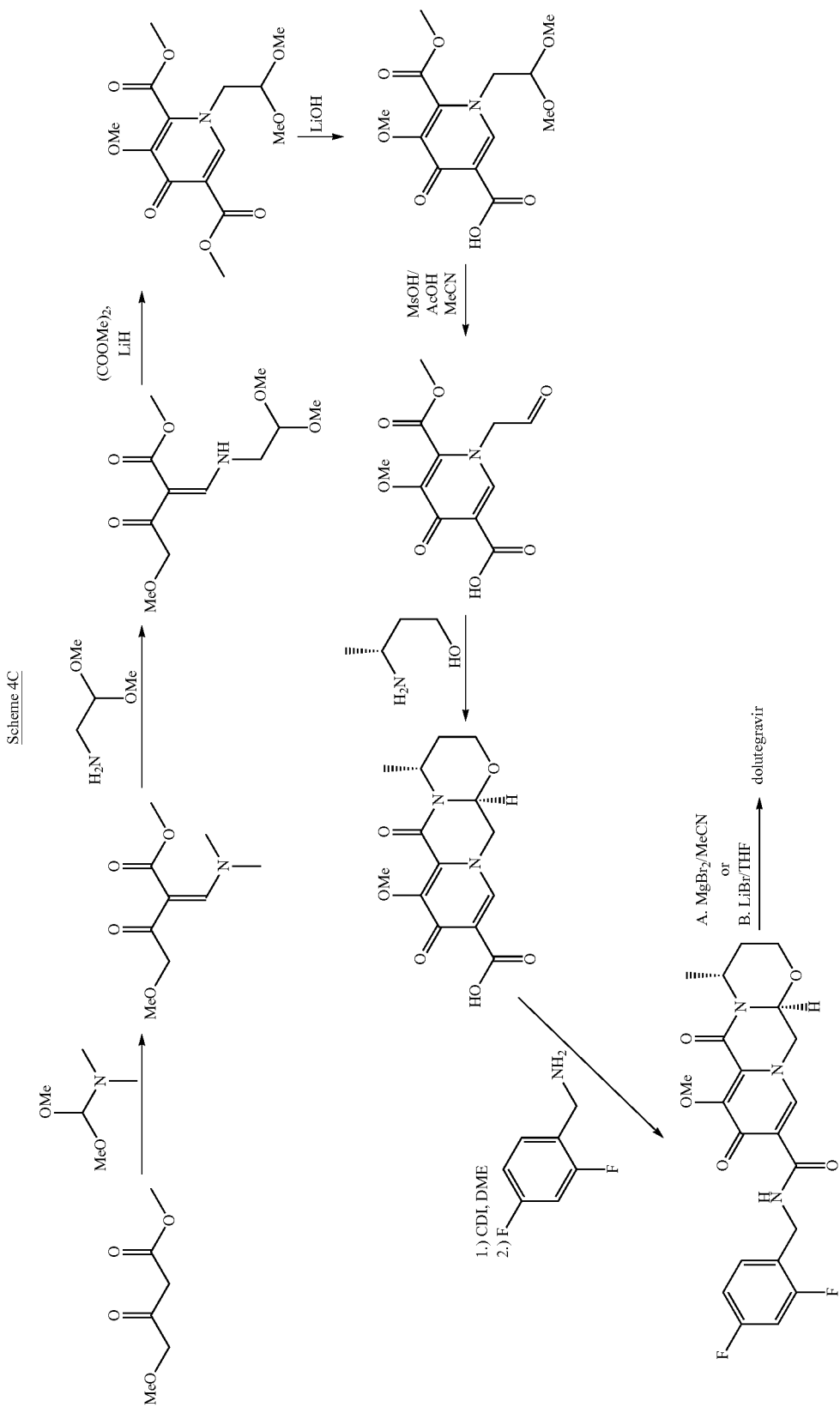
Scheme 4C

The object of the present invention is to provide short, simple, cost-effective, environmentally friendly and industrially suitable processes for beneficially providing dolutegravir and analogues thereof and cabotegravir and analogues thereof, in particular dolutegravir.

SUMMARY OF THE INVENTION

The object is solved by the methods according to claims 1, 9, 12, 13 and 14, and the compounds according to claim 10, while preferred embodiments are set forth in dependent claims and will be further described below.

The present invention in particular provides various aspects, advantageous features and preferred embodiments as summarized in the following items, which respectively alone or in combination particularly contribute to solving the object of the invention and eventually provide additional advantages:

(1) A process for preparing a compound of formula (I) or a salt thereof

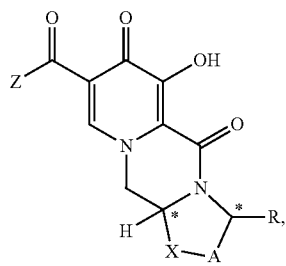

(I)

wherein
A represents $CH_2$ or $CH_2$—$CH_2$,
R represents H, $C_1$-$C_4$ alkyl or unsubstituted or substituted phenyl,
X represents O, S, or N—$R^5$, wherein $R^5$ is H or $C_1$-$C_4$ alkyl,
Z represents hydroxy, $C_1$-$C_4$ alkoxy, phenoxy, benzoxy, —NH—Ar or —NH—$CH_2$—Ar, wherein
Ar represents unsubstituted or substituted phenyl, and
\* represents a chirality center, which is of (R) or (S) configuration,
the process comprising the steps of
(a) providing a compound of formula (II) or a salt thereof,

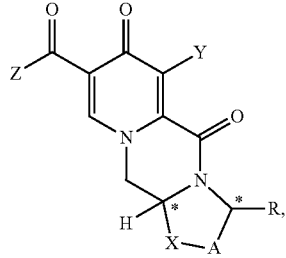

(II)

wherein A, R, X, Z, and \* have the same meaning as above and
Y represents Cl or O—$R_a$,
wherein $R_a$ represents $C_1$-$C_4$ alkyl or benzyl, preferably $C_1$-$C_4$ alkyl, more preferably ethyl or methyl, most preferably methyl,
and
(b) carrying out a chemical transformation to obtain the compound of formula (I) and/or a salt thereof, wherein the transformation is carried out in the presence of a hydroxide.

(2) The process according to item (1), wherein the hydroxide is a metal hydroxide, preferably is an alkali metal hydroxide, more preferably is sodium hydroxide.

(3) The process according to item (1) or item (2), wherein the hydroxide in step b) is added in a solid state.

(4) The process according to any one of preceding items, wherein the hydroxide is used in a 1.2 to 10 molar excess, preferably in a 3 to 7 molar excess, most preferably in a 5 molar excess, compared to the compound of formula (II).

(5) The process according to any one of preceding items, wherein in step (b) in addition to the hydroxide a $C_1$-$C_6$ alcohol is present, preferably $C_1$-$C_6$ primary alcohol, more preferably methanol and/or ethanol, even more preferably ethanol.

(6) The process according to any one of preceding items, wherein in step b) the water concentration is less than 30%, preferably less than 10%, more preferably less than 3%, even more preferably less than 1%, most preferably the transformation is performed in a non-aqueous medium.

(7) The process according to any one of the preceding items, wherein Z is —NH—$CH_2$—Ar.

(8) The process according to any one of the preceding items, wherein the compound of formula (I) is a compound of formula (Ia) or a salt thereof

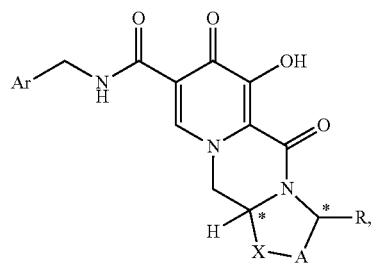

(Ia)

and wherein the compound of formula (II) is a compound of formula (IIa) or a salt thereof

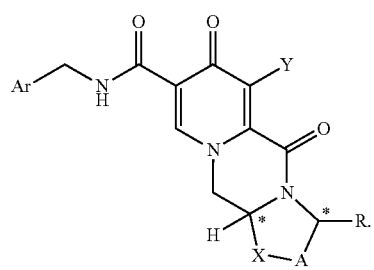

(IIa)

(9) The process according to any one of the preceding items, wherein Ar is 2,4-difluorophenyl.

(10) The process according to any one of the preceding items, wherein Y is Cl.

(11) The process according to any one of the preceding items, wherein the compound of formula (II) is a compound of formula (II-1) or a salt thereof

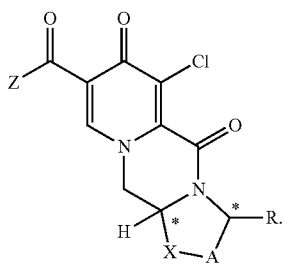
(II-1)

and wherein the compound of formula (IIa) is a compound of formula (IIa-1) or a salt thereof

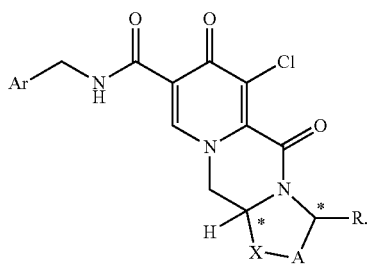
(IIa-1)

(12) The process according to any one of items (1) to (5) or item (10) to (11), wherein Z is hydroxy.

(13) The process according to any one of the preceding items, wherein the compound of formula (II-1) is provided by carrying out a chlorination reaction on a compound of formula (III) or a salt thereof

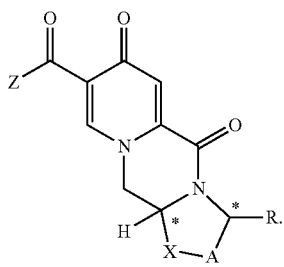
(III)

(14) The process according to any one of items (1) to (12), wherein the compound of formula (II-1) is provided by carrying out a chlorination reaction on a compound of formula (V)

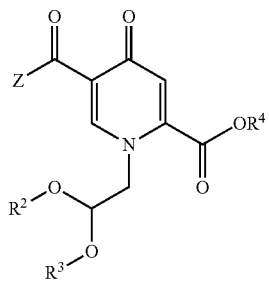
(V)

to obtain a compound of formula (IV) or a salt thereof

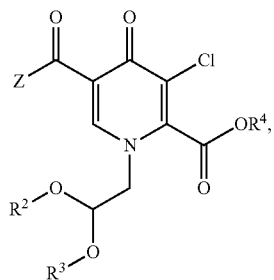
(IV)

and by subsequently transforming the compound of formula (IV) or a salt thereof to the compound of formula (II) or a salt thereof, wherein $R^2$ and $R^3$ independently represent H, $C_1$-$C_4$ alkyl or benzyl or are fused to represent a $C_2$-$C_4$ alkylene chain, and $R^4$ represents H or $C_1$-$C_4$ alkyl.

(15) The process according to item (13) or (14), wherein chlorination is carried out by a chlorinating agent in the presence of a solvent.

(16) The process according to item (15), wherein the chlorinating agent is selected from a compound of formula (CA1)

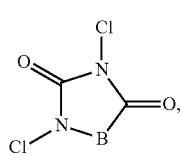
(CA1)

wherein B represents —CO—NH—, —CO—NCl—, or —$CR^6R^7$—, wherein $R^6$ and $R^7$ independently represent $C_1$-$C_4$ alkyl.

(17) The process according to item (15) or item (16), wherein the chlorinating agent is trichloroisocyanuric acid (TCCA) or 1,3-dichloro-5,5-dimethylhydantoin (DCDMH).

(18) The process according to any one of items (15) to (17), wherein the solvent comprises acetonitrile or dichloromethane, preferably is acetonitrile.

(19) The process according to any one of items (15) to (18), wherein the chlorinating agent is used in stoichiometric excess.

(20) The process according to items (1) to (12) or items (14) to (19), wherein the compound of formula (II-1) or a salt thereof

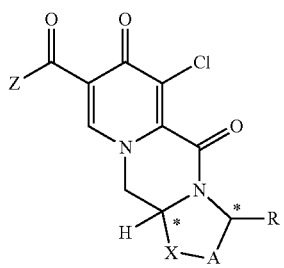
(II-1)

is provided by reacting the compound of formula (IV), wherein $R^2$ and $R^3$ represent H, and $R^4$ represents H or $C_1$-$C_4$ alkyl.

with a compound of formula (VI)

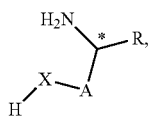

wherein X, A, R and * have the same meaning as set forth in item (1),
preferably with (R)-3-aminobutanol.

(21) The process according to items (1) to (12) or items (14) to (19), wherein the compound of formula (II-1) or a salt thereof

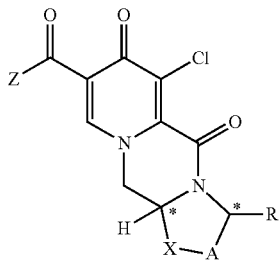

is provided by treating the compound of formula (IV),
wherein $R^2$ and $R^3$ independently represent $C_1$-$C_4$ alkyl or benzyl or are fused to represent a $C_2$-$C_4$ alkylene chain, and $R^4$ represents H or $C_1$-$C_4$ alkyl,
with an acid,
and subsequently reacting with a compound of formula (VI)

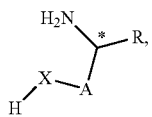

wherein X, A, R and * have the same meaning as set forth in item (1), preferably with (R)-3-aminobutanol.

(22) The process according to item (13) or items (15) to (19), wherein the compound of formula (III) is obtained by reacting the compound of formula (V),
wherein $R^2$ and $R^3$ represent H, and $R^4$ represents H or $C_1$-$C_4$ alkyl.
with a compound of formula (VI)

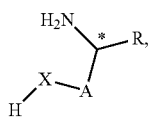

wherein X, A, R and * have the same meaning as set forth in item (1),
preferably with (R)-3-aminobutanol or (S)-alaninol, more preferably (R)-3-aminobutanol.

(23) The process according to item (13) or items (15) to (19), wherein the compound of formula (III) is provided by treating the compound of formula (V),
wherein $R^2$ and $R^3$ independently represent $C_1$-$C_4$ alkyl or benzyl or are fused to represent a $C_2$-$C_4$ alkylene chain, and $R^4$ represents H or $C_1$-$C_4$ alkyl,
with an acid,
and subsequently reacting with a compound of formula (VI)

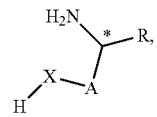

wherein X, A, R and * have the same meaning as set forth in item (1),
preferably with (R)-3-aminobutanol or (S)-alaninol, more preferably (R)-3-aminobutanol.

(24) The process according to items (14) to (23), wherein
Z is hydroxy,
$R^2$ is $C_1$-$C_4$ alkyl, preferably Me,
$R^3$ is $C_1$-$C_4$ alkyl, preferably Me,
and $R^4$ is H.

(25) The process according to any one of items (14) to (23), wherein the compound of formula (V) is prepared by conversion of a compound of formula (VII)

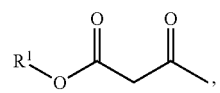

wherein $R^1$ represents $C_1$-$C_4$ alkyl or benzyl, preferably methyl, or ethyl
with a methine group generating reagents, selected from dimethylformamide acetals, formic ortoesters, formic aminal esters, formic iminoesters, preferably with a dimethylformamide di($C_1$-$C_4$ alkyl) acetal,
a compound of formula (VIII)

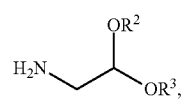

wherein $R^2$ and $R^3$ are as set forth in item (14),
and a compound of formula (IX)

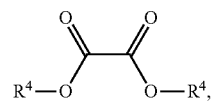

wherein $R^4$ is as set forth in item (14),
further optionally comprising conversion of $OR^1$ to Z.

(26) A process for the preparation of a compound of formula (II-1) or a salt thereof and/or a compound of formula (IV)

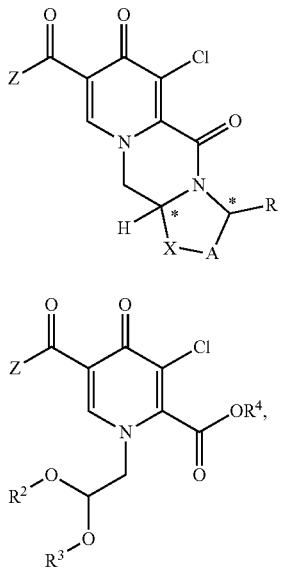

(II-1)

(IV)

wherein

A, R, X, Z and * are defined as set forth in item (1), and $R^2$, $R^3$ and $R^4$ are defined as set forth in item (14), wherein the compound of formula (II-1) is prepared by carrying out a chlorination reaction on the compound of formula (III) as set forth in item (13) and/or the compound of formula (IV) is prepared by carrying out a chlorination reaction on the compound of formula (V) as set forth in item (14).

(27) The process according to item (26), wherein chlorination is carried out as set forth in any one of items (15) to (19).

(28) The process according to any one of items (1) to (9), wherein Y represents O—$R_a$, wherein $R_a$ represents $C_1$-$C_4$ alkyl or benzyl, preferably $C_1$-$C_4$ alkyl, more preferably ethyl or methyl.

(29) The process according to any one of items (1) to (9), wherein the compound of formula (II) is a compound of formula (II-2) or a salt thereof

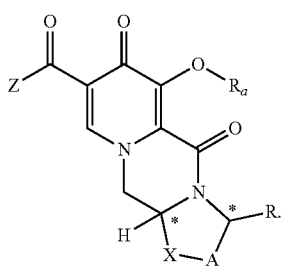

(II-2)

and wherein the compound of formula (IIa) is a compound of formula (IIa-2) or a salt thereof

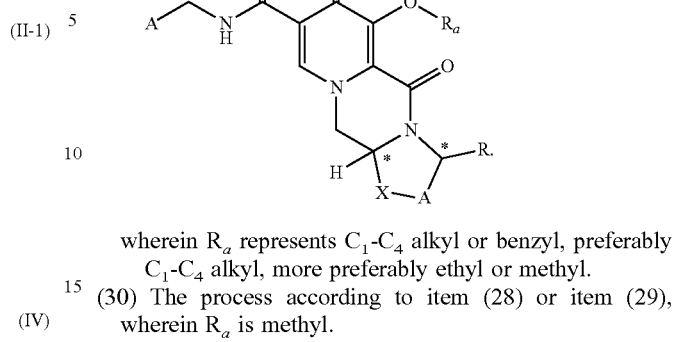

(IIa-2)

wherein $R_a$ represents $C_1$-$C_4$ alkyl or benzyl, preferably $C_1$-$C_4$ alkyl, more preferably ethyl or methyl.

(30) The process according to item (28) or item (29), wherein $R_a$ is methyl.

(31) The process according to item (29) or item (30), wherein the compound of formula (II-2) is prepared by treatment of compound of formula (II-1) with a metal alkoxide of formula $MOR_a$, wherein M is an alkali metal, or an alkali metal hydroxide in an alcohol of formula $R_aOH$, wherein $R_a$ is ($C_1$-$C_4$)-alkyl or benzyl.

(32) The process according to item (29) or item (30), wherein the compound of formula (IIa-2) is prepared by treatment of compound of formula (IIa-1) with a metal alkoxide of formula $MOR_a$, wherein M is an alkali metal or an alkali metal hydroxide in an alcohol of formula $R^1OH$, wherein $R_a$ is ($C_1$-$C_4$)-alkyl or benzyl.

Alternatively, the compounds of formula (II-2) and formula (IIa-2) can be prepared according to any process known in the prior art.

(33) The process according to any one of items (1) to (7), wherein the compound of formula (I) is a compound of formula (Ib) or a salt thereof

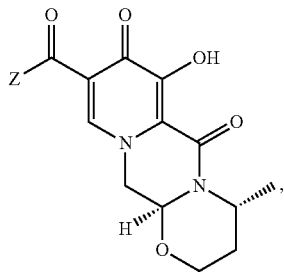

(Ib)

and wherein the compound of formula (II) is a compound of formula (IIb) or a salt thereof

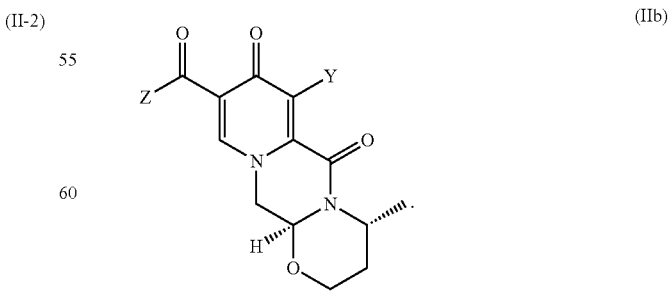

(IIb)

(34) The process according to any one of items (8) to (10) or item (28), wherein the compound of formula (Ia) is a compound of formula (Iab) or a salt thereof

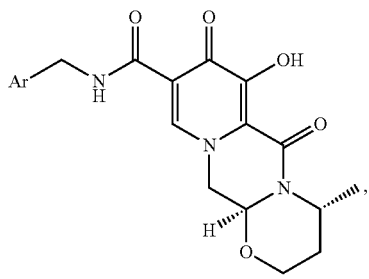
(Iab)

and wherein the compound of formula ((IIa) is a compound of formula (IIab)

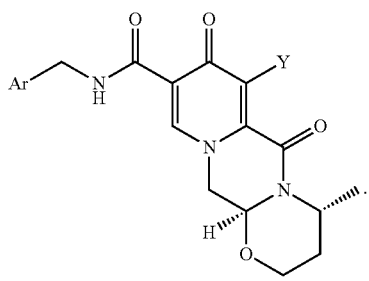
(IIab)

(35) The process according to any one of items (11) to (25), wherein the compound of formula (II-1) is a compound of formula (IIb-1) or a salt thereof

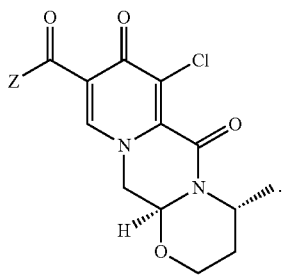
(IIb-1)

and wherein the compound of formula (IIa) is a compound of formula (IIab-1)

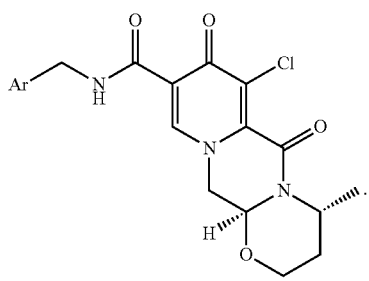
(IIab-1)

(36) The process according to any one of items (29) to (32), wherein the compound of formula (II-2) is a compound of formula (IIb-2) or a salt thereof

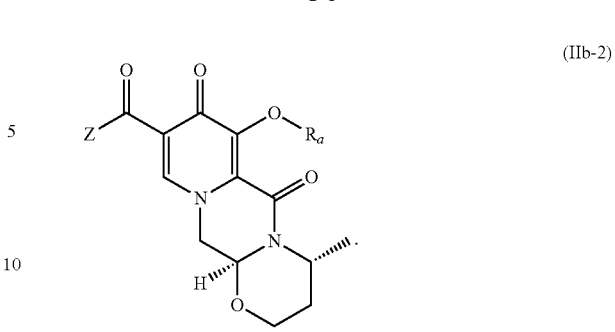
(IIb-2)

and wherein the compound of formula (IIa-2) is a compound of formula (IIab-2)

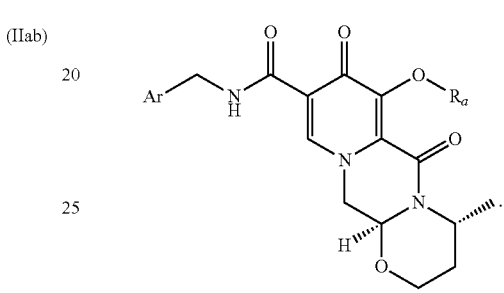
(IIab-2)

wherein $R_a$ represents $C_1$-$C_4$ alkyl or benzyl, preferably $C_1$-$C_4$ alkyl, more preferably ethyl or methyl.

(37) The process according to any one of items (13) items (22) to (23), wherein the compound of formula (III) is a compound of formula (IIIb) or a salt thereof

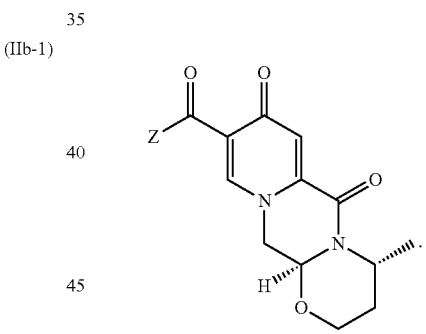
(IIIb)

(38) The process according to any one of items (1) to (25) or items (28) to (37), wherein dolutegravir or a pharmaceutically acceptable salt or solvate thereof is prepared.

(39) A process for preparing dolutegravir or its salts, comprising the steps of
(a) providing a compound of formula (6Y)

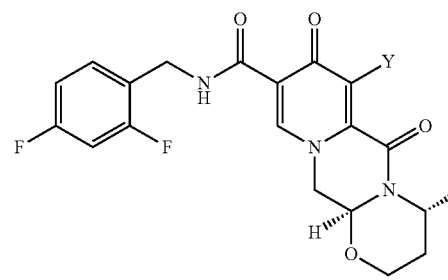
6Y wherein Y represents Cl or O—R$_a$,
wherein R$_a$ represents C$_1$-C$_4$ alkyl or benzyl, preferably C$_1$-C$_4$ alkyl, more preferably ethyl or methyl, most preferably methyl,
and
(b) carrying out a chemical transformation to obtain dolutegravir and/or a salt thereof, wherein the transformation is carried out in the presence of a hydroxide.

(40) The process according to item (39), wherein the hydroxide is a metal hydroxide, preferably is an alkali metal hydroxide, more preferably is sodium hydroxide.

(41) The process according to any one of items (38) to (40), wherein said hydroxide in step b) is added in a solid state.

(42) The process according to any one of items (39) to (41), wherein the hydroxide is used in a 1.2 to 10 molar excess, preferably in a 3 to 7 molar excess, most preferably in a 5 molar excess, compared to the compound of formula (6Y).

(43) The process according to any one of items (39) to (42), wherein in addition to the hydroxide a C$_1$-C$_4$ alcohol is present, preferably C$_1$-C$_4$ primary alcohol, more preferably methanol and/or ethanol, even more preferably ethanol.

(44) The process according to any one of items (39) to (43), wherein in step b) the water concentration is less than 30%, preferably less than 10%, more preferably less than 3%, even more preferably less than 1%, most preferably the transformation is performed in a non-aqueous medium.

(45) A process for preparing dolutegravir in neutral form according to any one of items (39) to (44), wherein after step b) the obtained product is further acidified.

(46) A process for preparing a sodium salt of dolutegravir, wherein a compound of formula (6Y)

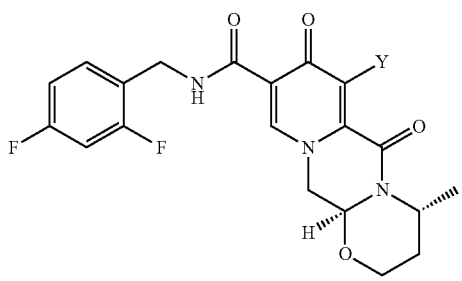

6Y is reacted with sodium hydroxide to directly obtain the sodium salt of dolutegravir.

(47) The process according to item (46), wherein sodium hydroxide is added in a solid state.

(48) The process according to item (47), wherein the hydroxide is used in a 1.2 to 10 molar excess, preferably in a 3 to 7 molar excess, most preferably in a 5 molar excess, compared to the compound of formula (6Y).

(49) The process according to any one of items (46) to (48), wherein in addition to the hydroxide a C$_1$-C$_4$ alcohol is present, preferably C$_1$-C$_4$ primary alcohol, more preferably methanol and/or ethanol, even more preferably ethanol.

(50) The process according to any one of items (46) to (49), the water concentration is less than 30%, preferably less than 10%, more preferably less than 3%, even more preferably less than 1%, most preferably the transformation is performed in a non-aqueous medium.

(51) The process according to any one of items (39) to (50), wherein the sodium salt of dolutegravir is isolated, preferably by filtration, or is further converted to dolutegravir in neutral form, preferably by acidification with an acid.

(52) A process according to item (45) or item (51), wherein obtained dolutegravir in neutral form is transformed to dolutegravir pharmaceutically acceptable salt, preferably to dolutegravir sodium salt.

(53) The process according to any one of items (39) to (52), wherein Y is Cl.

(54) The process according to any one of items (39) to (53), wherein the compound of formula 6Y is a compound of formula (6)

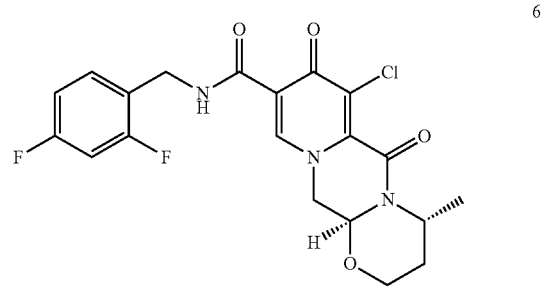 [SMILES: C[C@@H]1CCO[C@H]2Cn3cc(C(=O)NCc4ccc(F)cc4F)c(=O)c(Cl)c3C(=O)N12]

6

(55) The process according to any one of items (39) to (52), wherein Y represents O—R$_a$, wherein R$_a$ represents C$_1$-C$_4$ alkyl or benzyl, preferably C$_1$-C$_4$ alkyl, more preferably ethyl or methyl.

(56) The process according to any one of items (39) to (52) or item (55), wherein the compound of formula (6Y) is a compound of formula (6-2)

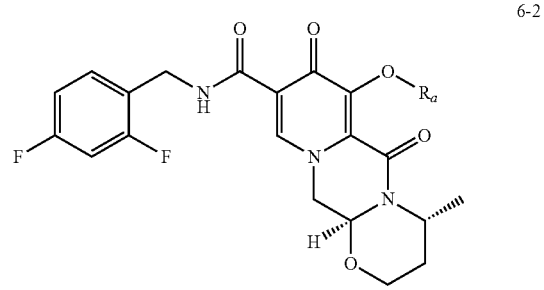

6-2 wherein R$_a$ represents C$_1$-C$_4$ alkyl or benzyl, preferably C$_1$-C$_4$ alkyl, more preferably ethyl or methyl.

(57) The process according to item (55) or item (56), wherein R$_a$ is methyl,

(58) The process according to any one of items (55) to (57), wherein the compound of formula (6-2) is prepared by treatment of compound of formula (6) with a metal alkoxide of formula MOR$_a$, wherein M is an alkali metal or an alkali metal hydroxide in an alcohol of formula R$_a$OH, wherein R$_a$ is (C$_1$-C$_6$)-alkyl or benzyl.

(59) A process for preparing dolutegravir or a pharmaceutically acceptable salt thereof, wherein the process comprising the steps of:
(i) providing a compound of formula (5)

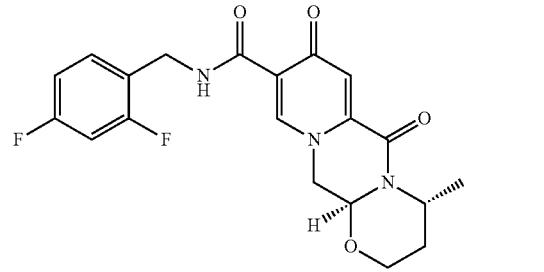

5

(ii) converting the compound of formula (5) to a compound of formula (6)

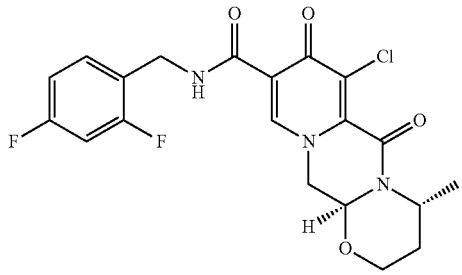

by carrying out a chlorination reaction, and
(iii) converting the compound of formula (6) to dolutegravir and/or a pharmaceutically acceptable salt thereof.
(60) The process according to item (59), wherein in step (iii) the compound of formula (6) is transformed to the compound of formula (6-2) and subsequently converted to dolutegravir and/or a pharmaceutically acceptable salt thereof.
(61) The process according to item (59) or item (60), wherein the chlorination in step (ii) is carried out as set forth in any one of items (15) to (19).
(62) The process according to any one of items (59) to (61), wherein the conversion in step (iii) is carried out in the presence of a hydroxide.
(63) The process according to item (62), wherein the hydroxide is a metal hydroxide, preferably is an alkali metal hydroxide, more preferably is sodium hydroxide.
(64) The process according to any one of item (62) or item (63), wherein said hydroxide is added in a solid state.
(65) The process according to any one of items (62) to (64), wherein the hydroxide is used in a 1.2 to 10 molar excess, preferably in a 3 to 7 molar, most preferably in a 5 molar excess, compared to the compound of formula (6).
(66) The process according to any one of items (62) to (65), wherein in step (iii) in addition to the hydroxide a $C_1$-$C_4$ alcohol is present, preferably $C_1$-$C_4$ primary alcohol, more preferably methanol and/or ethanol, even more preferably ethanol.
(67) The process according to any one of items (59) to (66), wherein the water concentration in step (iii) is less than 30%, preferably less than 10%, more preferably less than 3%, even more preferably less than 1%, most preferably the transformation is performed in a non-aqueous medium.
(68) The process according to any one of items (59) to (67), wherein the compound of formula (5) is provided by converting a compound of formula (3)

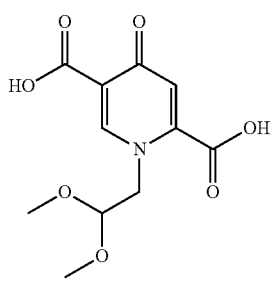

to a compound of formula (4)

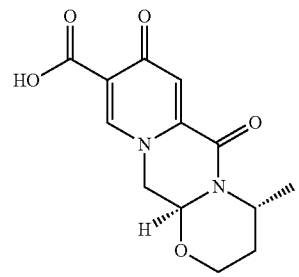

wherein the conversion comprises cyclocondensation with (R)-3-aminobutanol, and by subsequently converting the compound of formula (4) to the compound of formula (5) by amidation with 2,4-difluorobenzylamine.
(69) The process according to any one of items (59) to (68), wherein the compound of formula (5) is provided by process comprising step of
a) a treatment of a compound of formula (3) with an acid

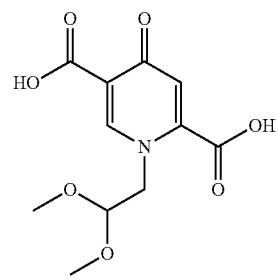

b) a cyclocondensation with (R)-3-aminobutanol to obtain a compound of formula (4)

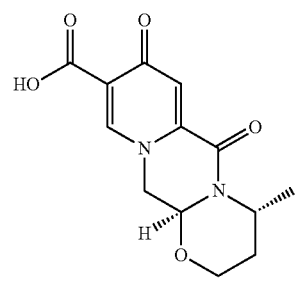

c) converting the compound of formula (4) to the compound of formula (5) by amidation with 2,4-difluorobenzylamine.
(70) The process according to item (68) or item (69), wherein the conversion steps are carried out in one pot.
(71) The process according to any one of items (68) to (70), wherein the compound of formula (3) is prepared by converting a compound of formula (1)

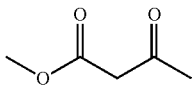

1 with N,N-dimethylformamide dimethyl acetal (DMFDMA) followed by substitution with aminoacetaldehyde dimethyl acetal to obtain a compound of formula (2), and

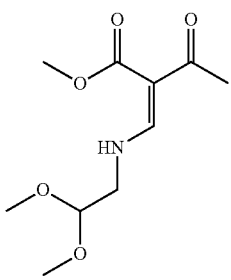

2 by subsequently converting the compound of formula (2) through a cyclocondensation with dimethyl oxalate in the presence of sodium methylate, preferably in 2-propanol, followed by hydrolysis, preferably using aqueous sodium hydroxide, to obtain the compound of formula (3).

(72) The process according to item (71), wherein the conversion steps are carried out in one pot.

(73) A process for preparing a pharmaceutical composition comprising dolutegravir or a pharmaceutically acceptable salt or solvate thereof, the process comprising the steps of carrying out the process according to any one of items (39) to (72) to obtain dolutegravir or a pharmaceutically acceptable salt or solvate thereof, and mixing said obtained dolutegravir or a pharmaceutically acceptable salt or solvate thereof, optionally with another active pharmaceutical ingredient, with a pharmaceutically acceptable excipient, carrier and/or diluent.

(74) A compound of formula (IIa) or a salt thereof

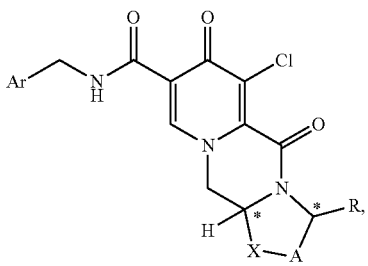

(IIa)

wherein A, R, X, Ar and * are defined as set forth in item (1).

(75) A compound of formula (6)

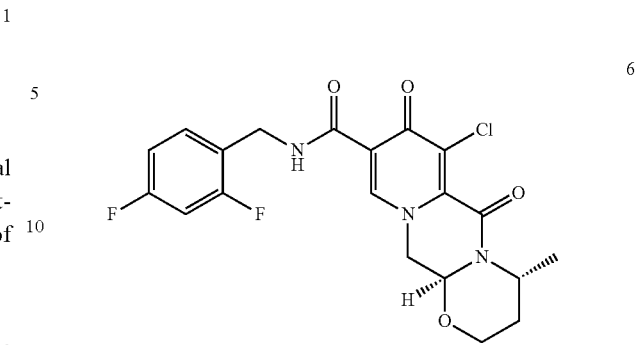

6

(76) A compound of formula (Xa) or a salt thereof

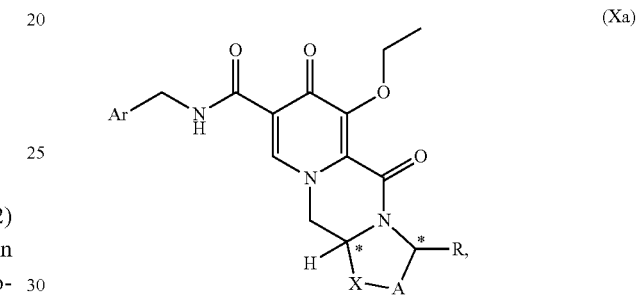

(Xa)

wherein A, R, X, Ar and * are defined as set forth in item (1).

(77) A compound of formula (29)

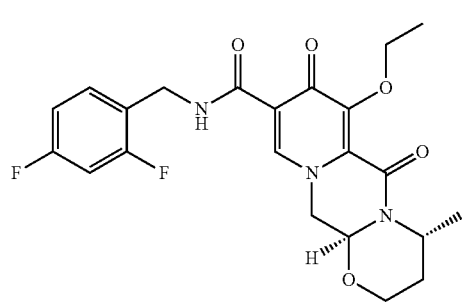

29

(78) Use of a compound (IIa) as defined in item (74), preferably a compound of formula (6) as defined in item (75), for the preparation of an antiviral compound, preferably an HIV integrase inhibitor, in particular dolutegravir or an analogue thereof or a pharmaceutically acceptable salt thereof.

(79) Use of a compound (Xa) as defined in item (76), preferably a compound of formula (29) as defined in item (77), for the preparation of an antiviral compound, preferably an HIV integrase inhibitor, in particular dolutegravir or an analogue thereof or a pharmaceutically acceptable salt thereof.

(80) A compound of formula (4), preferably in crystalline form.

(81) A compound of formula (3), preferably in crystalline form.

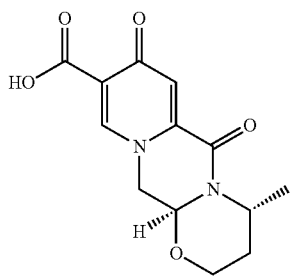

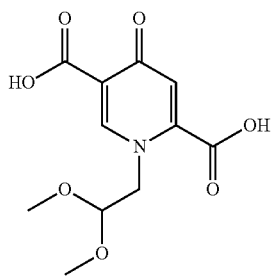

(82) A process for preparing a compound of formula (XI) or a salt thereof

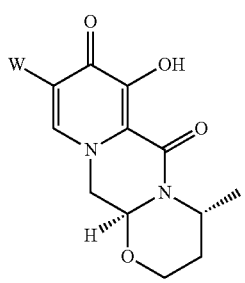

(XI)

wherein
W represents H or CO—Z, wherein Z represents hydroxy, $C_1$-$C_4$ alkoxy, phenoxy, benzoxy, —NH—Ar or, —NH—CH$_2$—Ar, wherein Ar represents unsubstituted or substituted phenyl, and
the process comprising the steps of
(a) providing a compound of formula (XII) or a salt thereof,

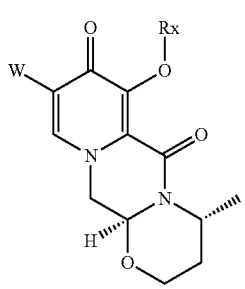

(XII)

wherein
W, Z, and Ar have the same meaning as above and $R_X$ is selected from ($C_1$-$C_6$)-alkyl, unsubstituted or substituted aryl, or unsubstituted or substituted benzyl, and
(b) carrying out a chemical transformation to obtain the compound of formula (XI) and/or a salt thereof, wherein the transformation is carried out in the presence of a hydroxide.

(83) The process according to item (82), wherein
W represents H, carboxy, or CO—Z, wherein Z represents 2,4-difluorophenyl, and
$R_X$ is selected from methyl, ethyl, or benzyl.

(84) A process for preparing a compound of formula (XI) or a salt thereof

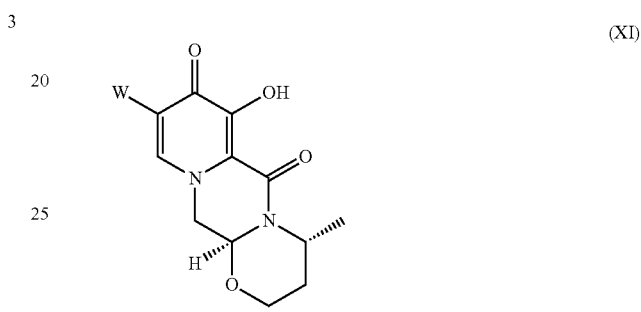

(XI)

wherein
W represents H or CO—Z, wherein Z represents hydroxy, $C_1$-$C_4$ alkoxy, phenoxy, benzoxy, —NH—Ar or, —NH—CH$_2$—Ar, wherein Ar represents unsubstituted or substituted phenyl, and
the process comprising the steps of
(a) providing a compound of formula (XIII) or a salt thereof,

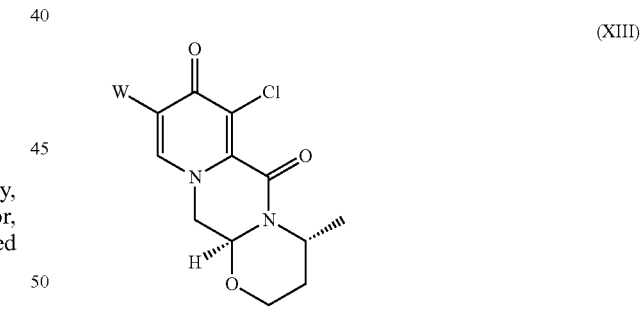

(XIII)

wherein
W, Z, and Ar have the same meaning as above and
(b) carrying out a chemical transformation to obtain the compound of formula (XI) and/or a salt thereof, wherein the transformation is carried out in the presence of a hydroxide.

(85) The process according to item (84), wherein
W represents H, carboxy, or CO—Z, wherein Z represents 2,4-difluorophenyl, and
$R_X$ is selected from methyl, ethyl, or benzyl.

(86) The process according to any one of items (82) to (85), wherein the hydroxide is a metal hydroxide, preferably is an alkali metal hydroxide, more preferably is sodium hydroxide.

(87) The process according to any one of items (82) to (86), wherein the hydroxide in step b) is added in a solid state.
(88) The process according to any one of items (82) to (87), wherein the hydroxide is used in a 1.2 to 10 molar excess, preferably in a 3 to 7 molar excess, most preferably in a 5 molar excess, compared to the compound of formula (II).
(89) The process according to any one of items (82) to (88), wherein in step (b) in addition to the hydroxide a $C_1$-$C_6$ alcohol is present, preferably $C_1$-$C_6$ primary alcohol, more preferably methanol and/or ethanol, even more preferably ethanol.
(90) The process according to any one of items (82) to (89), wherein in step b) the water concentration is less than 30%, preferably less than 10%, more preferably less than 3%, even more preferably less than 1%, most preferably the transformation is performed in a non-aqueous medium.
(91) The process according to any one of items (1) to (7), wherein the compound of formula (I) is a compound of formula (Ic) or a salt thereof

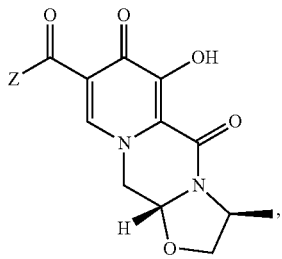

(Ic)

and wherein the compound of formula (II) is a compound of formula (IIc) or a salt thereof

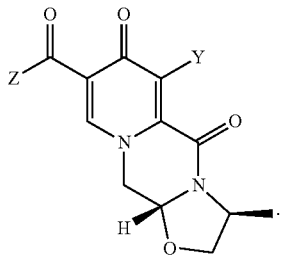

(IIc)

(92) The process according to any one of items (8) to (10) or item (28), wherein the compound of formula (Ia) is a compound of formula (Iac) or a salt thereof

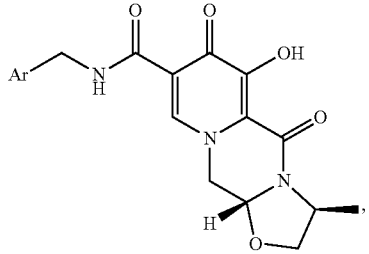

(Iac)

and wherein the compound of formula (IIa) is a compound of formula (IIac)

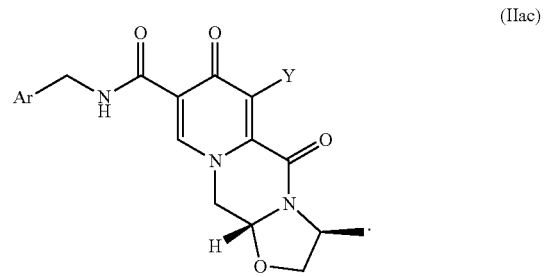

(IIac)

(93) The process according to any one of items (11) to (25), wherein the compound of formula (II-1) is a compound of formula (IIc-1) or a salt thereof

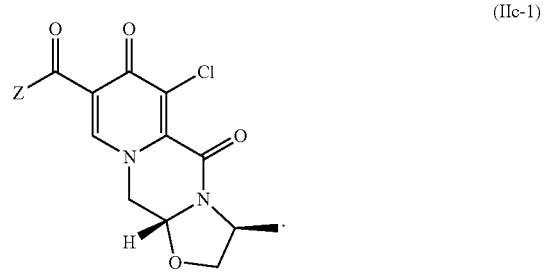

(IIc-1)

and wherein the compound of formula (IIa) is a compound of formula (IIac-1)

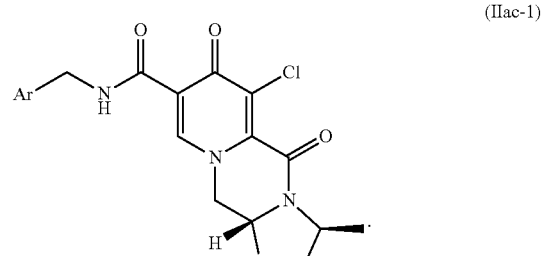

(IIac-1)

(94) The process according to any one of items (29) to (32), wherein the compound of formula (II-2) is a compound of formula (IIc-2) or a salt thereof

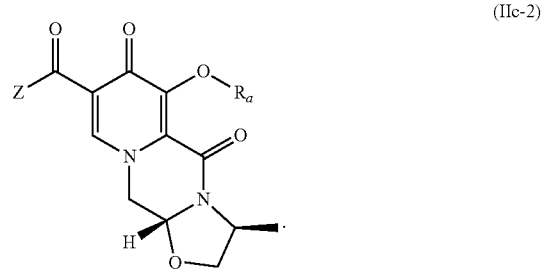

(IIc-2)

and wherein the compound of formula (IIa-2) is a compound of formula (IIac-2)

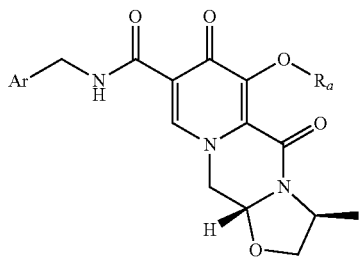

(IIac-2)

wherein $R_a$ represents $C_1$-$C_4$ alkyl or benzyl, preferably $C_1$-$C_4$ alkyl, more preferably ethyl or methyl.

(95) The process according to any one of items (13) items (22) to (23), wherein the compound of formula (III) is a compound of formula (111c) or a salt thereof

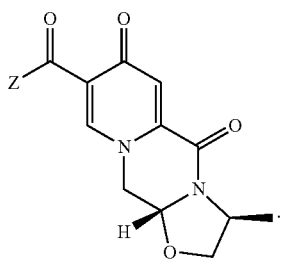

(IIIc)

(96) The process according to any one of items (1) to (25) or items (91) to (95), wherein cabotegravir or a pharmaceutically acceptable salt or solvate thereof is prepared.

(97) A process for preparing cabotegravir or its salts, comprising the steps of
(a) providing a compound of formula (6Yc)

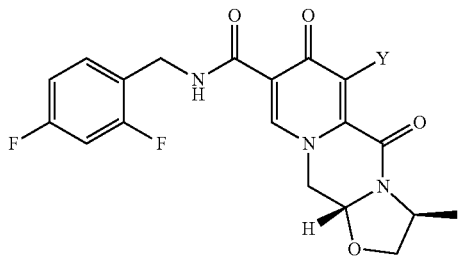

6Yc wherein Y represents Cl or O—$R_a$,
wherein $R_a$ represents $C_1$-$C_4$ alkyl or benzyl, preferably $C_1$-$C_4$ alkyl, more preferably ethyl or methyl, most preferably methyl,
and
(b) carrying out a chemical transformation to obtain cabotegravir and/or a salt thereof, wherein the transformation is carried out in the presence of a hydroxide.

(98) The process according to item (97), wherein the hydroxide is a metal hydroxide, preferably is an alkali metal hydroxide, more preferably is sodium hydroxide.

(99) The process according to any one of items (96) to (98), wherein said hydroxide in step b) is added in a solid state.

(100) The process according to any one of items (97) to (49), wherein the hydroxide is used in a 1.2 to 10 molar excess, preferably in a 3 to 7 molar excess, most preferably in a 5 molar excess, compared to the compound of formula (6Yc).

(101) The process according to any one of items (97) to (100), wherein in addition to the hydroxide a $C_1$-$C_4$ alcohol is present, preferably $C_1$-$C_4$ primary alcohol, more preferably methanol and/or ethanol, even more preferably ethanol.

(102) The process according to any one of items (97) to (101), wherein in step b) the water concentration is less than 30%, preferably less than 10%, more preferably less than 3%, even more preferably less than 1%, most preferably the transformation is performed in a non-aqueous medium.

(103) A process for preparing cabotegravir in neutral form according to any one of items (97) to (102), wherein after step b) the obtained product is further acidified.

(104) A process for preparing a sodium salt of cabotegravir, wherein a compound of formula (6Yc)

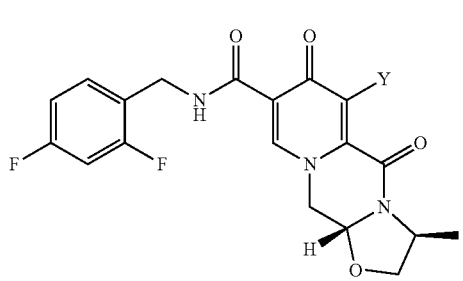

6Yc is reacted with sodium hydroxide to directly obtain the sodium salt of cabotegravir.

(105) The process according to item (104), wherein sodium hydroxide is added in a solid state.

(106) The process according to item (105), wherein the hydroxide is used in a 1.2 to 10 molar excess, preferably in a 3 to 7 molar excess, most preferably in a 5 molar excess, compared to the compound of formula (6Yc).

(107) The process according to any one of items (104) to (106), wherein in addition to the hydroxide a $C_1$-$C_4$ alcohol is present, preferably $C_1$-$C_4$ primary alcohol, more preferably methanol and/or ethanol, even more preferably ethanol.

(108) The process according to any one of items (104) to (107), the water concentration is less than 30%, preferably less than 10%, more preferably less than 3%, even more preferably less than 1%, most preferably the transformation is performed in a non-aqueous medium.

(109) The process according to any one of items (97) to (108), wherein the sodium salt of cabotegravir is isolated, preferably by filtration, or is further converted to cabotegravir in neutral form, preferably by acidification with an acid.

(110) A process according to item (103) or item (109), wherein obtained cabotegravir in neutral form is transformed to cabotegravir pharmaceutically acceptable salt, preferably to cabotegravir sodium salt.

(111) The process according to any one of items (97) to (110), wherein Y is Cl.

(112) The process according to any one of items (97) to (111), wherein the compound of formula 6Yc is a compound of formula (6c)

(113) The process according to any one of items (97) to (110), wherein Y represents O—$R_a$, wherein $R_a$ represents $C_1$-$C_4$ alkyl or benzyl, preferably $C_1$-$C_4$ alkyl, more preferably ethyl or methyl.

(114) The process according to any one of items (97) to (110) or item (113), wherein the compound of formula (6Yc) is a compound of formula (6c-2)

wherein $R_a$ represents $C_1$-$C_4$ alkyl or benzyl, preferably $C_1$-$C_4$ alkyl, more preferably ethyl or methyl.

(115) The process according to item (113) or item (114), wherein $R_a$ is methyl, (116) The process according to any one of items (113) to (115), wherein the compound of formula (6c-2) is prepared by treatment of compound of formula (6c) with a metal alkoxide of formula $MOR_a$, wherein M is an alkali metal or an alkali metal hydroxide in an alcohol of formula $R_a$OH, wherein $R_a$ is ($C_1$-$C_6$)-alkyl or benzyl.

(117) A process for preparing cabotegravir or a pharmaceutically acceptable salt thereof, wherein the process comprising the steps of:
(i) providing a compound of formula (5c)

(ii) converting the compound of formula (5c) to a compound of formula (6c)

by carrying out a chlorination reaction, and
(iii) converting the compound of formula (6c) to cabotegravir and/or a pharmaceutically acceptable salt thereof.

(118) The process according to item (117), wherein in step (iii) the compound of formula (6c) is transformed to the compound of formula (6c-2) and subsequently converted to cabotegravir and/or a pharmaceutically acceptable salt thereof.

(119) The process according to item (117) or item (118), wherein the chlorination in step (ii) is carried out as set forth in any one of items (15) to (19).

(120) The process according to any one of items (117) to (119), wherein the conversion in step (iii) is carried out in the presence of a hydroxide.

(121) The process according to item (120), wherein the hydroxide is a metal hydroxide, preferably is an alkali metal hydroxide, more preferably is sodium hydroxide.

(122) The process according to any one of item (120) or item (121), wherein said hydroxide is added in a solid state.

(123) The process according to any one of items (120) to (122), wherein the hydroxide is used in a 1.2 to 10 molar excess, preferably in a 3 to 7 molar, most preferably in a 5 molar excess, compared to the compound of formula (6c).

(124) The process according to any one of items (120) to (123), wherein in step (iii) in addition to the hydroxide a $C_1$-$C_4$ alcohol is present, preferably $C_1$-$C_4$ primary alcohol, more preferably methanol and/or ethanol, even more preferably ethanol.

(125) The process according to any one of items (117) to (124), wherein the water concentration in step (iii) is less than 30%, preferably less than 10%, more preferably less than 3%, even more preferably less than 1%, most preferably the transformation is performed in a non-aqueous medium.

(126) The process according to any one of items (117) to (125), wherein the compound of formula (5) is provided by converting a compound of formula (3)

to a compound of formula (4c)

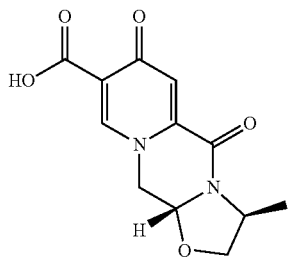

4c wherein the conversion comprises cyclocondensation with (S)-alaninol,
and by subsequently converting the compound of formula (4c) to the compound of formula (5c) by amidation with 2,4-difluorobenzylamine.

(127) The process according to any one of items (117) to (126), wherein the compound of formula (5c) is provided by process comprising step of
a) a treatment of a compound of formula (3) with an acid

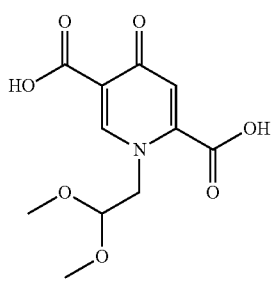

3 b) a cyclocondensation with (S)-alaninol to obtain a compound of formula (4c)

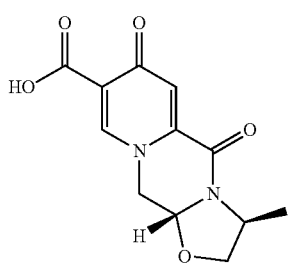

4c c) converting the compound of formula (4c) to the compound of formula (5c) by amidation with 2,4-difluorobenzylamine.

(128) The process according to item (126) or item (127), wherein the conversion steps are carried out in one pot.

(129) The process according to any one of items (126) to (128), wherein the compound of formula (3) is prepared by converting a compound of formula (1)

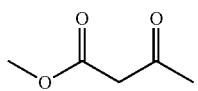

1 with N,N-dimethylformamide dimethyl acetal (DMFDMA) followed by substitution with aminoacetaldehyde dimethyl acetal to obtain a compound of formula (2), and

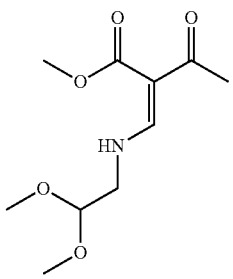

2 by subsequently converting the compound of formula (2) through a cyclocondensation with dimethyl oxalate in the presence of sodium methylate, preferably in 2-propanol, followed by hydrolysis, preferably using aqueous sodium hydroxide,
to obtain the compound of formula (3).

(130) The process according to item (129), wherein the conversion steps are carried out in one pot.

(131) A process for preparing a pharmaceutical composition comprising cabotegravir or a pharmaceutically acceptable salt or solvate thereof, the process comprising the steps of carrying out the process according to any one of items (97) to (130) to obtain cabotegravir or a pharmaceutically acceptable salt or solvate thereof, and mixing said obtained cabotegravir or a pharmaceutically acceptable salt or solvate thereof, optionally with another active pharmaceutical ingredient, with a pharmaceutically acceptable excipient, carrier and/or diluent.

(132) A compound of formula (6c)

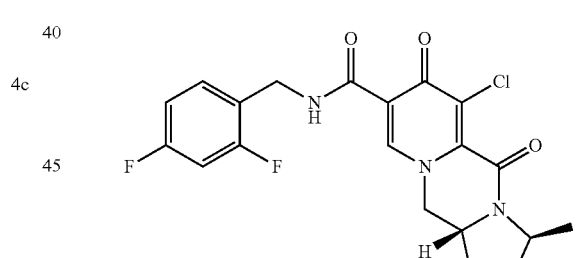

6c (133) A compound of formula (29c)

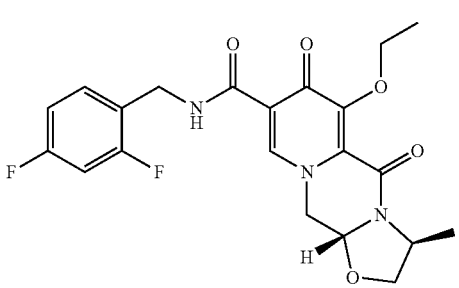

29c (134) Use of a compound of formula (6c) as defined in item (132), for the preparation of an antiviral compound, preferably an HIV integrase inhibitor, in particular cabotegravir or an analogue thereof or a pharmaceutically acceptable salt thereof.

(135) Use of a compound of formula (29c) as defined in item (133), for the preparation of an antiviral compound, preferably an HIV integrase inhibitor, in particular cabotegravir or an analogue thereof or a pharmaceutically acceptable salt thereof.

DETAILED DESCRIPTION

In the following, the present invention is described in more detail while referring to preferred embodiments and examples, which are presented however for illustrative purposes and shall not be construed to limit the invention in any way.

The term "analogue" of dolutegravir and "analogue" of cabotegravir used herein means a respective analogue compound having antiviral function, particularly a HIV integrase inhibitor function.

The term "salt" used herein means any inorganic or organic salt, wherein the type of salt can be chosen to be suitable in the respective context. Preferably, when the respective compound is an intermediate compound the salt may be chosen to readily allow isolation, for example by way of crystallisation using salts generally known for such purpose, or is already chosen from pharmaceutically acceptable salts; when the respective compound is a desired final compound, notably an antiviral compound and particularly a HIV integrase inhibitor such as dolutegravir or cabotegravir or an antiviral analogues thereof, the salt is preferably chosen from generally known pharmaceutically acceptable salts. The salt used herein may have a function of both, being suitable for crystallization/isolation and being suitable as a pharmaceutically acceptable salt. The salt may for example be selected from the group consisting of basic salts including, without being limited to, alkali metal salts such as sodium or potassium salts; alkaline-earth metal salts such as calcium or magnesium salts; ammonium salts; aliphatic or aromatic or aralkyl amine salts; quaternary ammonium salts such as tetramethylammonium or tetraethylammonium salts; basic amino acid salts such as arginine salts or lysine salts; acid salts including, without being limited to, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tartaric acid salts, malates, citrate salts, ascorbates, formic acid salts; sulfonates such as methanesulfonates, isothionates, benzenesulfonates, or p-toluenesulfonates and acidic amino acid salts such as aspartates or glutamates. Preferably the salt is a sodium salt.

The term "dolutegravir in neutral form" used herein means dolutegravir as presented by Formula A and it is not in the form of a salt thereof.

The term "cabotegravir in neutral form" used herein means cabotegravir as presented by Formula C and it is not in the form of a salt thereof.

When the present invention refers to a "compound", its meaning also includes solvates thereof. The term "solvate" or "solvates" used herein is typically a hydrate but may be any other solvate form.

As used herein, the symbol * means a chirality centre, which is of (R) or (S) configuration. This means that the compound may be in either (R) configuration or in (S) configuration, preferably respectively enantiomerically pure form, or it may be a mixture of (R) and (S) configurations, e.g. forming a racemate.

A first aspect of the invention is a process for preparing a compound of formula (I) as set forth in item (1) or a pharmaceutically acceptable salt thereof, wherein the process comprises the steps of providing a compound of formula (II) as set forth in item (1), and carrying out a chemical transformation to obtain the compound of formula (I) and/or a pharmaceutically acceptable salt thereof, wherein the transformation is carried out in the presence of a hydroxide.

The process of the invention provides an advantageous and efficient method to convert the chloro group, $C_1$-$C_4$-alkoxy group or benzyloxy group into the hydroxy group in the particular position of the ring structures as shown in formulae I, I-1 or I-2 and II, II-1 or II-1 respectively. Preferably, the conversion is carried out in the presence of $C_1$-$C_4$ alcohol, preferably $C_1$-$C_4$ primary alcohol, more preferably methanol and/or ethanol, even more preferably ethanol. It is particularly preferred that the chemical conversion takes place in the presence of metal hydroxide, preferably alkali metal hydroxide, more preferably sodium hydroxide, preferably in the presence of methanol and/or ethanol. The combination of sodium hydroxide with methanol and/or ethanol is most preferred. Preferably, the hydroxide in a solid state is used. In the most preferable process the water concentration is less than 30%, preferably less than 10%, more preferably less than 3%, even more preferably less than 1%, most preferably the conversion is performed in a non-aqueous medium.

In particularly preferred embodiments the conversion is carried out in cases where the Z group in formula I and/or II is —NH—$CH_2$—Ar, wherein Ar preferably is 2,4-difluorophenyl, or the Z group is hydroxy.

In an embodiment of the process according to the invention the compound of formula (II) is the compound of formula II-1

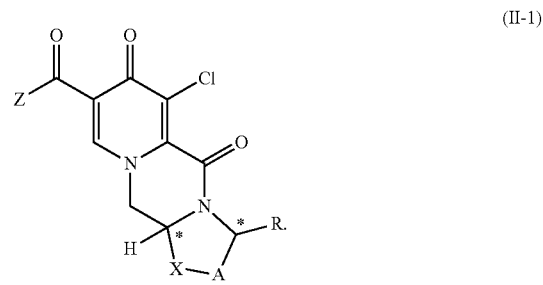

(II-1)

The compound of formula II-1 is provided by carrying out a chlorination reaction on a compound of formula (III) as set forth in item (13). In an alternative embodiment, the compound of formula (II) can be provided by carrying out a chlorination reaction on a compound of formula (V) as set forth in item (14) to obtain a compound of formula (IV) as set forth in item (14), and by subsequently transforming the compound of formula (IV) to the compound of formula (II). Preferably, chlorination is carried out by a chlorinating agent in the presence of a solvent. Preferably, the chlorinating agent is selected from a compound of formula (CA1) as defined in item (16). In preferred embodiments trichloroisocyanuric acid (TCCA) or 1,3-dichloro-5,5-dimethylhydantoin (DCDMH) is used. Advantageous and preferable solvents comprise acetonitrile and dichloromethane. Most preferably acetonitrile is used. For the chlorination reactions according to the invention, most preferably TCCA in acetonitrile is used. Particularly favorable results are obtainable when the chlorinating agent is used in stoichiometric excess.

In the present invention it was found that a particularly advantageous and preferable synthetic method can be achieved when the process comprises not only the conversion of chloro to hydroxy, but also the prior introduction of the chloro group. Favorably, these functionalization steps can be neighboring steps, while it is also possible to carry out other steps in between. In a most preferred embodiment these two functional conversions are carried out at late synthetic stages.

In a further embodiment of the inventive process the compound of formula (II-1) is provided by reacting the compound of formula (IV) with a compound of formula (VI) as set forth in item (20) or item (21).

In particular cases where dolutegravir, or particular analogues thereof, is the synthetic target the use of (R)-3-aminobutanol as a compound of formula (VI) is particularly preferable, especially in view of the stereochemistry of the target compound. In particular cases where cabotegravir, or particular analogues thereof, is the synthetic target the use of (S)-alaninol as a compound of formula (VI) is particularly preferable. The compound of formula (III) can be obtained by reacting the compound of formula (V) with a compound of formula (VI), preferably (R)-3-aminobutanol or (S)-alaninol, more preferably (R)-3-aminobutanol, as set forth in item (22) or item (23). In a particular embodiment, the compound of formula (V) is prepared by conversion of a compound of formula (VII) as defined in item (25) with dimethylformamide di($C_1$-$C_4$ alkyl) acetal, a compound of formula (VIII) as set forth in item (25) and a compound of formula (IX), likewise defined in item (25).

In a particularly preferred embodiment dolutegravir or a pharmaceutically acceptable salt or solvate thereof is prepared. Therefore, another aspect of the invention is a process for preparing a pharmaceutical composition comprising dolutegravir or a pharmaceutically acceptable salt or solvate thereof, the process comprising the steps of carrying out the process of the invention to obtain dolutegravir or a pharmaceutically acceptable salt or solvate thereof, and mixing dolutegravir or a pharmaceutically acceptable salt or solvate thereof obtained according to the invention, optionally with another active pharmaceutical ingredient, with a pharmaceutically acceptable excipient, carrier and/or diluent.

In another particularly preferred embodiment cabotegravir or a pharmaceutically acceptable salt or solvate thereof is prepared. Therefore, another aspect of the invention is a process for preparing a pharmaceutical composition comprising cabotegravir or a pharmaceutically acceptable salt or solvate thereof, the process comprising the steps of carrying out the process of the invention to obtain cabotegravir or a pharmaceutically acceptable salt or solvate thereof, and mixing cabotegravir or a pharmaceutically acceptable salt or solvate thereof obtained according to the invention, optionally with another active pharmaceutical ingredient, with a pharmaceutically acceptable excipient, carrier and/or diluent.

In an embodiment of the process according to the invention the compound of formula (II) is the compound of formula (II-2)

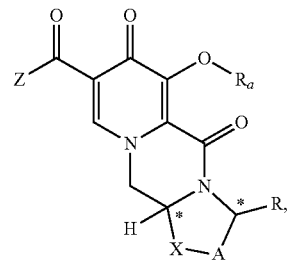

(II-2)

wherein $R_a$ represents $C_1$-$C_4$ alkyl or benzyl, preferably $C_1$-$C_4$ alkyl, more preferably ethyl or methyl.

In particular, dolutegravir or a pharmaceutically acceptable salt or solvate thereof, or cabotegravir or a pharmaceutically acceptable salt or solvate thereof is admixed with at least one suitable pharmaceutically acceptable excipient. Pharmaceutically acceptable excipients may be selected from the group consisting of diluents, carriers, binders, disintegrating agents, stabilizing agents, preservatives, lubricants, surfactants, fragrances, flavouring agents, sweeteners and other excipients known in the field of the pharmaceutical technology. For example, suitable excipients may be selected from the group consisting of lactose, microcrystalline cellulose, cellulose derivatives, such as hydroxypropylcellulose, polyacrylates, calcium carbonate, starch, mannitol, colloidal silicone dioxide, sodium starch glycolate, sodium stearyl fumarate, croscarmellose sodium, talc, magnesium stearate, polyvinylpyrrolidone, polyvinyl alcohol, polyethylene glycol, macrogol, titanium dioxide, iron oxides and other excipients known in the field of the pharmaceutical technology.

In another aspect of the invention there are provided compound of formulas (IIa), (IIa-1) or (IIa-2) a pharmaceutically acceptable salts thereof

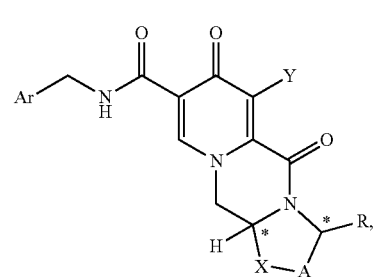

(IIa)

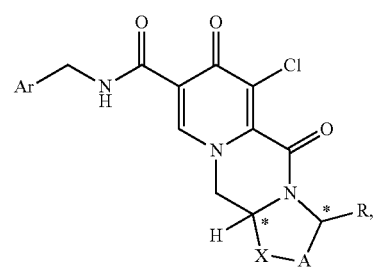

(IIa-1)

-continued

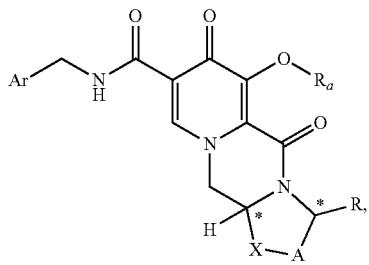

(IIa-2)

wherein Y, A, R, X, Ar and * are defined as set forth in item (1), and
a compound of formula (6) or a pharmaceutically acceptable salt thereof

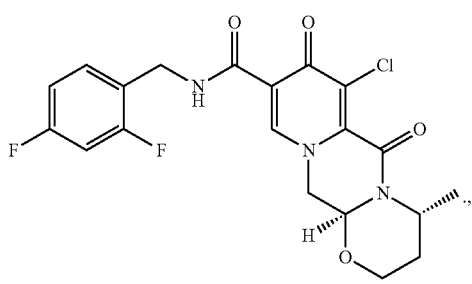

6 and a compound of formula (6c) or a pharmaceutically acceptable salt thereof

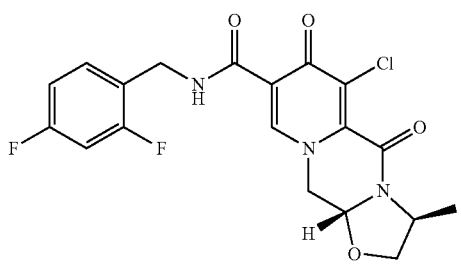

6c

These compounds constitute favorable intermediates useful in further syntheses, for example in the preparation of cabotegravir, dolutegravir and analogues thereof.

Another aspect of the invention is a process for the preparation of a compound of formula (II-1) as set forth in item (13) or item (14) and/or a compound of formula (IV) as set forth in item (14), wherein the compound of formula (II-1) is prepared by carrying out a chlorination reaction on the compound of formula (III) as set forth in item (13) and/or the compound of formula (IV) is prepared by carrying out a chlorination reaction on the compound of formula (V) as set forth in item (14). Preferably, chlorination is carried out as described above.

Advantageously, according to the present inventive process a sodium salt of dolutegravir can be directly obtained by reacting a compound of formula (6Y) as set forth in item (46), preferably a compound of formula (6) as set forth in item (54) or a compound of formula (6-2) as set forth in item (56), with sodium hydroxide, preferably in the presence of $C_1$-$C_4$ alcohol, preferably in the presence of methanol and/or ethanol. Preferably, the hydroxide in a solid state is used. Most preferable the water concentration is less than 30%, preferably less than 10%, more preferably less than 3%, even more preferably less than 1%, most preferably the conversion is performed in a non-aqueous medium. The thus obtained sodium salt of dolutegravir can be isolated, preferably by filtration, or it can be further converted to the dolutegravir in neutral form, preferably by acidification with an aqueous acid.

By the analogy, according to the present inventive process a sodium salt of cabotegravir can be directly obtained by reacting a compound of formula (6Yc) as set forth in item (104), preferably a compound of formula (6c) as set forth in item (112) or a compound of formula (6c-2) as set forth in item (114), with sodium hydroxide, preferably in the presence of C1-C4 alcohol, preferably in the presence of methanol and/or ethanol.

In another aspect of the invention there is provided a process for preparing dolutegravir or a pharmaceutically acceptable salt thereof which comprises providing a compound of formula (5)

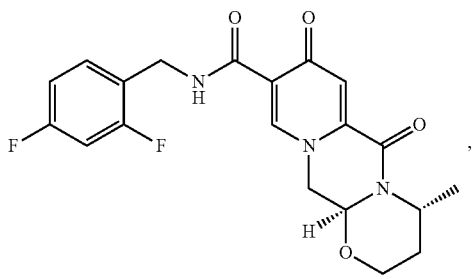

5 converting the compound of formula (5) to a compound of formula (6)

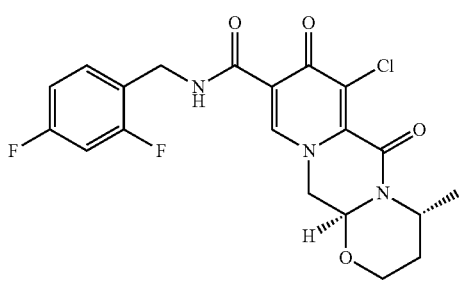

6 by carrying out a chlorination reaction, and converting the compound of formula (6) to dolutegravir and/or a pharmaceutically acceptable salt thereof. The chlorination in step (ii) is preferably carried out as set forth in any one of items (15) to (19) to enable a particularly effective and efficient conversion. The introduction of the hydroxy group on the chloro compound can be favorably carried out in the presence of hydroxide, preferably sodium hydroxide, and methanol and/or ethanol. The compound of formula (5) can preferably be provided by converting a compound of formula (3)

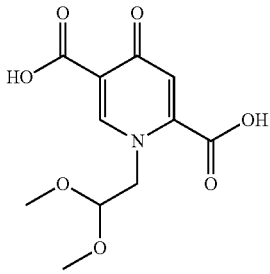

3 to a compound of formula (4)

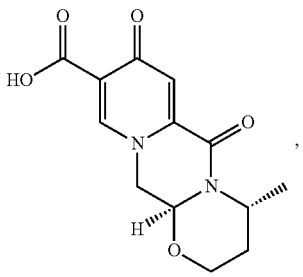

4 wherein the conversion comprises cyclocondensation with (R)-3-aminobutanol, and by subsequently converting the compound of formula (4) to the compound of formula (5) by amidation with 2,4-difluorobenzylamine. Preferably, an activating agent is used for the amidation step. The compound of formula (3) is first treated with an acid to cleave the acetal to form intermediates, which are not isolated but further submitted to amidation without a special treatment.

In a particularly preferred embodiment the compound of formula (3) is prepared by converting a compound of formula (1)

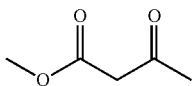

1 with N,N-dimethylformamide dimethyl acetal (DMFDMA) followed by substitution with aminoacetaldehyde dimethyl acetal to obtain a compound of formula (2), and by

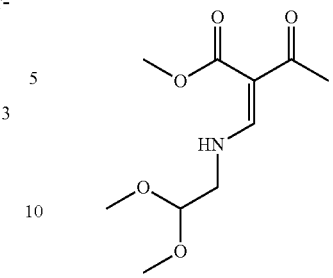

2 subsequently converting the compound of formula (2) through a cyclocondensation with dimethyl oxalate in the presence of sodium methylate, preferably in 2-propanol, followed by hydrolysis, preferably using aqueous sodium hydroxide, to obtain the compound of formula (3). Likewise, these conversion steps are preferably carried out in one pot which provides benefits in terms of process efficiency and economy. Moreover, purification can be favorably improved by obtaining crystalline intermediates.

In a particularly preferred embodiment the process of the invention is carried out according to a synthetic route as shown Scheme 1. Therein, synthesis starts with methyl acetoacetate (1), which is transformed to the solid intermediate 2, preferably using a one-pot reaction, with N,N-dimethylformamide dimethyl acetal (DMFDMA), followed by the substitution with aminoacetaldehyde dimethyl acetal. The aminopropenoate 2 is then subjected, preferably in one pot, to a cyclocondensation with dimethyl oxalate in the presence of sodium methylate in 2-propanol, followed by the double ester hydrolysis using an aqueous sodium hydroxide. Particularly preferably, all these steps can favourably be merged to a one-pot process without detrimental effects to yields and purity. The thus obtained crystalline dicarboxylic acid 3 is subjected, preferably in a one-pot scheme, to acid catalysed deacetalization and a cyclocondensation with (R)-3-aminobutanol to give the crystalline tricyclic carboxylic acid 4. The amidation of 4 with 2,4-difluorobenzylamine employing ethyl chloroformate as the activation reagent gives the crystalline 5, which is then chlorinated, preferably with trichloroisocyanuric acid (TCCA), in acetonitrile to give the chloro derivative 6 as a crystalline solid. This compound is then subjected to a reaction with sodium hydroxide in ethanol to initially give a precipitate of the insoluble dolutegravir sodium salt. This salt can be directly isolated, e.g. by filtration, and used further. Alternatively, it can also be liberated to the solid free acid dolutegravir by the acidification with an aqueous acid during the reaction work up. Scheme 1 shows the synthesis of dolutegravir according to a particularly preferred embodiment of present invention.

Scheme 1
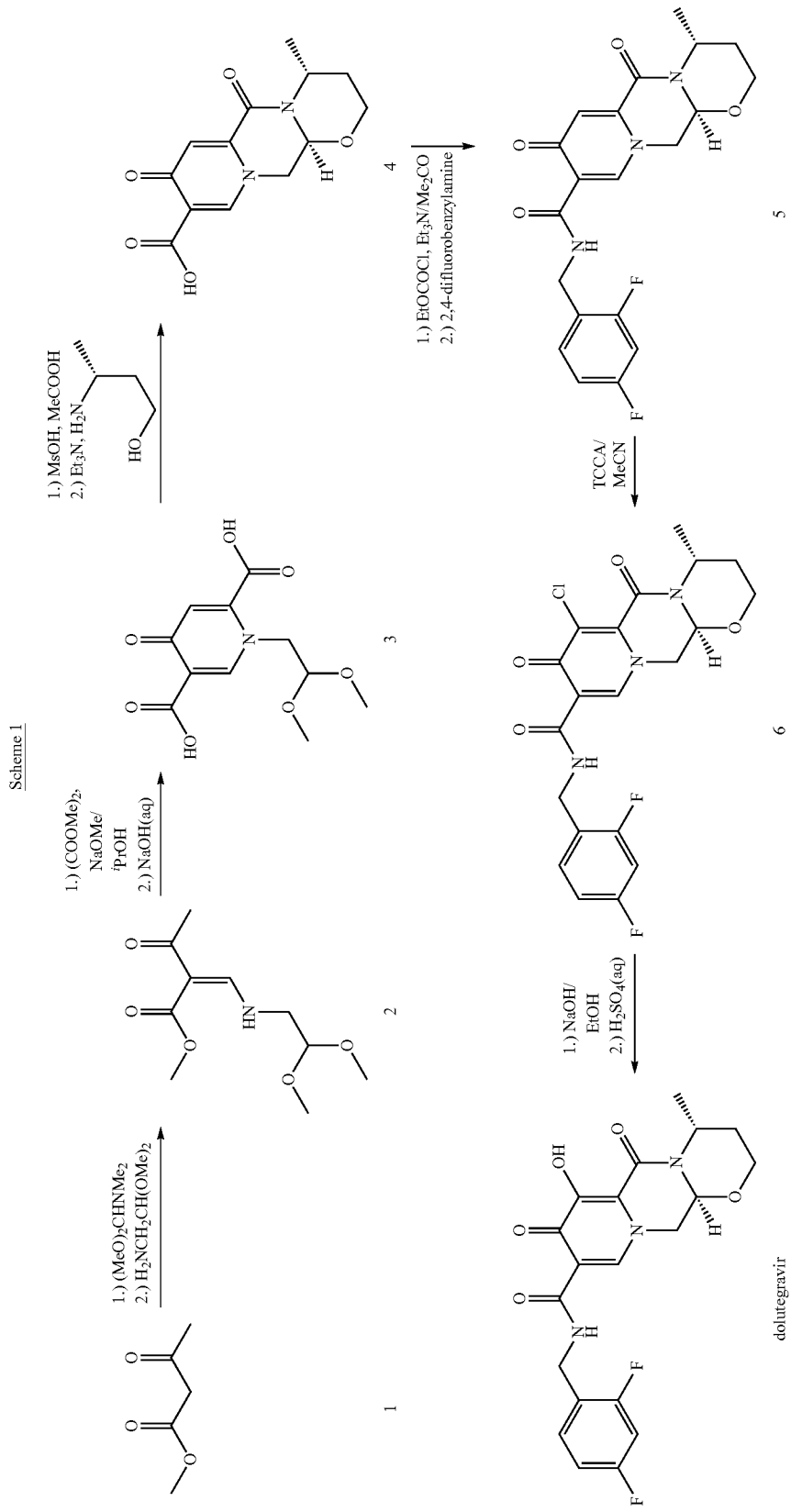

According to an embodiment of the process of the invention the building block 3-aminobutanol can suitably be substituted with other aminoalcohols to give dolutegravir analogues. For example, using (S)-alaninol gives cabotegravir as the final product. Similarly, using amines other than 2,4-difluorobenzylamine in the amidation step results in the synthesis of other dolutegravir analogues.

According to the another preferred embodiment cabotegravir or a pharmaceutically acceptable salt thereof is prepared by the analogue process, which comprises providing a compound of formula (5c)

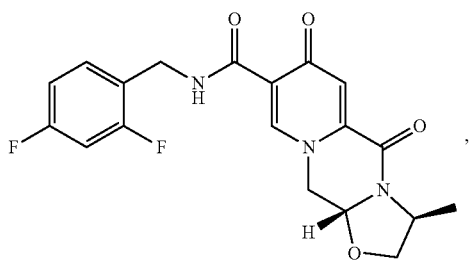

converting the compound of formula (5c) to a compound of formula (6c)

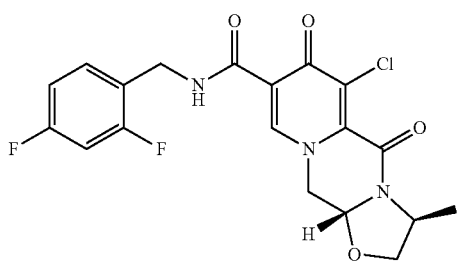

by carrying out a chlorination reaction, and converting the compound of formula (6c) to cabotegravir and/or a pharmaceutically acceptable salt thereof.

The compound of formula (5c) can preferably be provided by converting a compound of formula (3) to a compound of formula (4c)

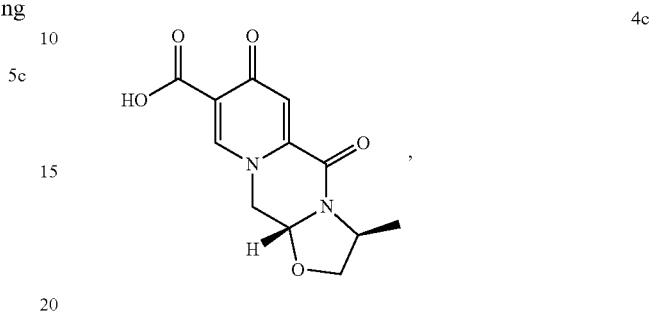

wherein the conversion comprises cyclocondensation with (s)-3-alaninol, and by subsequently converting the compound of formula (4c) to the compound of formula (5c) by amidation with 2,4-difluorobenzylamine.

In another embodiment according to the invention the order of reaction steps is changed, in particular between the amidation and the chlorination. That is, compounds 4 and 4c are first chlorinated to give the carboxylic acids 7 and 7c, respectively, which are then amidated to give 6 and 6c, respectively. The chlorination and the amidation reactions are preferably performed using the same synthetic methods as shown in Scheme 1, therefore preferably employing TCCA in acetonitrile and ethyl chloroformate correspondingly. Scheme 2 shows a variation in the order of reaction steps between the intermediates 4 and 6.

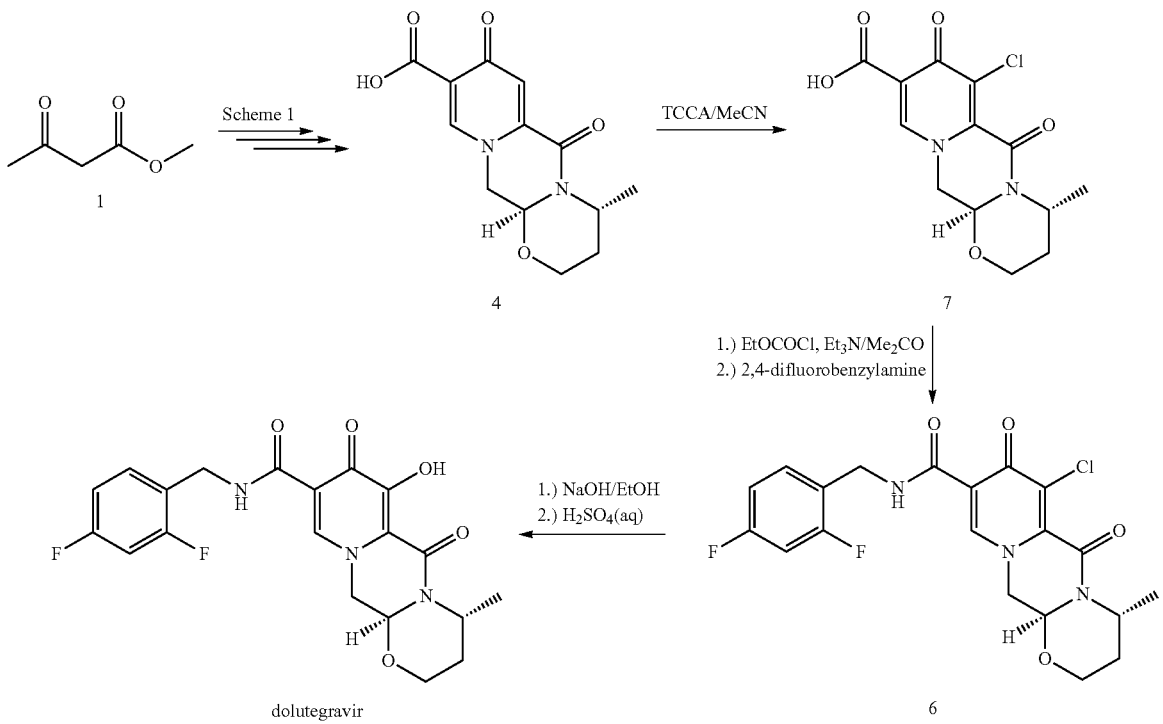

In an embodiment, the chlorinated intermediate 7 can be reacted with sodium methylate in methanol to give its methoxy substitution derivative 8, which is known to represent a useful intermediate in the synthesis of dolutegravir. Scheme 3 shows the use of the intermediate 7 in a suitable series of synthetic steps.

Scheme 3

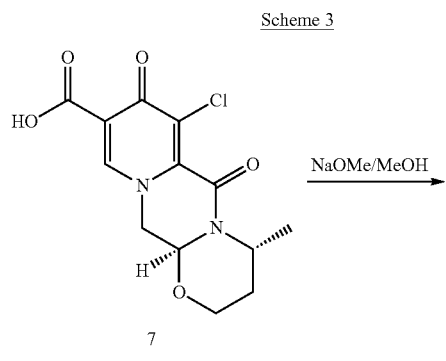

7

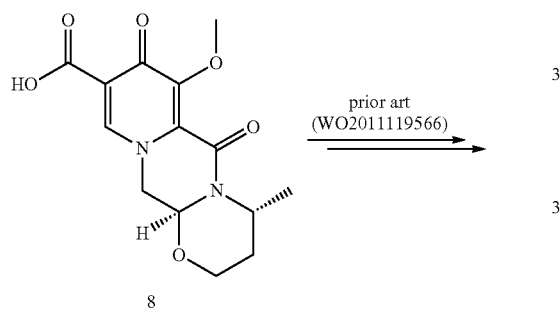

8

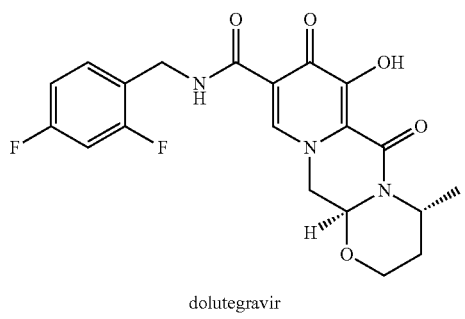

dolutegravir

Analogous compound of formula 7c is a useful intermediate in the synthesis of cabotegravir.

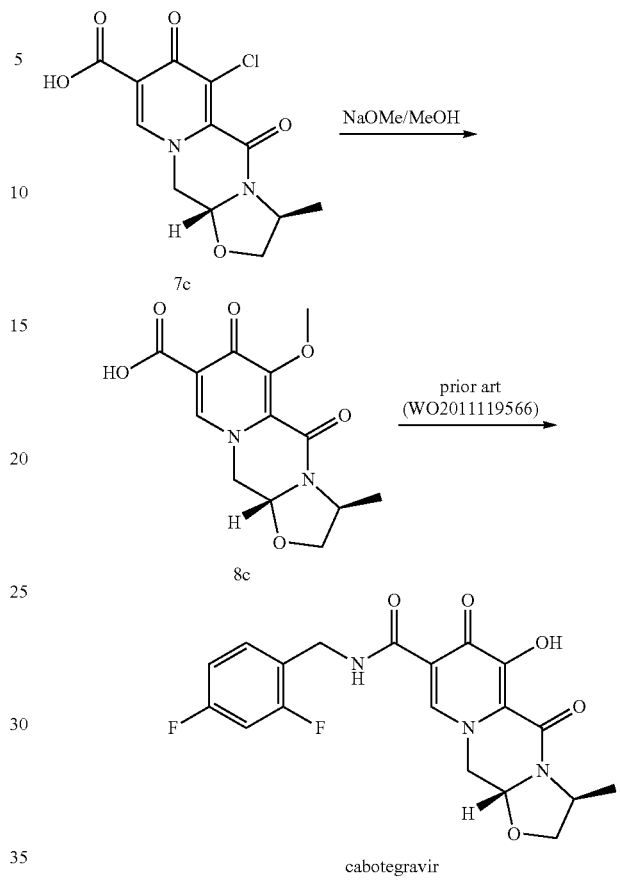

Favourably and suitably in the process of the invention a chlorination step can be combined with the enolic hydroxy group formation. Advantageously, there is flexibility as to when these steps can be combined in the overall synthetic schemes. That is the functionalization steps of chlorination and enolic hydroxy group formation can be neighbouring chemical reaction steps, but alternatively other synthetic step(s) can also lie in between these two steps. Therefore, in an embodiment the chlorination can be performed much earlier in the route of synthesis and the chlorine atom then substituted to the hydroxy group only several chemical steps later. One such example is the chlorination of the pyridone diester 9 to 10 which can be then transformed to the tricyclic ester 12, employing the deacetalization and cyclocondensation with (R)-3-aminobutanol methodology (see Scheme 4). This ester can then be hydrolysed under mild conditions to give 7 whose use in the synthesis of dolutegravir is shown in Scheme 3 and Scheme 4. Another early chlorination is represented by the deacetalysation and cyclocondensation of the pyridone diester 9 to 11 which can be then chlorinated to 12 (see Scheme 4). The ester 11 can also be prepared by esterifying 4. Scheme 4 shows an example of the pyridone functionalization principle by early chlorination and late hydroxylation.

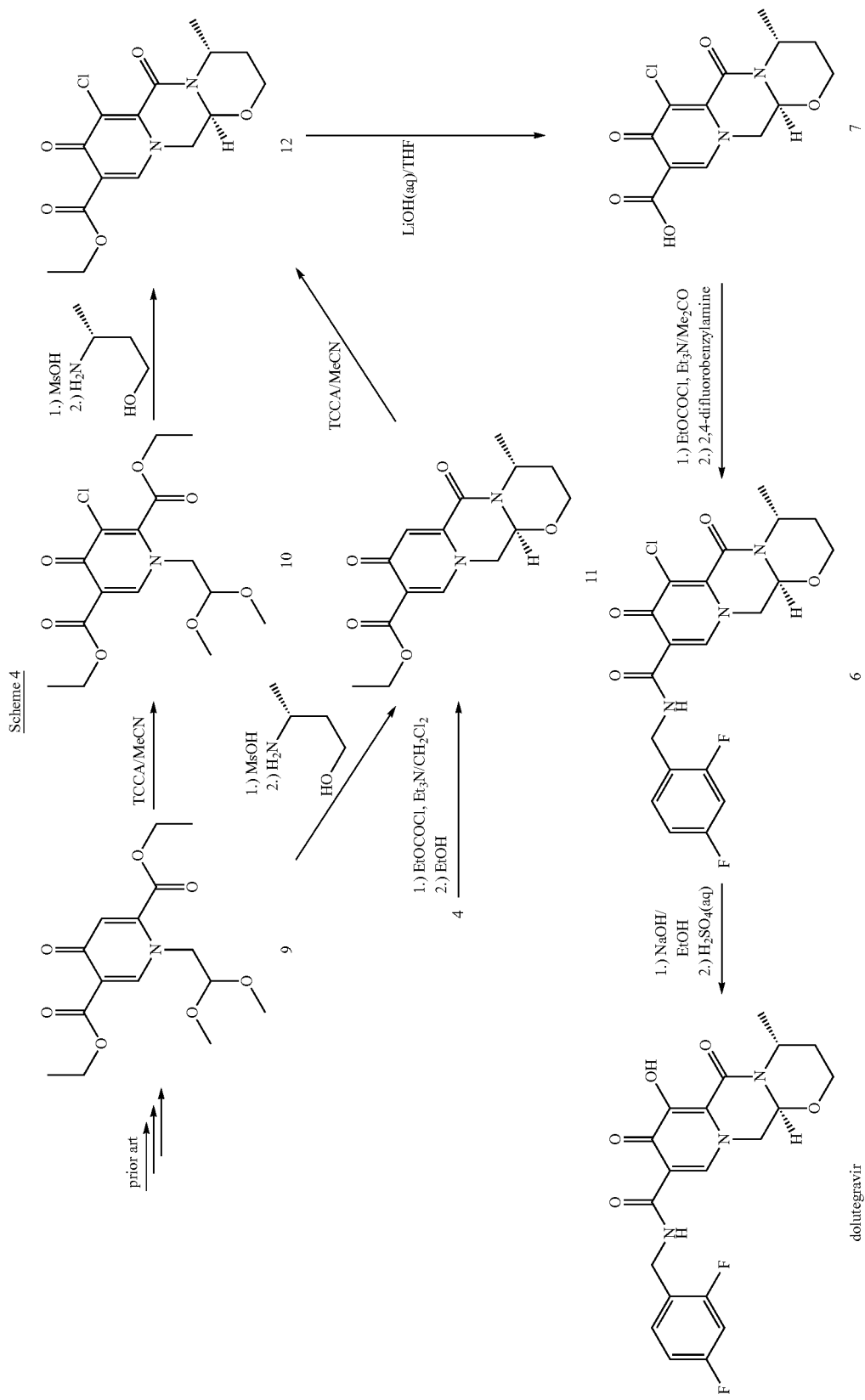

According to an embodiment of the process of the invention the building block 3-aminobutanol can suitably be substituted with other aminoalcohols to give dolutegravir analogues. For example, using (S)-alaninol gives cabotegravir as the final product. Similarly, using amines other than 2,4-difluorobenzylamine in the amidation step results in the synthesis of other dolutegravir analogues.

The starting pyridone diethyl ester 9 can be prepared by a modified 4-pyridone synthesis from ethyl acetoacetate and diethyl oxalate, but skipping the ester hydrolysis step (in analogy to Scheme 1).

An alternative way follows a prior art protocol as shown in Scheme C3. This synthetic scheme first employs the C-acylation of a suitable deprotonated enaminone followed by a condensation with ammonia or amines to finally yield a 4-pyridone. 4-Pyrones can also be prepared by such a C-acylation of enaminones followed by acidic reaction mixture treatment. The isolated 4-pyrones can then be transformed to the corresponding 4-pyridones in a separate step by the treatment with amines. Such approach is more suitable for pyridine dimethyl ester 22, which can be considerably hydrolysed to mono or diacid, if prepared according to Scheme 1. Both methods are useful in the synthesis of dolutegravir and its analogues. While pyridone diacids are superior for preparation of tricyclic intermediates, such as the compound 4, due to easy isolation and purification, pyridone diesters are more suitable than the corresponding pyridonecarboxylic acids when submitted to chlorination.

In the process according to the present invention 3 is favourably and preferably prepared from the inexpensive acetoacetate esters 13, which are first condensed to an enone intermediate 14 possessing a leaving group (see Scheme 5). Several reagents for introduction of a methine (=CH—) group can be used for this transformation, optionally resulting in different leaving groups (Lg) attached to the β position of the enone. The most practical reagent are N,N-dimethylformamide acetals, among which N,N-dimethylformamide dimethyl acetal (DMFDMA) which gives a N,N-dimethyl enaminone as the product (14, Lg=Me$_2$N) is commercially available in bulk industrial quantities.

Alternatively, orthoformate esters or their combination with urea can be used in order to prepare intermediates possessing other types of leaving groups (14, Lg=OR$^1$ or NHCONH$_2$ correspondingly). When using orthoformate esters, it is preferred to use formal derivatives of alcohols identical to the alcohols esterified in the acetoacetate starting material 13 (e.g., trimethyl ortoformate for methyl acetoacetate, etc.). This way suitably the transesterifications leading to a mixture of products can be avoided. On the other side, the acetal groups are stable against such substituent scrambling and therefore the R$^2$ groups can favourably be chosen independently of R$^1$ groups.

Other methine group generating reagents are selected from formic aminal esters (such as tert-butoxybis (dimethylamino)methane) or formimido esters (such as N,N,O-trimethylformiminium methyl sulfate—(Me$_2$N$^+$)=CH—OMe MeOSO$_2$O$^-$).

Advantageously the use of DMFDMA allows a one-pot transformation from the acetoacetate ester 13 to the intermediate 15 especially in the cases wherein the intermediate 15 is a crystalline solid, as in the case of R$^1$=R$^2$=Me. The steps from 15 to 17 can also preferably and most suitably be performed in a one-pot procedure. Even more, in many examples diacids of a general formula 17 are highly crystalline and easily isolable. In such examples, the whole sequence from 13 to 17 can also be performed as a one-pot reaction, which is particularly useful in cases where the intermediate 15 may not be easily isolated and purified, e.g. in some cases where alkyl groups R$^1$ and R$^2$ are not methyl or differ. Under favourable and suitable conditions no significant loss of yields and purity results despite the considerable length of such one-pot sequence(s). In this respect, the choice of the base, its excess and the solvent used in the cyclocondensation steps (16 from 15) can influence the reaction rate and yields. Sodium methylate (solid or methanolic solution) as the base and 2-propanol as the solvent were found to be particularly preferable in terms of efficiency, economy and material handling safety point of view. The hydrolysis of 16 to 17, going through the two possible monohydrolysed intermediates, can partially start already during the cyclocondensation with oxalate esters. This is presumably due to traces of water from the materials used. Nevertheless, alkali hydroxides or water with additional base are suitably and preferably provided to enable complete transformation. In a particularly preferred embodiment, when sodium methylate is used for the cyclocondensation, aqueous sodium hydroxide is used for the hydrolysis step. Depending on the reagents selection and the isolation protocol, the produced diacids 17 can be obtained either as pure compounds, or admixed with the oxalic acid byproduct. In the latter case, better yields can be obtained which is preferable, because the oxalic acid and lower assay of 17 do not affect the later transformations. Scheme 5 gives a representation of preferable chemical transformations involved in the synthesis of the 4-pyridone dicarboxylic acids.

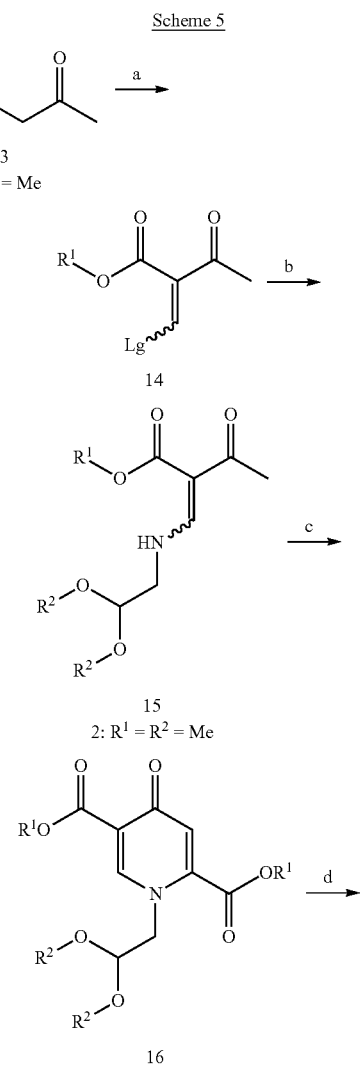

Scheme 5

-continued

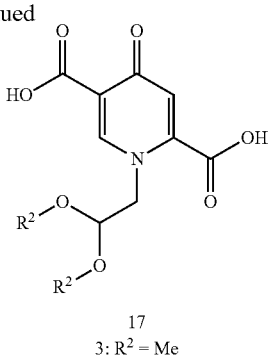

17
3: R² = Me conditions a:
(MeO)₂CHNMe₂ or Me₂N⁺=CH—OMe MeOSO₃⁻ (Lg = NMe₂);
or (R¹O)₃CH/(MeCO)₂O (Lg = OR¹);
or (R¹O)₃CH, CO(NH₂)₂/ROH (Lg = NHCONH₂)
conditions b: (R²O)₂CHCH₂NH₂/R¹OH
conditions c: (COOR¹)₂, base/solvent
conditions d: MOH/H₂O (M = Li, Na, K)
R¹ = Me, Et or other alkyl
R² = Me, Et, other alkyl, or optionally connected in a ring system It was surprisingly found that the pyridone diacids 16 can perform favourably well in a one-pot deacetalysation and cyclocondensation. The surprisingly good performance of the diacid 17 allows a complete hydrolysis of 16 and obviates the need for a more troublesome selective hydrolysis to a monoester. The complete hydrolysis results in yields higher than those obtainable from a selective hydrolysis because this can be difficult to control. Scheme 6 shows one-pot deacetalization and cyclocondensation reactions with its reaction intermediates.

A particular advantage of this embodiment is that the diacid 17 can suitably be used. By contrast, a diacid functionalized with an O-methyl protected hydroxy group on the pyridone 3-position can perform poorly when employed in a similar synthetic step. In this respect it was found that the reaction on 3-methoxy substituted diacid 20 gives less than 20% yields of an impure tricyclic product 8 (see Scheme 7). Many side products form during the reaction and the major characterized product is an elimination compound 21 resulting from the dehydration of the deacetalized reaction intermediate.

Scheme 7 shows a comparative attempt using a methoxy-substituted substrate in the deacetalization and cyclocondensation, wherein side products may form.

Scheme 7

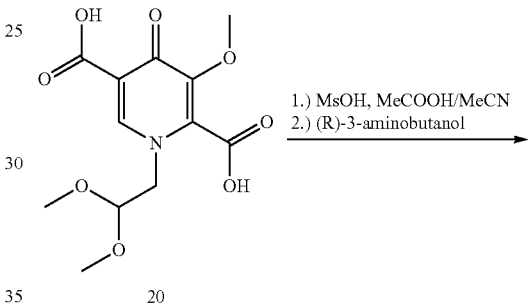

20

Scheme 6

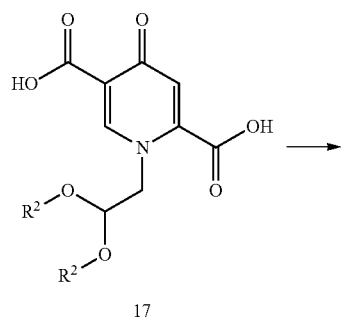

17

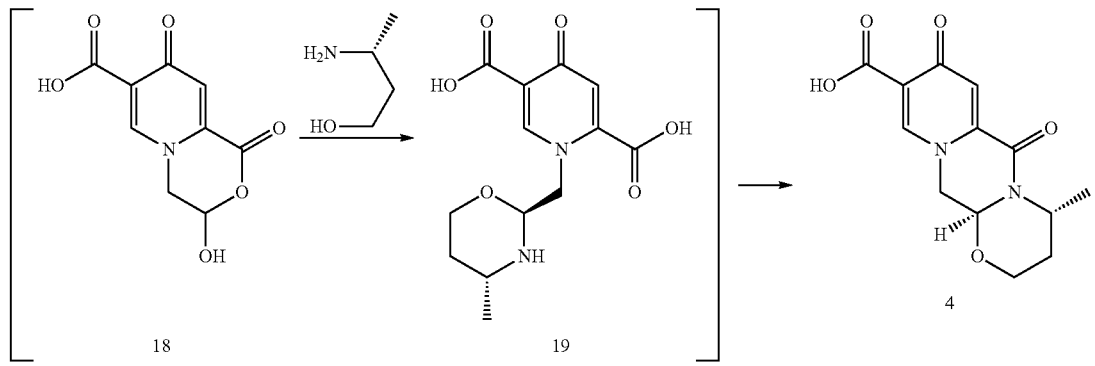

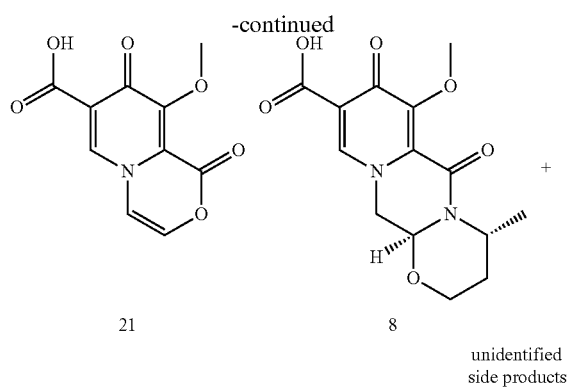

In a preferred embodiment, the intermediate 4 can be coupled with 2,4-difluorobenzylamine to give the amide 5. However, other amines can be used to give analogous amides. Typically and preferably for this transformation carboxylic acid activation is performed, which can generally be done using amidation coupling reagents. Simple activation reagents like carbonyldiimidazole (CDI), pivaloyl chloride or alkyl chloroformates can also be employed. The most preferred reagent is ethyl chloroformate in the presence of triethylamine which activates the carboxylic acids by mixed anhydride formation. In a particularly preferred embodiment, 4, triethylamine and ethyl chloroformate are combined in a suitable solvent and 2,4-difluorobenzylamine is added in one portion after a proper period of time, generally 3-15 min. When acetone is used as the solvent, the product can be obtained crystalline and of excellent purity by simply diluting the reaction mixture with water and filtering the white precipitate (see Scheme 8).

Catalytic amidation methods can also be applied. In particular, activation can also be performed by catalytic amounts of boric acids, e.g. phenylboronic acid, in refluxing solvents, e.g. toluene, with water removal using a Dean-Stark trap. Scheme 8 shows a typical amidation method for the synthesis of the amide 5.

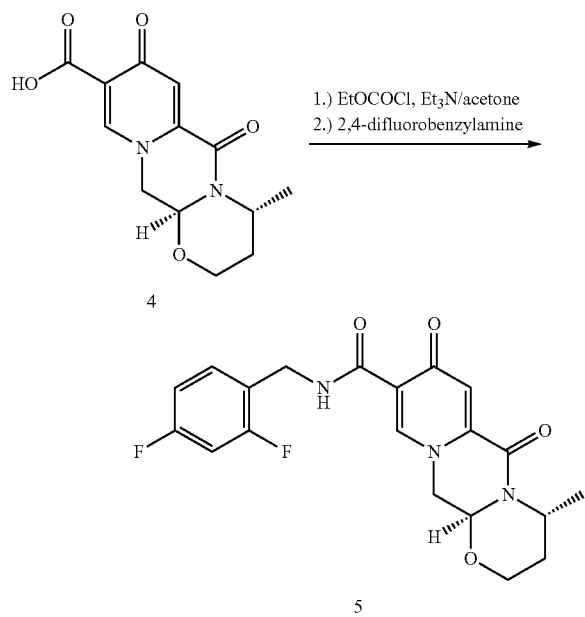

In the present invention it was recognized that particular attention has to be paid to the conversion step of halogenation, in particular chlorination of the pyridones, in particular 4, 4c, 5 and 5c. It was found that trichloroisocyanuric acid (TCCA) or alternatively 1,3-dichloro-5,5-dimethylhydantoin (DCDMH), preferably using acetonitrile or dichloromethane as solvent, can give useful and favorable results. Therefore, in a particularly preferred embodiment according to the invention, TCCA or DCDMH, more preferably TCCA in acetonitrile, is used for chlorination. Preferably the chlorinating reagent is used in excess, more preferably in several-fold excess, 2 to 3 times the stoichiometric amounts. It was surprisingly found that such chlorination is cheaper and easier applicable than bromination. Furthermore, bromination of 5 using reagents like 1,3-dibromo-5,5-dimethylhydantoin or N-bromosuccinimide did not proceed at all.

Scheme 9 shows chlorination of various intermediates. Depending on e.g. solubility and reactivity, e.g. in acetonitrile and specific structure, variations in obtainable yields may be observed. If desirable and suitable, reaction rate of the chlorination reaction may be increased by organocatalysis, e.g. on 4 chlorination, e.g. by using a 5 mol % of 1,4-diazabicyclo[2.2.2] octane (DABCO). Use of excess of TCCA can also be favorable in such cases. DABCO may also favorably influence reaction selectivity and/or the reaction pathway.

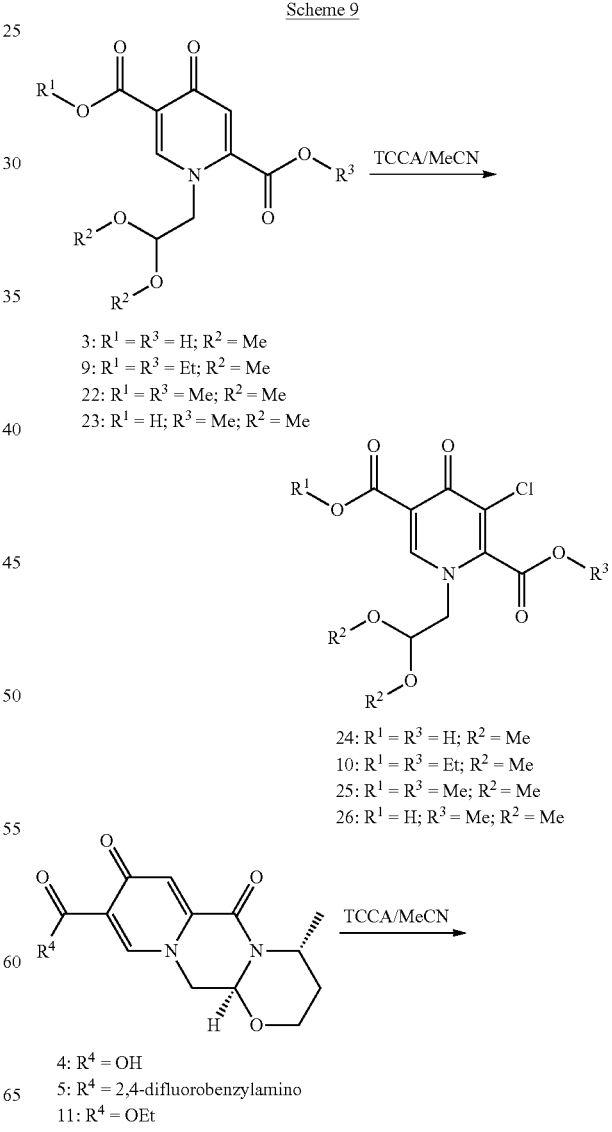

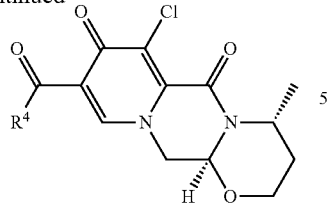

7: R⁴ = OH
6: R⁴ = 2,4-difluorobenzylamino
12: R⁴ = OEt

In a particularly preferred embodiment of the process of the invention, the substitution reaction of the chlorine atom to form an enolic hydroxy group is applied on the intermediate 6 to give dolutegravir. It was presently found that a simple direct nucleophilic substitution could not provide suitable results. For example, the use of aqueous hydroxide as a nucleophile in inert cosolvents like THF, DMSO, water, sulfolane, acetonitrile, DMF, or related polar aprotic solvents was attempted. Depending on the solvent used, either no significant reaction occurred, or complex mixtures containing only traces of dolutegravir resulted. Similarly, the chlorine in the compound 7 could also not be suitably substituted with a hydroxy group by heating in aqueous sodium hydroxide. Nevertheless and contrary to expectations, in the absence of any water, the reaction with a suspension of solid sodium hydroxide in some aprotic solvents where this hydroxide is not substantially soluble did provide useful conversions to dolutegravir. Best results were obtained in THF, acetonitrile and sulfolane, while DMF and DMSO gave inferior results.

Contrary to difficulties of a satisfactory substitution of chloro group to hydroxy, the substitution to an alkoxy group occurs in a facile manner. A treatment of the compound 6 with sodium methylate in methanol gave O-methyl dolutegravir (compound 27) and an analogous treatment of the compound 7 gave the corresponding analogue 8 (Scheme 10). For example, with 5 equivalents of sodium methylate in methanol, the reaction of 6 was completed in 4 h at 40° C. to give O-methyl dolutegravir which can be further demethylated to give dolutegravir. The demethylation can be performed by a known way, e.g. by cleavage with MgBr₂ or LiBr. Similarly, with 5 equivalents of sodium methylate in methanol, the reaction from 7 to 8 is completed in 24 h at 30° C.

Scheme 10

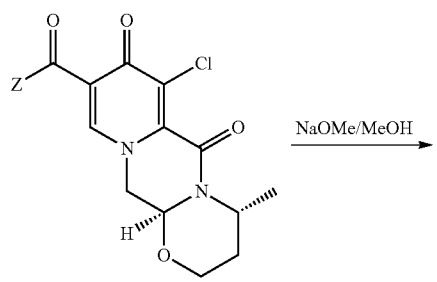

6: Z = 2,4-difluorobenzylamino
7: Z = OH

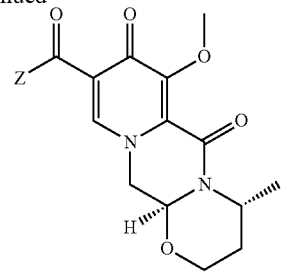

27: Z = 2,4-difluorobenzylamino
8: Z = OH

We have surprisingly found that by treating the compound 6 with sodium hydroxide in methanol dolutegravir is obtained. This discovery is in contradiction to the previously described of failure of direct substitution of chlorine with the hydroxy group. This fact can be explained that in spite of absence of methylate the transformation occurs via methoxy derivative 27. This surprising phenomenon was recognized by an online chromatographic method, which shows first a formation of compound 27 followed by formation of dolutegravir. Surprisingly, water added to the reaction mixture significantly inhibits the rate of this reaction.

According to an embodiment of the invention a compound of the formula (II-1)

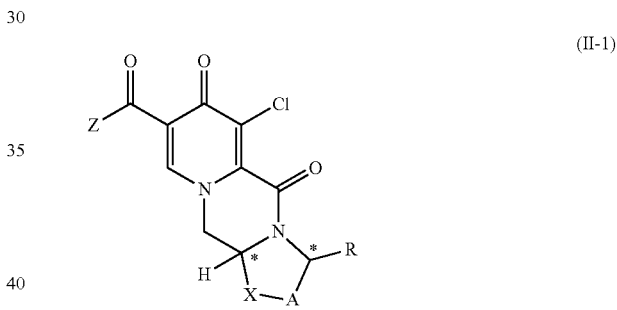

(II-1)

wherein
A represents $CH_2$ or $CH_2$—$CH_2$,
R represents H, $C_1$-$C_4$ alkyl or unsubstituted or substituted phenyl,
X represents O, S or N—$R^5$, wherein $R^5$ is H or $C_1$-$C_4$ alkyl,
Z represents hydroxy, $C_1$-$C_4$ alkoxy, phenoxy, benzoxy, —NH—Ar or —NH—$CH_2$—Ar, wherein
Ar represents unsubstituted or substituted phenyl, and
* represents a chirality center, which is of (R) or (S) configuration,
is treated by a hydroxide in a $C_1$-$C_4$ alcohol or mixture thereof.

Alcohols are selected from $C_1$-$C_4$ alcohols, preferably from lower primary alcohols while secondary and tertiary alcohols can also be used. Most preferably, ethanol is used, wherein the reaction proceeds faster than in methanol.

The hydroxide is a metal hydroxide, preferably an alkali metal hydroxide, more preferably is sodium hydroxide. Preferably, the alkali hydroxide in the solid state is used. Preferably, the hydroxide is used in a 1.2 to 10 molar excess, preferably in a 3 to 7 molar excess, most preferably in a 5 molar excess, according to the compound of formula (II-1).

Other bases that can suitably deprotonate alcohols and water can be used instead of hydroxides to form the alkoxide/hydroxide equilibrium needed for the reactions to proceed. Examples of such bases that a person skilled in the art can select include, but are not limited to, Na$_3$PO$_4$, K$_3$PO$_4$, K$_2$CO$_3$, 1,8-Diazabicycloundec-7-ene (DBU), and tetramethylguanidine (TMG).

The reaction time depends on the reaction temperature and on the excess of hydroxide. The preferable temperature range is from room temperature to 50° C. and preferable reaction time is up to 24 hours.

In even more preferred embodiment the water concentration in the reaction mixture is less than 30%, preferably less than 10%, more preferably less than 3%, even more preferably less than 1%. Most preferably the treatment is performed without addition of water.

Without any addition of water means that no potable, technological, demineralized or distilled water is added. It means also that the hydroxide is not used in aqueous solutions and those alcohols as solvents are not used in aqueous azeotropic mixtures (e.g. 96% ethanol) but in their commercial absolute grades. It also means that the only water in the mixture is entered by the inherent water of solid hydroxides. It is preferable to use sodium hydroxide which inherently contains less water than the more hygroscopic potassium hydroxide and less than the hydrate of lithium hydroxide.

According to a preferred embodiment of the invention the compound of formula (6) is transformed to dolutegravir by treating with a hydroxide in C$_1$-C$_4$-alcohol.

According to more preferred embodiment the compound of formula (6) is transformed to dolutegravir by treating with sodium hydroxide, preferably with sodium hydroxide in solid state, in methanol and/or ethanol. Preferably, the hydroxide is used in a 1.2 to 10 molar excess, preferably in a 3 to 7 molar excess, most preferably in a 5 molar excess, according to the compound of formula 6.

According to a particularly preferred embodiment the compound of formula (6) is transformed to dolutegravir by treating with sodium hydroxide, preferably with sodium hydroxide in solid state, in methanol and/or ethanol. Preferably, the hydroxide is used in in a 3 to 7 molar excess, most preferably in a 5 molar excess, according to the compound of formula 6. Preferably, the water concentration in the reaction mixture is less than 30%, preferably less than 10%, more preferably less than 3%, even more preferably less than 1%. Most preferably the transformation is performed in a non-aqueous medium.

In a special embodiment of the invention the chloro compound 6 is transformed to dolutegravir by treating with alkali metal hydroxide in C$_1$-C$_4$-alcohol. For example, the compound 6 is treated with 5 equivalents of sodium hydroxide in ethanol, no heating is required and the reaction was completed in less than 24 h at room temperature. The reaction monitoring showed a distinct stage, when dolutegravir alkyl ethers of formula (X) are initially formed by the reaction of 6 with the alcohol solvent. This ether is then dealkylated to give dolutegravir.

Dolutegravir, prepared by the procedure of the above embodiments can be isolated in the neutral form or in the salt form. If it is treated in situ by acidification with mineral or organic acids a precipitate of neutral dolutegravir is isolated. Suitable acids not limitedly include H$_2$SO$_4$, HCl, H$_3$PO$_4$, formic acid, acetic acid, oxalic acid, and citric acid. But because dolutegravir sodium salt is poorly soluble in alcohols it precipitates enabling a direct isolation from the reaction mixture by filtration.

Scheme 11 shows formation of dolutegravir sodium from the compound of formula 6 according to an embodiment of the invention. The process is very efficient, practical, and economical.

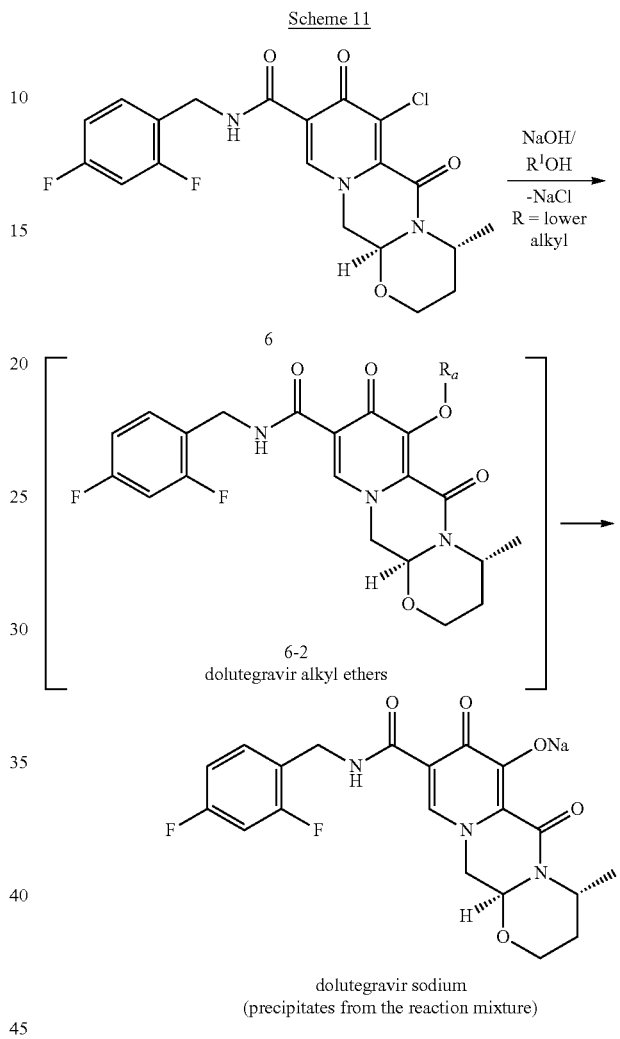

Scheme 11

6

6-2
dolutegravir alkyl ethers dolutegravir sodium
(precipitates from the reaction mixture)

By the analogues process the cabotegravir is prepared from the compound of formula 6c via the compound of formula 6c-2.

By contrast, the literature methods for the substitution of halogen atoms on the 3-position of the pyridones useful in the synthesis of dolutegravir are more cumbersome and/or less efficient, e.g. by treating 12 with potassium trimethylsilanolate in 1,2-dimethoxyethane. This can give labile silyl ether for whose cleavage already the reaction work up with 1M aqueous hydrochloric acid suffices. In this case the yields are poor to moderate and the reagent is expensive and has poor bulk availability. The method is therefore of limited industrial applicability.

In an alternative embodiment, this favorable functionalization principle of the invention can also be applied on the chlorocarboxylic acid intermediate of formula 7 to give the hydroxycarboxylic acid 28, which can then be further amidated to dolutegravir, e.g. using methods according to prior art. When using 5 equivalents of sodium hydroxide in ethanol, the formation of 28 is completed in 3 days at 50° C. Scheme 12 shows a synthesis of dolutegravir from 7.

Scheme 12

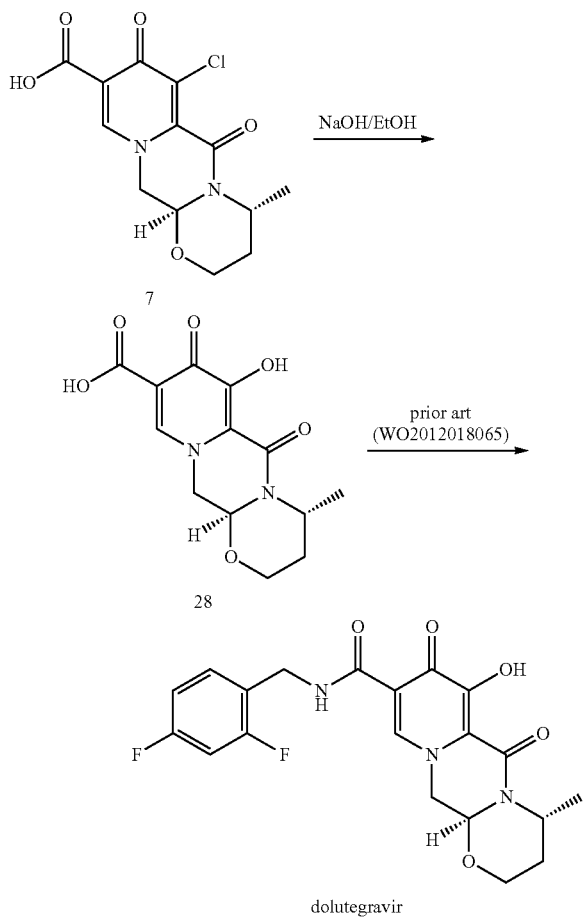

Furthermore this unexpected hydroxylation method in can be applied also on isolated pyridone alkyl ethers.

Thus, in another embodiment of the invention a compound according to the formula (II-2)

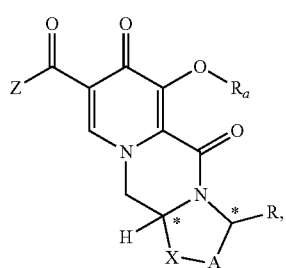

(II-2)

wherein
A represents $CH_2$ or $CH_2$—$CH_2$,
R represents H, $C_1$-$C_4$ alkyl or unsubstituted or substituted phenyl,
X represents O, S or N—$R^5$, wherein $R^5$ is H or $C_1$-$C_4$ alkyl,
Z represents hydroxy, $C_1$-$C_4$ alkoxy, phenoxy, benzoxy, —NH—Ar or —NH—$CH_2$—Ar, wherein
Ar represents unsubstituted or substituted phenyl, and
* represents a chirality center, which is of (R) or (S) configuration, $R_a$ represents $C_1$-$C_4$ alkyl or benzyl, preferably $C_1$-$C_4$ alkyl, more preferably ethyl or methyl,
is treated by a hydroxide to form a compound of formula (I).

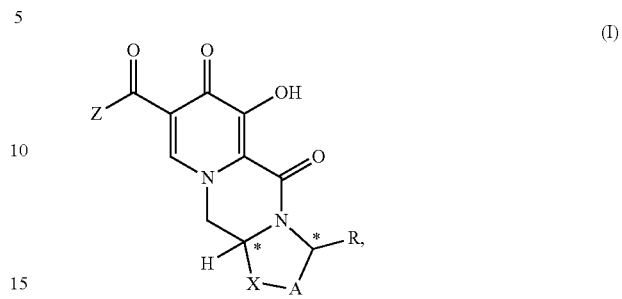

Use of alcohols selected from $C_1$-$C_4$-alcohols is preferred but not limited. In the absence of a need for chlorine substitution, there is also no need for the solvent to participate in the reaction, e.g. by forming an alkoxide. Indeed, it was observed that the dealkylation of dolutegravir ethers with hydroxides occurs also in inert aprotic solvents (e.g. in THF, acetonitrile, or sulfolan). Nevertheless, methanol and ethanol are the most preferred solvents.

The hydroxide is preferably selected from alkali metal hydroxide, the preferred hydroxide is sodium hydroxide. The alkali hydroxide is preferably used in a solid state. The hydroxide is preferably used in a 1.2 to 10 molar excess, preferably in a 3 to 7 molar, most preferably in a 5 molar excess, compared to the compound of formula (II-2).

Other bases that can suitably deprotonate alcohols and water can be used instead of hydroxides to form the alkoxide/hydroxide equilibrium needed for the reactions to proceed. Examples of such bases that a person skilled in the art can select include, but are not limited to, $Na_3PO_4$, $K_3PO_4$, $K_2CO_3$, 1,8-Diazabicycloundec-7-ene (DBU), and tetramethylguanidine (TMG). The reaction time depends on the reaction temperature and on the excess of hydroxide. The preferable temperature range is from room temperature to 50° C. and preferable reaction time is up to 24 hours.

Water does not have such negative effect on reaction as in case of chlorine substitution. However, it is preferred that the water concentration in the reaction mixture is less than 30%, preferably less than 10%, more preferably less than 3%, even more preferably less than 1%. Most preferably the transformation is performed in a non-aqueous medium.

Therefore, the present invention provides a process for the dealkylation of alkyl ethers of dolutegravir or its analogues. In a special embodiment of the invention the dolutegravir alkyl ethers of formula 6-2 are transformed to dolutegravir by treating with alkali metal hydroxide in an inert solvent.

Scheme 13 shows a favorable sodium hydroxide promoted dealkylation of dolutegravir ethers.

Scheme 13

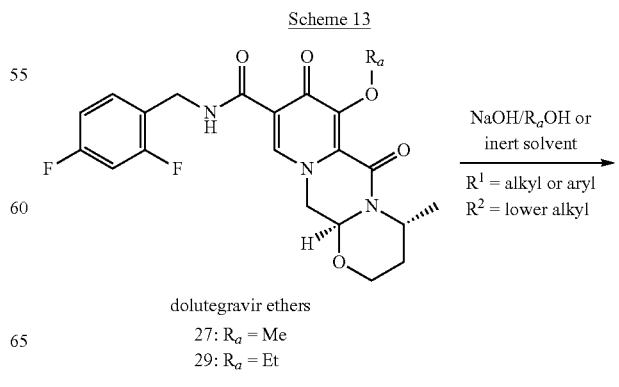

dolutegravir ethers
27: $R_a$ = Me
29: $R_a$ = Et

-continued

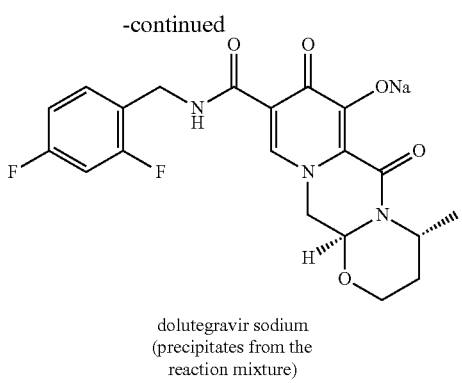

dolutegravir sodium
(precipitates from the
reaction mixture)

The new method of deprotection of dolutegravir ethers and cabotegravir ethers according to the invention can be applied also in substrates which are prepared by various synthetic methods. This dealkylation method is broadly applicable and may be useful for any alkoxy or any aryloxy substituent, thus enabling the use of a variety of other hydroxy protecting groups.

According to a preferred embodiment of the invention the compound of formula 6-2 is transformed to dolutegravir by treating with a hydroxide in $C_1$-$C_4$-alcohol.

According to more preferred embodiment the compound of formula 6-2 is transformed to dolutegravir by treating with sodium hydroxide, preferably with sodium hydroxide in solid state, in a $C_1$-$C_4$-alcohol, preferably primary $C_1$-$C_4$-alcohol, more preferably in methanol and/or ethanol. Preferably, the hydroxide is used in a 1.2 to 10 molar excess, preferably in a 3 to 7 molar excess, most preferably in a 5 molar excess, according to the compound of formula 6-2.

According to a particularly preferred embodiment the compound of formula 6-2 is transformed to dolutegravir by treating with sodium hydroxide, preferably with sodium hydroxide in solid state, in methanol and/or ethanol. Preferably, the hydroxide is used in in a 3 to 7 molar excess, most preferably in a 5 molar excess, according to the compound of formula 6. Preferably, the water concentration in the reaction mixture is less than 30%, preferably less than 10%, more preferably less than 3%, even more preferably less than 1%. Most preferably the transformation is performed in a non-aqueous medium.

Dolutegravir, prepared by the procedure of the above embodiments can be isolated in the neutral form or in the salt form as described above.

By the analogues process the cabotegravir alkyl ethers of formula 6c-2 are transformed to cabotegravir by treating with alkali metal hydroxide in an inert solvent.

Cabotegravir, prepared by the procedure of the above embodiments can be isolated in the neutral form or in the salt form as described above.

Furthermore, according to the present method a simple dealkylation of dolutegravir ethers of formula 6-2 with sodium hydroxide can be applied to give directly the dolutegravir sodium salt in a more practical and more general method. For example, heating methyl dolutegravir ether (27) with sodium hydroxide in methanol gives the dolutegravir sodium salt. Similarly, 27 can be completely transformed to dolutegravir sodium salt with sodium hydroxide in ethanol after a few hours at 25-50° C. (see Scheme 13). During the reaction in ethanol, the intermediate appearance of the ethyl ether 29 from the starting methyl ether is observable.

The hydroxide based dealkylation is independent of the nature of the substituent on the position 9 of the tricyclic system (4-pyridone position 5). It readily occurs even in the absence of the carbonyl substituents. For example, the plain benzyl protected tricycle 30 can be debenzylated with sodium hydroxide in ethanol at 50° C. to give the deprotected tricycle 32 and benzyl alcohol as the byproduct. Performing the reaction at room temperature enables the isolation of the ethyl ether 31 intermediate in good yields. Scheme 14 shows a favorable sodium hydroxide promoted dealkylation of a benzyl ether.

Scheme 14

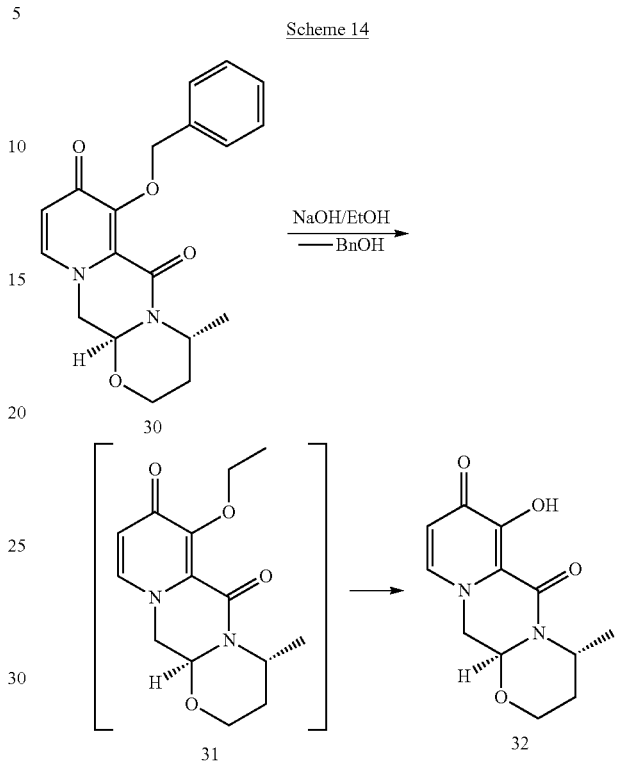

The process of the invention provides a new and efficient route of synthesis for dolutegravir. In an embodiment the pyridone core can be functionalized by the introduction of the enolic hydroxyl group at a late stage. Functionalizing of the pyridine core with hydroxy can be performed in a facile and efficient process, in particular using an efficient substitution of chloro to hydroxy by use of alcoholic hydroxides. Moreover, efficient chlorination can be achieved with N-chlorosubstituted cyclic ureas (e.g. TCCA, N-chlorohydantoins). However, variations in the order of functionalization are also possible, while maintaining the overall principles for the functionalization, i.e. the efficient introduction of adequate groups, in particular in the 7-position and the 9-position. The route of synthesis, and its variations, is particularly suitable for use in preparing dolutegravir because the intermediates are crystalline solids that can be easily purified. Due to the feasibility of merging several chemical steps in one-pot transformations, dolutegravir can be manufactured in 5 to 6 process steps. The possibility to combine several steps in one-pot process step(s) or telescoping can provide for a convenient and short industrial process. The route of synthesis can be applied also for developing manufacturing processes of dolutegravir analogues.

Advantageously purification can be efficiently performed because of the crystalline nature of the intermediates with higher potential of reducing impurities compared to situations where liquid intermediates are present. Thus, dolutegravir may be prepared with exceptional purity, e.g. with all impurities lying below 0.1%. In overall process inexpensive starting materials can favourably be used, e.g. methyl acetoacetate and the use of toxic and expensive reagents can advantageously be avoided. Favorably, either the sodium salt of dolutegravir can be obtained directly or it can be converted to the free dolutegravir, e.g. by acidification with an aqueous acid during reaction work-up.

EXAMPLES

The following examples are merely illustrative of the present invention and they should not be considered as limiting the scope of the invention in any way. The examples and modifications or other equivalents thereof will become apparent to those versed in the art in the light of the present entire disclosure. Particularly, all Examples related to the preparation of dolutegravir and intermediates thereof can be used by the analogy for the preparation of cabotegravir and intermediates thereof.

Example 1

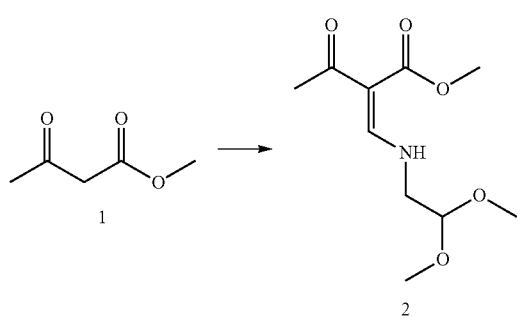

Methyl acetoacetate (1, 25.22 g) and dimethylformamide dimethyl acetal (DMFDMA, 35 mL) was heated at 50-55° C. for 2 h, then methanol (60 mL), aminoacetaldehyde dimethyl acetal (24 mL) and acetic acid (4 mL) was added an the mixture was heated under reflux for one hour, then concentrated. MTBE (100 mL) was added and the mixture was kept at 5° C. overnight to crystallize. Upon filtration 46 g (92%) of product 2 was recovered.

$^1$H NMR (DMSO-d$_6$): δ 2.31 (s, 3H), 3.30 (s, 6H), 3.49 (m, 2H), 3.61 (s, 3H), 4.43 (m, 1H), 8.02 (d, 1H), 10.8 (bs, 1H). $^{13}$C NMR (DMSO-d$_6$): δ 30.52, 35.48, 50.53, 54.23, 98.99, 102.47, 160.70, 166.92, 197.21.

Example 2

Compound 2 (5.00 g) was dissolved in 2-propanol, dimethyl oxalate (7.02 g) was added and heated to 40° C. Sodium methylate (25% in methanol; 20 mL) was slowly (10 min) added, the mixture was then heated to 50-55° C. and stirred at that temperature for 2-2.5 h. The mixture was cooled to ambient temperature, then sodium hydroxide solution (1M, 65 mL) was added to the mixture and stirred for another 2 h, followed by addition of concentrated hydrochloric acid (11 mL) and stirred for another 2 h. The precipitate was filtered and dried to give 8.08 g (NMR assay 47%; 65% yield) of compound 3.

$^1$H NMR (DMSO-d$_6$): δ 2.50 (m, 2H), 3.30 (s. 6H), 4.49 (m, 1H), 7.06 (s, 1H); 8.70 (s, 1H). $^{13}$C NMR (DMSO-d$_6$): δ 55.23, 55.37, 102.34, 115.47, 120.24, 145.17, 162.71, 165.22, 178.55.

Example 3

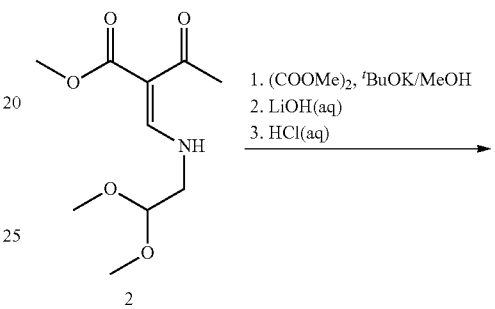

1. (COOMe)$_2$, $^t$BuOK/MeOH
2. LiOH(aq)
3. HCl(aq)

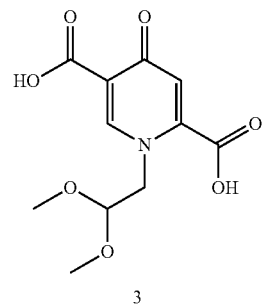

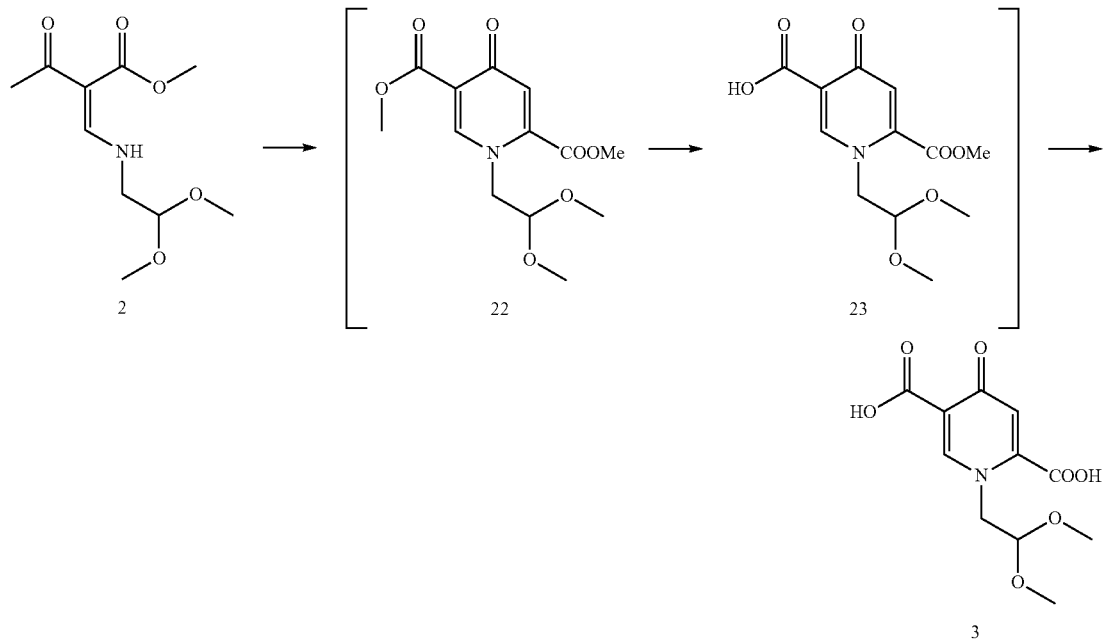

Compound 2 (158.37 g) was dissolved in methanol (548 mL), followed by the addition of dimethyl oxalate (202.2 g). While keeping the temperature below 30° C., potassium tert-butoxide (192.1 g) was added and reaction mixture was heated at 50° C. overnight. The suspension was then filtered and the filter cake washed with methanol. The filtrate was concentrated (approximately to 680 mL), then water (680 mL) was added, followed by addition of lithium hydroxide hydrate (143.7 g) while keeping the temperature below 40° C. The suspension was then stirred at ambient temperature overnight and filtered. To the obtained filtrate, concentrated hydrochloric acid (339 mL) was added while keeping the temperature below 30° C. The suspension was aged for 2 h and filtered to give 4 as a white powder (95.6 g, NMR assay 100%; 52% yield).

Example 4

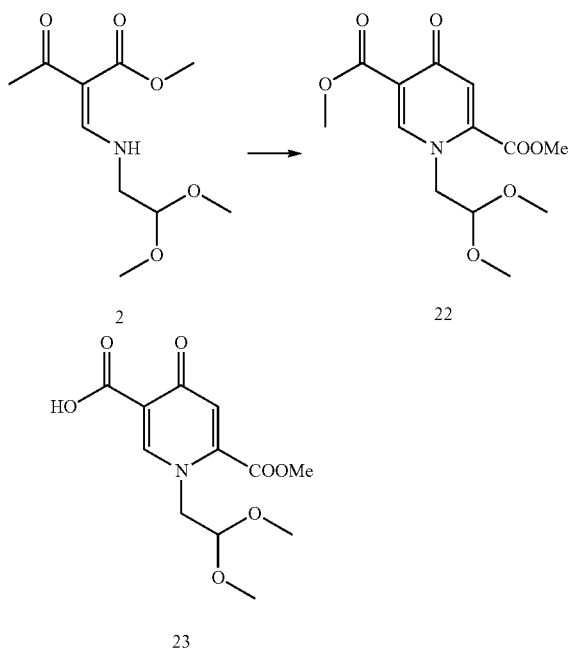

Compound 2 (5.00 g) was dissolved in 2-propanol, dimethyl oxalate (7.02 g) was added and heated to 40° C. Sodium methylate (25% in methanol; 15 mL) was slowly (10 min) added then the mixture was heated to 50-55° C. and stirred at that temperature for 72 h. The mixture was concentrated and components were separated by flash column chromatography (ethyl acetate/methanol 9:1 to 6:4). Early fractions gave compound 22 upon concentration, late fractions gave compound 23.

Compound 22: $^1$H NMR (DMSO-$d_6$): δ 2.49 (m, 2H), 3.28 (s, 6H), 3.73 (s, 3H), 3.85 (s, 3H), 4.41 (m, 1H), 4.50 (m, 1H), 6.65 (s, 1H), 8.36 (s, 1H). $^{13}$C NMR (DMSO-$d_6$): δ 51.63, 53.36, 54.25, 55.47, 102.71, 118.24, 123.60, 140.81, 150.21, 162.44, 164.49, 173.43.

Compound 23: $^1$H NMR (DMSO-$d_6$): δ 2.49 (m, 2H), 3.26 (s, 6H); 3.70 (s, 3H); 4.33 (d, 1H); 4.60 (m, 1H), 6.19 (s, 1H), 8.12 (s, 1H). $^{13}$C NMR (DMSO-$d_6$): δ 50.03, 51.34, 54.59, 54.85, 102.91, 116.04, 118.19, 148.32, 152.12, 163.46, 165.24, 174.99

Example 5

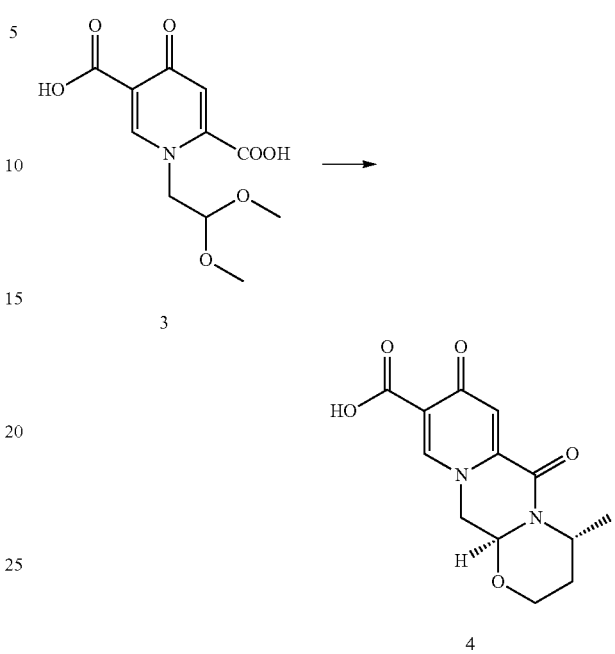

Compound 3 (5.5 g; assay 53%) was suspended in acetonitrile, acetic acid (6 mL) and methanesulfonic acid (2.5 mL) were added followed by the heating of mixture to 70° C. for 4 h. The suspension was filtered and filtrate cooled to ambient temperature. Triethylamine (6.6 mL) and (R)-3-amino-butan-1-ol (1.24 mL) was added followed by heating the mixture at reflux temperature for 20-24 h. The mixture was filtered, filtrate concentrated and 1M HCl (100 mL) was added, followed by extraction with dichloromethane (3×50 mL). Combined organic fractions were concentrated, 2-propanol was added (10 mL) and suspension was stirred at 70-80° C. for 10 min, left to cool to ambient temperature then filtered to give 2.19 g of compound 4 (73%).

$^1$H NMR (DMSO-$d_6$): δ 1.31 (d, 3H), 1.52 (m, 1H), 1.97 (m, 1H), 3.89 (m, 1H), 4.01 (m, 1H), 4.46 (m, 1H), 4.64 (m, 1H), 4.78 (m, 1H), 5.50 (m, 1H), 7.29 (s, 1H), 8.88 (s, 1H), 15.83 (s, 1H).

$^{13}$C NMR (DMSO-$d_6$): δ 15.22, 29.14, 45.26, 51.13, 62.09, 76.03, 116.31, 118.79, 140.53, 146.79, 155.36, 165.24, 178.75.

Example 6

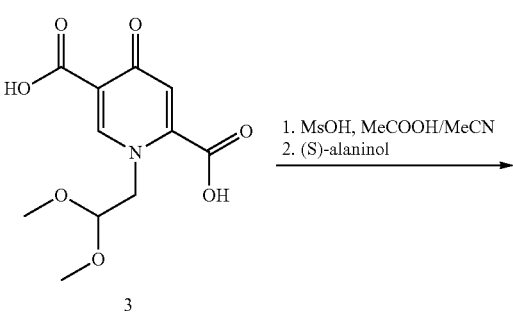

5.00 (m, 1H), 5.27 (m, 1H), 6.80 (m 2H), 7.33 (m, 2H), 8.49 (s, 1H), 10.48 (s, 1H). $^{13}$C NMR (CDCl$_3$): 15.50, 29.22, 36.43, 45.19, 51.83, 62.79, 103.71, 103.91, 111.0, 111.18, 120.59, 123.04, 130.40, 137.41, 144.58, 156.27, 163.87, 177.83.

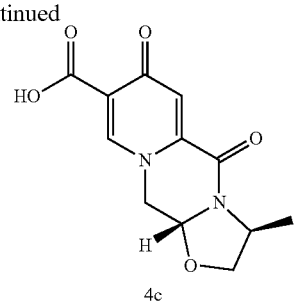

4c

Compound 3 (14.55 g; assay 49%) was suspended in acetonitrile (125 mL), acetic acid (15 mL) and methanesulfonic acid (6.25 mL) were added followed by the heating of mixture to 70° C. for 4 h. The suspension was filtered and filtrate cooled to ambient temperature. Triethylamine (16.5 mL) and (S)-2-aminopropanol (2.45 mL) was added followed by heating the mixture at reflux temperature for 24 h. The insoluble product was filtered, washed with 2-propanol (20 mL) and dried to give (3S,11aR)-3-methyl-5,7-dioxo-2,3,5,7,11,11a-hexahydrooxazolo[3,2-a]pyrido[1,2-d]pyrazine-8-carboxylic acid (5.2 g, 75%).

$^1$H NMR (DMSO-d$_6$): δ 1.31 (d, J=6.3 Hz, 3H), 3.65 (dd, J=8.6, 6.8 Hz, 1H), 4.13 (dd, J=11.7, 10.3 Hz, 1H), 4.28 (m, 1H), 4.39 (dd, J=8.6, 6.8 Hz, 1H), 4.92 (dd, J=12.3, 4.2 Hz, 1H), 5.45 (dd, J=10.2, 4.1 Hz, 1H), 7.16 (s, 1H), 8.84 (s, 1H), 15.74 (s, 1H).

Example 7

Example 8

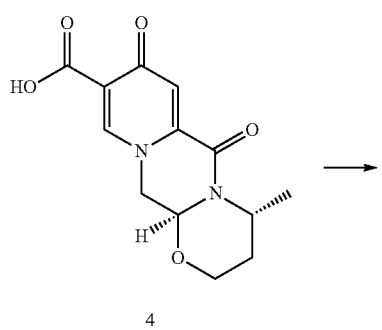

4

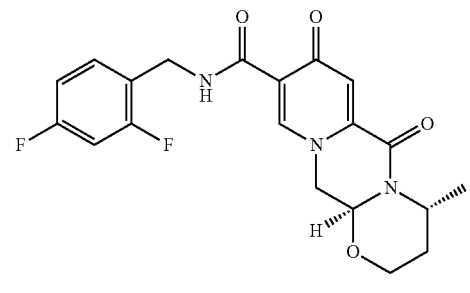

5

To a suspension of 4 (2.84 g, 10 mmol) in a mixture of triethylamine (2.24 mL, 16 mmol) and acetone (50 mL) stirring on an ice bath was added ethyl chloroformate (1.20 mL, 12 mmol). After stirring for 10 min, 2,4-difluorobenzylamine (1.21 mL, 10 mmol) was added and the mixture left stirring at room temperature for 1 h. The product was isolated by slowly diluting the reaction mixture with water (50 mL), partial concentration, filtration, washing with water (2×50 mL) and drying. There was obtained 5 as a white powder (3.48 g, 86%): mp 181.0-184.7° C. $^1$H NMR (DMSO-d$_6$): δ 1.29 (d, J=7.0 Hz, 3H), 1.56 (dd, J=13.9, 2.0 Hz, 1H), 1.93-2.06 (m, 1H), 3.90 (ddd, J=11.6, 5.0, 2.1 Hz, 1H), 3.98 (td, J=12.0, 2.2 Hz, 1H), 4.45 (dd, J=13.6, 6.6 Hz, 1H), 4.72 (dd, J=13.6, 3.8 Hz, 1H), 4.74-4.81 (m, 1H), 5.44 (dd, J=6.6, 3.8 Hz, 1H), 8.93 (s, 1H), 15.14 (s, 1H). $^{13}$C NMR (DMSO-d$_6$): δ 15.78, 29.13, 44.89, 52.88, 61.63, 75.61, 113.54, 128.49, 136.42, 145.64, 154.62, 164.58, 174.58

Example 9

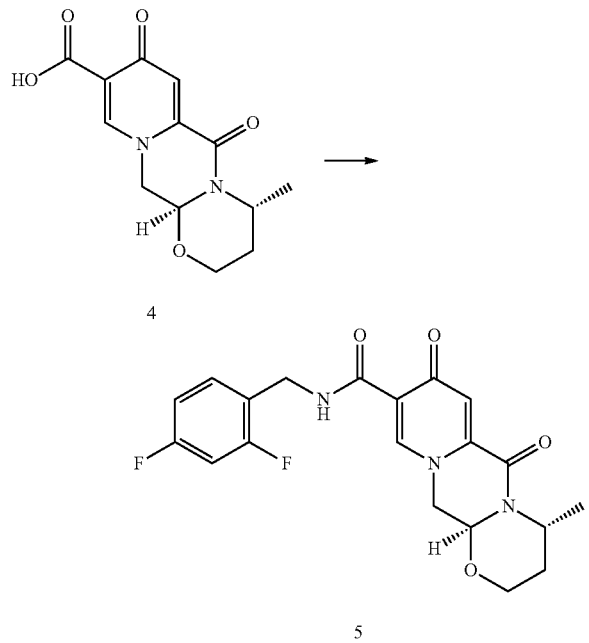

4
5

Compound 4 (0.63 g) was dissolved in dichloromethane (15 mL), cooled to 5° C., then triethylamine (0.31 mL) was added, followed by ethyl chloroformate (0.26 mL), followed by slow (30 min) addition of 2,4-difluorobenzylamine. The mixture was then stirred at ambient temperature for 24 h. Water (10 mL) was added, organic phase was separated and washed with 1M HCl (15 mL) and water (15 mL), concentrated and treated with 2-propanol to give the product 5 in a quantitative yield.

$^1$H NMR (CDCl$_3$): δ 1.39 (d, 3H), 1.52 (s, 1H), 2.19 (m, 1H), 4.00 (m, 2H), 4.16 (m, 1H), 4.31 (m, 1H), 4.62 (d, 2H),

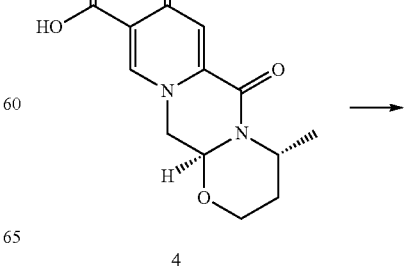

4

-continued

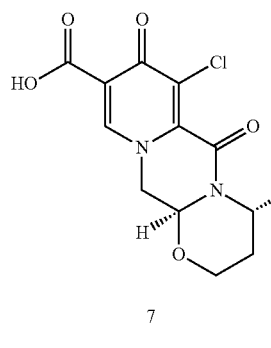

7

To a suspension of 4 (11.36 g, 40 mmol) in acetonitrile (80 mL) stirring at room temperature was added TCCA (9.29 g, 38 mmol) and DABCO (0.23 g, 5 mol %). After stirring at room temperature for 1 h, the reaction was quenched with a mixture of DMSO (5.26 mL) and water (1.33 mL). The insoluble cyanuric acid was removed by filtration and the filtrate evaporated under reduced pressure to give viscous oil. This was triturated in methanol (20 mL) to induce crystallization. The product was filtered, washed with cold methanol (10 mL) and dried to give 7 as a yellowish powder (5.13 g, 41%): mp 191.3-198.7° C.

Example 10

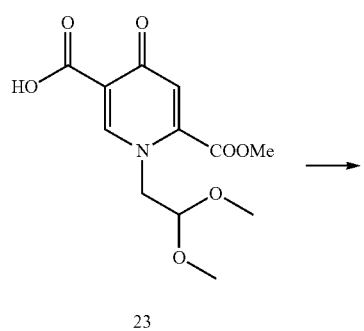

23

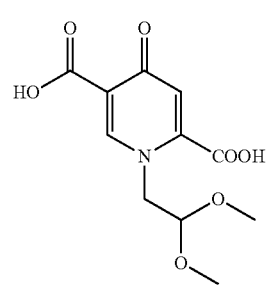

3

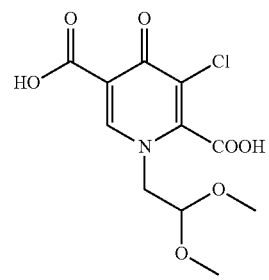

24

Attempted chlorination of 23: Compound 23 (0.54 g) was suspended in acetonitrile (10 mL) and trichlorocyanuric acid (0.44 g) was added and the solution was stirred at ambient temperature overnight. Precipitate was filtered. Only traces of a product corresponding to the compound 26 could be detected in the reaction mixture by LC-MS analysis. Conversion did not improve with time.

Example 11

Attempted chlorination of 3: Compound 3 (0.30 g) was suspended in acetonitrile (5 mL) and trichlorocyanuric acid (0.13 g) was added. The suspension was stirred at ambient temperature overnight. Only traces of a product corresponding to the compound 24 could be detected in the reaction mixture by LC-MS analysis.

Example 12

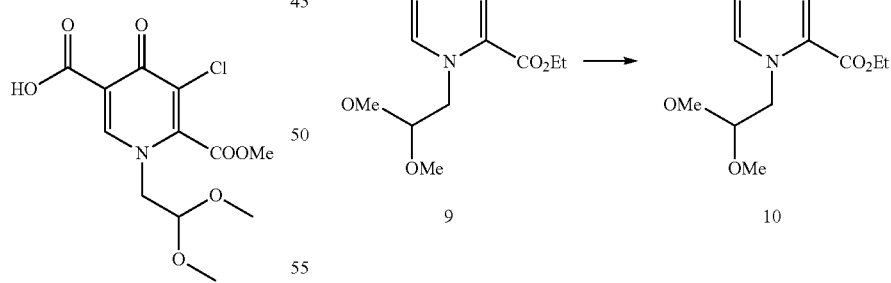

9                    10

Trichloroisocyanuric acid (0.23 g) was added in a single portion to a stirred solution of the diethyl 1-(2,2-dimethoxyethyl)-4-oxo-1,4-dihydropyridine-2,5-dicarboxylate (9, 0.66 g) in dry acetonitrile (4 mL) at room temperature. The resulting suspension was stirred at room temperature for ca. 24 h. The reaction mixture was diluted with dichloromethane and filtrated. The filtrate was then concentrated in vacuo to afford crude oil (0.86 g). Purification by flash chromatography (eluting ethyl acetate/cyclohexane) furnished diethyl 3-chloro-1-(2,2-dimethoxyethyl)-4-oxo-1,4-dihydropyridine-2,5-dicarboxylate, 10 as a yellow semi-solid (0.38 g).

¹H NMR (CDCl₃): δ 1.28 (t, J=7.1 Hz, 3H), 1.37 (t, J=7.2 Hz, 3H), 3.35 (s, 6H), 3.89 (d, J=5.0 Hz, 2H), 4.27 (q, J=7.1 Hz, 2H), 4.43 (q, J=7.1 Hz, 2H), 4.48 (t, J=4.9 Hz, 1H), 8.15 (s, 1H).

¹³C NMR (CDCl₃): δ 13.83, 14.13, 55.82, 57.09, 61.41, 63.72, 102.52, 117.35, 126.90, 140.22, 146.92, 160.67, 164.13, 168.95.

Example 13

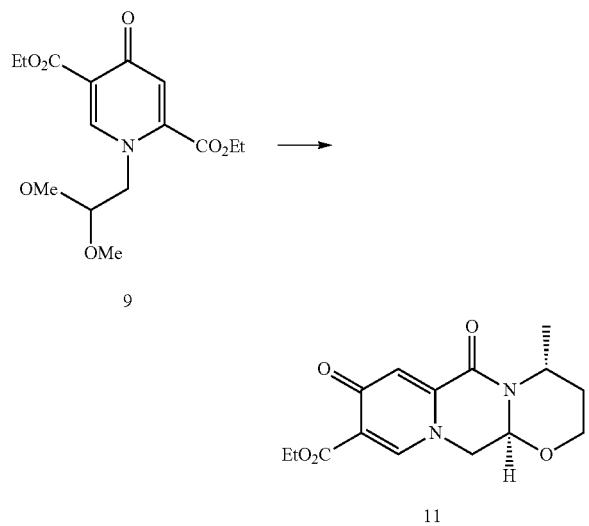

Diethyl 1-(2,2-dimethoxyethyl)-4-oxo-1,4-dihydropyridine-2,5-dicarboxylate (9, 0.64 g) was dissolved in anhydrous acetonitrile (6 mL) and treated sequentially with acetic acid (560 µL) and methanesulfonic acid (40 µL). The resulting mixture was heated to 62° C. and stirred for 4 h and more methanesulfonic acid (40 µL) was added. After additional 2 h, more methanesulfonic acid (80 µL) was added. This was repeated after additional 2 h, when more methanesulfonic acid (80 µL) was added. The reaction mixture was stirred additional 17 h at 62° C. then was treated with a mixture of (R)-3-aminobutanol (0.22 g), triethylamine (0.5 mL) and acetonitrile (0.7 mL). The reaction mixture was stirred additional 22 h at 62° C. and then concentrated in vacuo. The crude material was partitioned between dichloromethane and 1M HCl solution (15 mL). The combined organic phases were dried (Na₂SO₄), filtered and concentrated in vacuo to afford the crude (4R,12aS)-ethyl 4-methyl-6,8-dioxo-3,4,6,8,12,12a-hexahydro-2H-pyrido[1',2':4,5]pyrazino[2,1-b][1,3]oxazine-9-carboxylate (11) as a brownish oil (0.61 g).

¹H NMR (CD₃OD): δ 8.44 (s, 1H), 7.16 (m, 1H), 5.48 (t, J=4.8 Hz, 1H), 4.86 (m, 1H), 4.49 (dd, J=13.6, 4.0 Hz, 1H), 4.30-4.25 (m, 3H), 4.09 (dt, J=12.1, 2.3 Hz, 1H), 3.96 (ddd, J=11.7, 5.0, 2.1 Hz, 1H), 2.18-2.10 (m, 1H), 1.60-1.56 (m, 1H) 1.39 (d, J=7.1 Hz, 3H), 1.33 (t, J=7.1 Hz, 3H).

¹³C NMR (CDCl₃): δ 8.45, 14.08, 15.39, 29.17, 45.04, 45.72, 51.56, 60.86, 62.61, 76.33, 119.54, 123.72, 136.96, 145.67, 156.26, 163.68, 175.43

Example 14

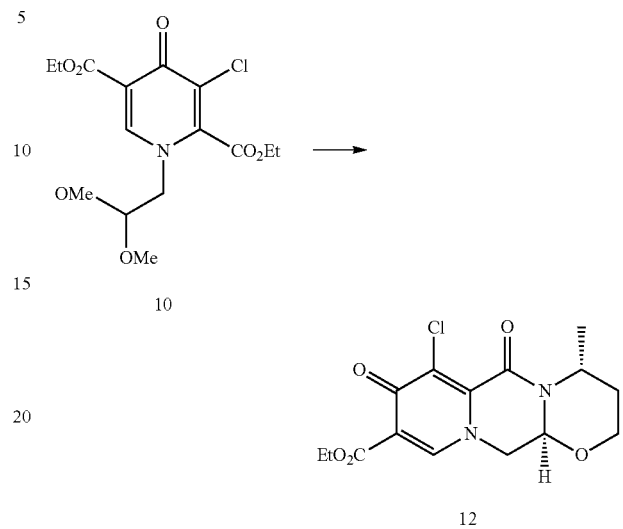

Diethyl 3-chloro-1-(2,2-dimethoxyethyl)-4-oxo-1,4-dihydropyridine-2,5-dicarboxylate (10, 1.23 g) was dissolved in 85% formic acid (25 mL) at room temperature. The mixture was warmed to 40° C. and stirred for 23 h. The reaction mixture was concentrated in vacuo, and then partitioned between dichloromethane and aqueous NaHCO₃ solution. The combined organic phases were dried (Na₂SO₄), filtered and concentrated in vacuo to afford brownish oil (0.49 g). The crude oil was dissolved in anhydrous toluene (5 mL) and treated sequentially with (R)-3-aminobutanol (0.19 g), methanol (0.2 mL) and acetic acid (96 µL). The resulting mixture was heated to 90° C. and stirred for 20 h. The reaction mixture was cooled to room temperature and then partitioned between dichloromethane and aqueous NaHCO₃ solution. The combined organic phases were dried (Na₂SO₄), filtered and concentrated in vacuo to afford the crude (4R,12aS)-Ethyl 7-chloro-4-methyl-6,8-dioxo-3,4,6,8,12,12a-hexahydro-2H-pyrido[1',2':4,5]pyrazino[2,1-b][1,3]oxazine-9-carboxylate (12) as a brownish oil (0.24 g).

Example 15

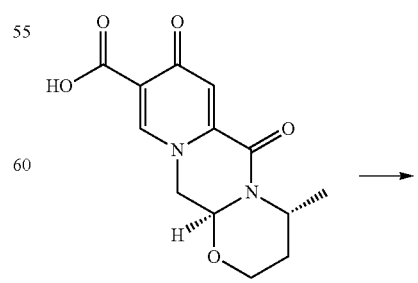

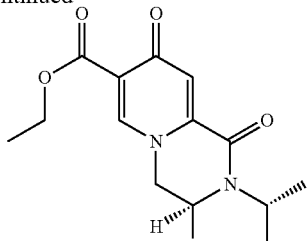

11

To a solution of 4 (5.68 g, 20 mmol) in dichloromethane (50 mL) stirring in an ice bath was added triethylamine (5.6 mL, 40 mmol), followed by ethyl chloroformate (2.61 mL, 26 mmol). After 20 min, ethanol (50 mL) was added. The mixture was then left stirring 24 h at room temperature and concentrated under reduced pressure. The residue was triturated in acetone (80 mL). The insoluble salt (triethylamine hydrochloride) was removed by filtration. The filtrate was evaporated under reduced pressure to give 11 as an amorphous solid in a quantitative yield (6.1 g).

Example 16

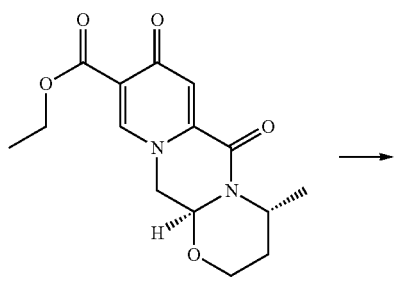

11

→

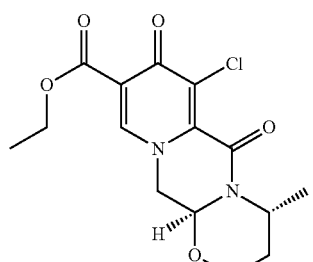

12

To a stirring solution of 11 (0.94 g, 3.0 mmol) in acetonitrile (8 mL) heated at 40° C. was added TCCA in portions during 1 h (0.44 g, 1.8 mmol). After an additional 1 h, the reaction mixture was diluted with a solution of NaHSO₃ (0.60 g) in water (60 mL), extracted with dichloromethane (50 mL) and the extract evaporated under reduced pressure to give a crude product which was purified by flash chromatography (CH$_2$Cl$_2$: MeOH, from 98:2 to 80:20) to give 12 (0.45 g, 44%).

$^1$H NMR (CDCl$_3$): δ 1.37 (t, J=7.1 Hz, 3H), 1.38 (d, J=7.0 Hz, 3H), 1.56 (dq, J=13.9, 2.2 Hz, 1H), 2.21 (m, 1H), 3.99 (d, J=2.3 Hz, 1H), 4.00 (t, J=1.8 Hz, 1H), 4.10 (dd, J=13.2, 6.6 Hz, 1H), 4.37-4.27 (m, 3H), 4.98 (m, 1H), 5.35 (dd, J=6.6, 3.8 Hz, 1H), 8.07 (s, 1H).

$^{13}$C NMR (CDCl$_3$): δ 14.20, 16.09, 29.34, 44.87, 53.73, 61.49, 62.29, 76.01, 116.22, 133.11, 134.18, 144.52, 155.48, 163.88, 169.98.

Example 17

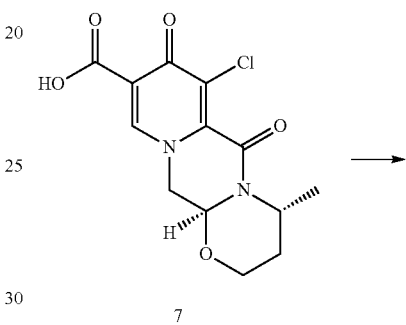

7

→

8

To a mixture of 7 (3.89 g, 12.2 mmol) in methanol (12 mL) was added sodium methylate (22.3 mL, 97.6 mmol). The reaction mixture was stirred for 24 h at 30° C. and then quenched with a slow addition of 3M hydrochloric acid (35 mL) while stirring in an ice bath. The mixture was concentrated under reduced pressure to remove most of the methanol, then extracted with dichloromethane (2×30 mL), the combined extracts washed with water (30 mL) and evaporated under reduced pressure. Methanol (20 mL) was added to the obtained amorphous residue and removed under reduced pressure to yield the solid 8 (3.69 g, 98%).

$^1$H NMR (CDCl$_3$): δ 15.04 (s, 1H), 8.42 (s, 1H), 5.29 (dd, J=5.6, 3.9 Hz, 1H), 5.01-4.96 (m, 1H), 4.42 (dd, J=13.6, 3.6 Hz, 1H), 4.25 (dd, J=13.6, 6.0 Hz, 1H), 4.05 (s, 3H), 4.00-3.97 (m, 2H), 2.21-2-14 (m, 1H), 1.53 (dd, J=14.1, 1.9 Hz, 1H), 1.36 (d, J=7 Hz, 3H). $^{13}$C NMR (CDCl$_3$): δ 176.35, 165.94, 155.03, 153.70, 143.08, 130.90, 115.94, 76.05, 62.65, 61.45, 53.86, 44.96, 29.43, 16.06.

Example 18

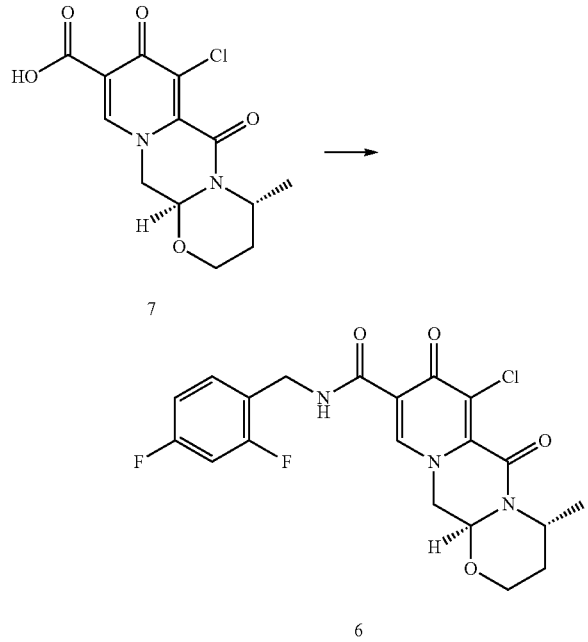

To a suspension of 7 (2.55 g, 8.0 mmol) in a mixture of triethylamine (1.46 mL, 10.4 mmol) and acetone (32 mL) stirring on an ice bath was added ethyl chloroformate (0.88 mL, 8.8 mmol). After stirring for 10 min, 2,4-difluorobenzylamine (1.07 mL, 8.8 mmol) was added and the mixture left stirring at room temperature for 1 h. The product was isolated by slowly diluting the reaction mixture with water (40 mL), filtration, washing with water (2×30 mL) and drying. There was obtained 2.91 g of 6 as a white powder (83%).

$^1$H NMR (CDCl$_3$): δ 1.30 (d, J=7.0 Hz, 3H), 1.49 (dd, J=14.0, 2.2 Hz, 1H), 2.14 (ddd, J=14.6, 11.1, 6.4 Hz, 1H), 3.89-3.95 (m, 2H), 4.09-4.15 (m, 1H), 4.26 (dd, J=13.4, 3.8 Hz, 1H), 4.55 (d, J=5.8 Hz, 2H), 4.89-4.98 (m, 1H), 5.18 (dd, J=6.2, 3.8 Hz, 1H), 6.68-6.79 (m, 2H), 7.23-7.31 (m, 1H), 8.41 (s, 1H), 10.24 (t, J=5.8 Hz, 1H). $^{13}$C NMR (CDCl$_3$): δ 16.09, 26.95, 29.30, 36.79, 45.11, 45.28, 53.86, 62.47, 75.93, 103.87 (t, J=25.4 Hz), 111.21 (dd, J=21.0, 3.4 Hz), 117.32, 130.58 (dd, J=9.3, 5.8 Hz), 133.40, 143.54, 155.34, 163.16, 163.25, 163.35, 172.88.

Example 19

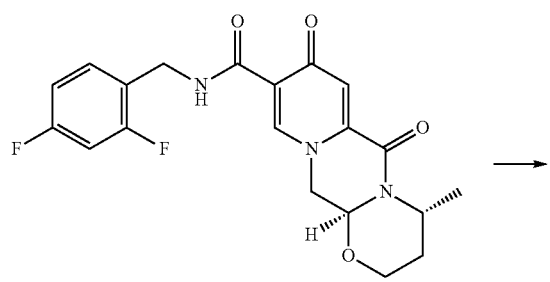

To a suspension of 5 (1.67 g, 4 mmol) in acetonitrile (20 mL) was added DABCO (23 mg, 5 mol %) and TCCA (0.62 g, 2.52 mmol). The mixture was stirred 18 h at 40° C. protected from light and then quenched with a mixture of DMSO (0.48 mL) and water (0.12 mL). The insoluble cyanuric acid was removed by filtration and washed with acetonitrile (5 mL). The filtrate was evaporated under reduced pressure to give viscous oil that was crystallized from a mixture of methanol (6 mL) and water (3 mL), by slowly cooling the solution from 60° C. to room temperature. The product 6 was filtered, washed with cold methanol (5 mL) and dried to give an off-white powder (1.07 g, 61%).

$^1$H NMR (CDCl$_3$): δ 1.30 (d, J=7.0 Hz, 3H), 1.49 (dd, J=14.0, 2.2 Hz, 1H), 2.14 (ddd, J=14.6, 11.1, 6.4 Hz, 1H), 3.89-3.95 (m, 2H), 4.09-4.15 (m, 1H), 4.26 (dd, J=13.4, 3.8 Hz, 1H), 4.55 (d, J=5.8 Hz, 2H), 4.89-4.98 (m, 1H), 5.18 (dd, J=6.2, 3.8 Hz, 1H), 6.68-6.79 (m, 2H), 7.23-7.31 (m, 1H), 8.41 (s, 1H), 10.24 (t, J=5.8 Hz, 1H). $^{13}$C NMR (CDCl$_3$): δ 16.09, 26.95, 29.30, 36.79, 45.11, 45.28, 53.86, 62.47, 75.93, 103.87 (t, J=25.4 Hz), 111.21 (dd, J=21.0, 3.4 Hz), 117.32, 130.58 (dd, J=9.3, 5.8 Hz), 133.40, 143.54, 155.34, 163.16, 163.25, 163.35, 172.88.

Example 20

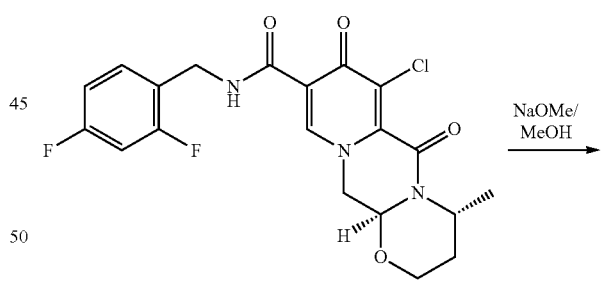

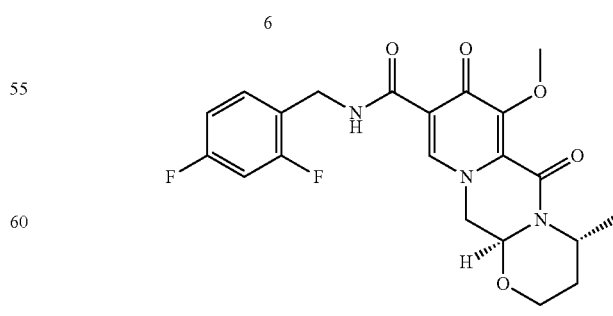

To a suspension of 6 (0.44 g) in anhydrous methanol (1 mL) was added a 25% methanolic solution of sodium methylate (1.14 mL) and the mixture stirred for 4 h at 40° C. The reaction was quenched with acetic acid (0.4 mL), diluted with water (8 mL), extracted with 2-methyltetrahydrofuran (12 mL), the extract washed with 1M NaOH(aq) (8 mL), water (8 mL) and evaporated under reduced pressure. To the oily residue was added methanol (8 mL) and evaporated under reduced pressure to give 27 as a white solid (0.38 g, 88%).

Example 21

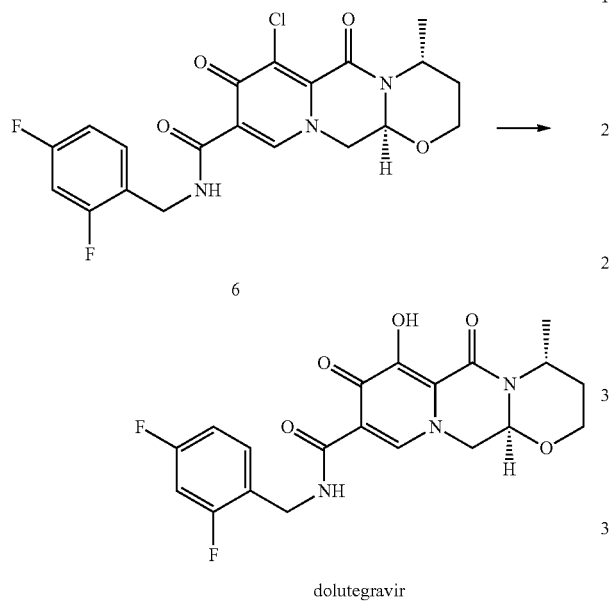

The suspension of (4R,12aS)-7-chloro-N-(2,4-difluorobenzyl)-4-methyl-6,8-dioxo-3,4,6,8,12,12a-hexahydro-2H-pyrido[1',2':4,5]pyrazino[2,1-b][1,3]oxazine-9-carboxamide (6, 0.44 g) and solid sodium hydroxide (0.20 g) in absolute ethanol (2 mL) was stirred at room temperature for 24 h. The reaction was quenched with 2M H$_2$SO$_4$ (1.18 mL) and left stirring for 2 h at room temperature. The reaction mixture was filtered through fitted funnel rinsing with water (2×2 mL). The obtained white precipitate (0.38 g) was suspended in THF-water (1:1, 4.5 mL) and stirred at room temperature for ca. 2 h. The reaction mixture was filtered through fitted funnel rinsing with water (2×1 mL) and dried in vacuo at 40° C. to afford pure dolutegravir as a white solid (0.33 g, HPLC purity: 99.38%).

$^1$H NMR (DMSO-d$_6$): δ 12.51 (s, 1H), 10.36 (t, J=5.9 Hz, 1H), 8.50 (s, 1H), 7.41-7.36 (m, 1H), 7.26-7.21 (m, 1H), 7.07-7.03 (m, 1H), 5.45 (dd, J=5.4, 4.3 Hz, 1H), 4.81-4.76 (m, 1H), 4.59-4.53 (m, 3H), 4.36 (dd, J=13.8, 5.8 Hz, 1H), 4.05-4.00 (m, 1H), 3.91-3.88 (m, 1H), 2.05-1.97 (m, 1H), 1.55-1.52 (m, 1H), 1.33 (d, J=7.1 Hz, 3H). $^{13}$C NMR (DMSO-d$_6$): δ 170.27, 163.68, 162.29, 161.78 (dd), 159.82 (dd), 154.61, 140.64, 130.74 (d), 130.67 (d), 122.37 (d), 116.73, 115.38, 111.33 (d), 103.80 (t), 62.01, 51.16, 44.69, 35.74, 29.13, 15.21.

Example 22

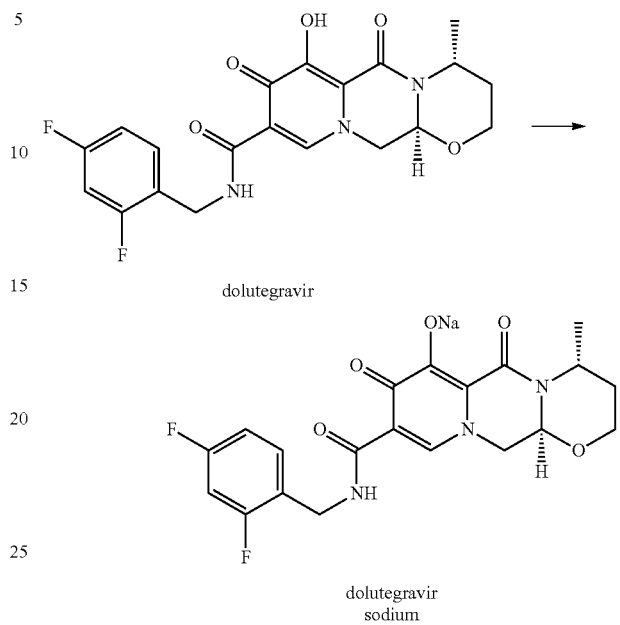

A suspension of dolutegravir (0.31 g) in methanol (4 mL) was cooled to 0° C. 25% Solution of sodium methoxide in methanol was added to the mixture and the resulting suspension was stirred at 0° C. for 2 h, then at room temperature for 23 h. The reaction mixture was then filtered through fitted funnel rinsing with methanol (3×10 mL). The white precipitate was dried overnight at room temperature to afford pure dolutegravir sodium as a white solid (0.26 g, HPLC purity: 99.84%).

$^1$H NMR (DMSO-d$_6$): δ 10.70 (t, J=5.8, 1H), 7.89 (s, 1H), 7.37-7.30 (m, 1H), 7.23-7.19 (m, 1H), 7.04-7.01 (m, 1H), 5.17 (m, 1H), 4.81 (t, J=6.4 Hz, 1H), 4.51 (d, J=5.5 Hz, 2H), 4.32-4.29 (m, 1H), 4.16 (dd, J=14.1, 4.8 Hz, 1H), 3.99-3.94 (m, 1H), 3.82-3.80 (m, 1H), 1.89-1.84 (m, 1H), 1.38 (d, J=12.9 Hz, 1H), 1.24 (d, J=7.0 Hz, 3H). $^{13}$C NMR (DMSO-d$_6$): δ 177.93, 167.12, 166.08, 161.59 (dd), 161.13, 159.63 (dd), 134.26, 130.44 (d), 130.38 (d), 122.90 (d), 114.95, 111.23 (d), 108.78, 103.64 (t), 75.59, 61.95, 53.11, 43.01, 35.32, 29.22, 15.30.

Example 23

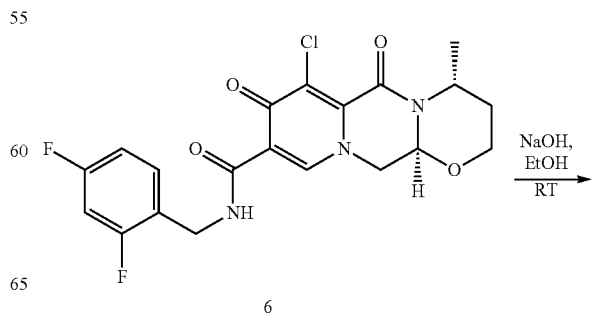

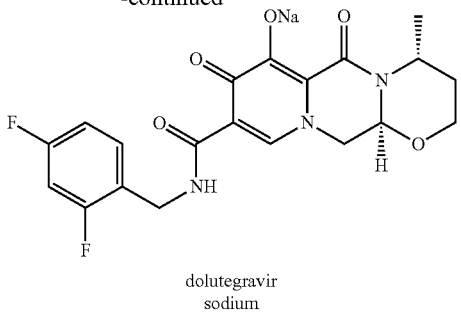

dolutegravir
sodium

The suspension of 6 (0.44 g) and solid sodium hydroxide (0.20 g) in absolute ethanol (2 mL) was stirred at room temperature for 24 h. The reaction was diluted with absolute ethanol (10 mL) and left stirring for ca. 30 min at room temperature. The reaction mixture was filtered through fitted funnel rinsing with absolute ethanol (3×10 mL) and dried in vacuo at room temperature to afford dolutegravir sodium as a pale yellow solid (0.43 g, HPLC purity: 98.80%).

$^1$H NMR (DMSO-d$_6$): δ 10.70 (t, J=5.8 Hz, 1H), 7.89 (s, 1H), 7.37-7.30 (m, 1H), 7.23-7.19 (m, 1H), 7.04-7.01 (m, 1H), 5.17 (m, 1H), 4.81 (t, J=6.4 Hz, 1H), 4.51 (d, J=5.5 Hz, 2H), 4.32-4.29 (m, 1H), 4.16 (dd, J=14.1, 4.8 Hz, 1H), 3.99-3.94 (m, 1H), 3.82-3.80 (m, 1H), 1.89-1.84 (m, 1H), 1.38 (d, J=12.9 Hz, 1H), 1.24 (d, J=7.0 Hz, 3H). $^{13}$C NMR (DMSO-d$_6$): δ 177.93, 167.12, 166.08, 161.59 (dd), 161.13, 159.63 (dd), 134.26, 130.44 (d), 130.38 (d), 122.90 (d), 114.95, 111.23 (d), 108.78, 103.64 (t), 75.59, 61.95, 53.11, 43.01, 35.32, 29.22, 15.30.

Example 24

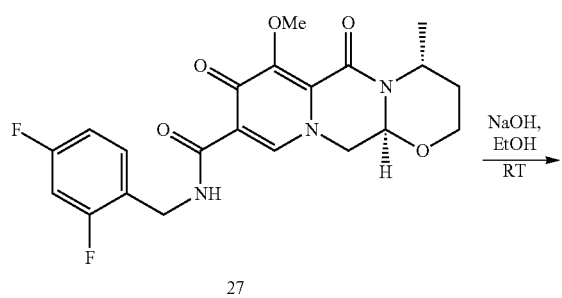

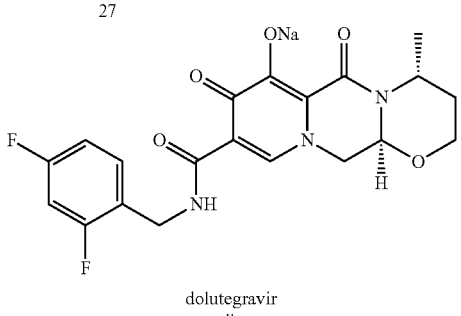

dolutegravir
sodium

The suspension of (4R,12aS)—N-(2,4-difluorobenzyl)-7-methoxy-4-methyl-6,8-dioxo-3,4,6,8,12,12a-hexahydro-2H-pyrido[1',2':4,5]pyrazino[2,1-b][1,3]oxazine-9-carboxamide (27, 0.43 g) and solid sodium hydroxide (0.20 g) in absolute ethanol (2.5 mL) was stirred at room temperature for ca. 24 h. The reaction was diluted with mixture of water/ethanol (5 mL, 1:1) and left stirring for ca. 1.5 h at room temperature. The reaction mixture was filtered through fitted funnel rinsing with mixture of water/ethanol (3×5 mL, 1:1) and dried in vacuo at room temperature to afford 15 as a pale yellow solid (0.41 g, HPLC purity: 98.87%).

$^1$H NMR (DMSO-d$_6$): δ 10.70 (t, J=5.8 Hz, 1H), 7.89 (s, 1H), 7.37-7.30 (m, 1H), 7.23-7.19 (m, 1H), 7.04-7.01 (m, 1H), 5.17 (m, 1H), 4.81 (t, J=6.4 Hz, 1H), 4.51 (d, J=5.5 Hz, 2H), 4.32-4.29 (m, 1H), 4.16 (dd, J=14.1, 4.8 Hz, 1H), 3.99-3.94 (m, 1H), 3.82-3.80 (m, 1H), 1.89-1.84 (m, 1H), 1.38 (d, J=12.9 Hz, 1H), 1.24 (d, J=7.0 Hz, 3H). $^{13}$C NMR (DMSO-d$_6$): δ 177.93, 167.12, 166.08, 161.59 (dd), 161.13, 159.63 (dd), 134.26, 130.44 (d), 130.38 (d), 122.90 (d), 114.95, 111.23 (d), 108.78, 103.64 (t), 75.59, 61.95, 53.11, 43.01, 35.32, 29.22, 15.30.

Example 25

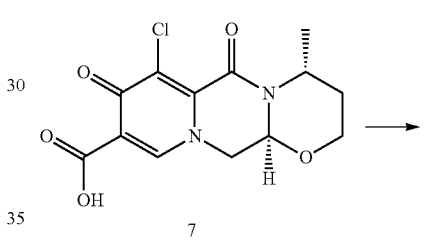

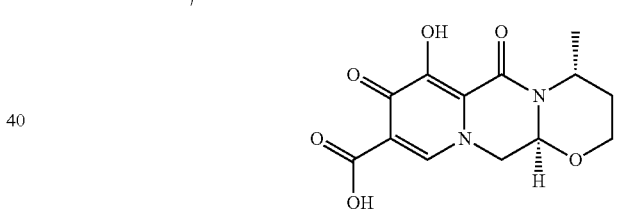

The suspension of (4R,12aS)-7-chloro-4-methyl-6,8-dioxo-3,4,6,8,12,12a-hexahydro-2H-pyrido[1',2':4,5]pyrazino[2,1-b][1,3]oxazine-9-carboxylic acid (7, 0.31 g) and solid sodium hydroxide (0.20 g) in absolute ethanol (2.5 mL) was stirred at 50° C. for 3 days. The reaction was quenched with 2M H$_2$SO$_4$ (1.2 mL) and left stirring for 7 h at room temperature. The reaction mixture was filtered through fitted funnel rinsing with water (3×5 mL) and ethanol (5 mL) dried in vacuo at 40° C. to afford 28 as a pale yellow solid (0.17 g).

$^1$H NMR (DMSO-d$_6$): δ 15.37 (s, 1H), 12.76 (s, 1H), 8.66 (s, 1H), 5.51-5.49 (m, 1H), 4.80-4.78 (m, 1H), 4.65 (dd, J=13.8, 3.7 Hz, 1H), 4.43 (dd, J=13.8, 5.9 Hz, 1H), 4.05 (t, J=11.5 Hz, 1H), 3.91 (dd, J=11.4, 3.1 Hz, 1H), 2.07-2.00 (m, 1H), 1.56 (d, J=13.8 Hz, 1H), 1.34 (d, J=7.0 Hz, 3H). $^{13}$C NMR (DMSO-d$_6$): δ 172.21, 165.39, 161.73, 153.61, 141.11, 118.66, 112.99, 75.95, 62.03, 51.50, 44.90, 29.08, 15.18.

Example 26

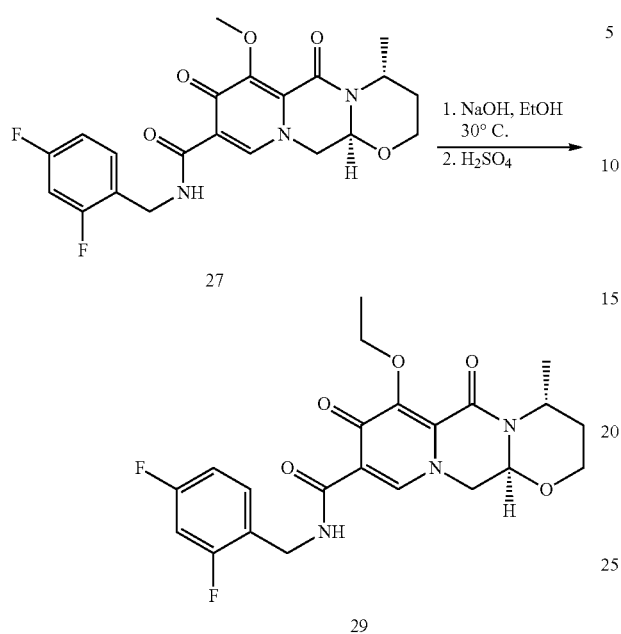

The suspension of (4R,12aS)—N-(2,4-difluorobenzyl)-7-methoxy-4-methyl-6,8-dioxo-3,4,6,8,12,12a-hexahydro-2H-pyrido[1',2':4,5]pyrazino[2,1-b][1,3]oxazine-9-carboxamide (27, 0.88 g) and solid sodium hydroxide (0.24 g) in absolute ethanol (20 mL) was stirred at 30° C. for 1.5 h. The reaction was quenched with 2M $H_2SO_4$ (1.5 mL) and left stirring for 3 hours at room temperature. The reaction mixture was filtered through fritted funnel and rinsed with water (3×2 mL) and ethanol (4 mL), and dried in vacuo at 40° C. to afford O-ethyl dolutegravir (29) as a pale yellow solid (0.25 g). The filtrate was extracted with ethyl acetate (3×5 mL). The combined organic layers were dried over $MgSO_4$, filtered and concentrated, then dried in vacuo at 40° C. to afford more 29 as a pale yellow solid (0.27 g).

$^1$H NMR ($CDCl_3$): δ 10.37 (t, J=5.8 Hz, 1H), 8.36 (s, 1H), 7.37-7.32 (m, 1H), 6.83-6.77 (m, 2H), 5.19 (dd, J=5.9, 3.8 Hz, 1H), 5.04-4.98 (m, 1H), 4.61 (d, J=6 Hz, 2H), 4.26-4.22 (m, 3H), 4.11 (dd, J=13.4, 5.9 Hz, 1H), 3.97 (t, J=2.4 Hz, 1H), 3.96 (d, J=2.4 Hz, 1H), 2.21-2.14 (m, 1H), 1.51 (dq, J=14.0, 2.3 Hz, 1H), 1.47 (t, J=7.0 Hz, 3H), 1.35 (d, J=7.1 Hz, 3H).

$^{13}$C NMR ($CDCl_3$): δ 174.78, 164.17, 162.49 (dd), 160.51 (dd), 155.72, 154.08, 142.32, 130.60 (dd), 129.33, 121.51 (dd), 118.67, 111.23 (dd), 103.78 (t), 76.15, 69.74, 62.58, 53.42, 44.58, 36.50 (d), 29.44, 16.04, 15.64.

Example 27

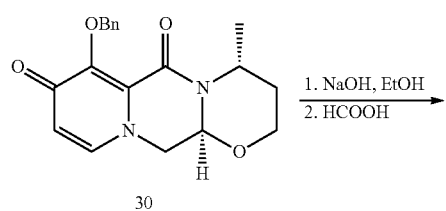

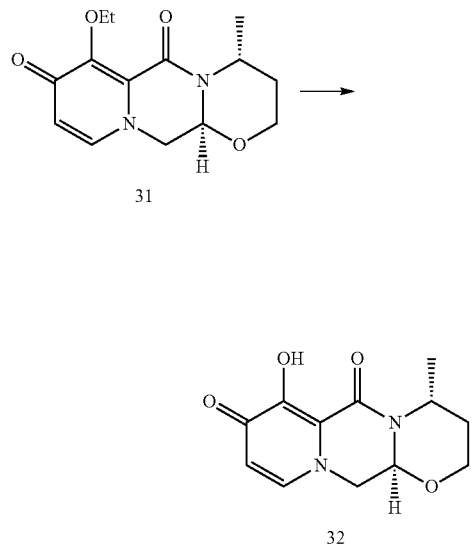

The suspension of (4R,12aS)-7-(benzyloxy)-4-methyl-3,4,12,12a-tetrahydro-2H-pyrido[1',2':4,5]pyrazino[2,1-b][1,3]oxazine-6,8-dione (30, 0.68 g, prepared according to prior art) and solid sodium hydroxide (0.40 g) in absolute ethanol (5 mL) was stirred at 50° C. for 14 h. The reaction was quenched with formic acid (0.35 mL), water (2 mL) was added and mixture was left stirring for additional 1 h at room temperature. The reaction mixture was extracted with ethyl acetate (3×5 mL) and the combined organic layers concentrated to afford a crude oil. Purification by flash chromatography (eluting with $CH_2Cl_2$/methanol) afforded 32 as an orange solid (0.26 g, 52%).

The above procedure if done at room temperature in same time period, affords 31 as orange oil (0.24 g, 43%).

Compound 32: $^1$H NMR (DMSO-$d_6$): δ 7.64 (d, J=7.4 Hz, 1H), 6.20 (d, J=7.3 Hz, 1H), 5.40 (dd, J=5.1, 4.2 Hz, 1H), 4.83-4.78 (m, 1H), 4.35 (dd, J=13.6, 3.9 Hz, 1H), 4.13 (dd, J=13.6, 5.4 Hz, 1H), 4.05-4.00 (m, 1H), 3.90-3.85 (m, 1H), 2.03-1.95 (m, 1H), 1.52 (dd, J=13.9, 1.9 Hz, 1H), 1.33 (d, J=7.1 Hz, 3H). $^{13}$C NMR (DMSO-$d_6$): δ 170.96, 163.01, 153.48, 137.96, 116.83, 113.52, 76.18, 62.05, 50.39, 44.53, 29.21, 15.28.

Compound 31: $^1$H NMR (DMSO-$d_6$): δ 7.67 (d, J=7.4 Hz, 1H), 6.28 (d, J=7.4 Hz, 1H), 5.29 (dd, J=5.4, 3.8 Hz, 1H), 4.82-4.75 (m, 1H), 4.32 (dd, J=13.6, 3.6 Hz, 1H), 4.10 (dd, J=13.5, 5.6 Hz, 1H), 4.03-3.93 (m, 3H), 3.85 (ddd, J=11.6, 5.0, 2.2 Hz, 1H), 1.97-1.89 (m, 1H), 1.48 (dd, J=13.8, 2.1 Hz, 1H), 1.27 (d, J=7.1 Hz, 3H), 1.26 (d, J=7.0 Hz, 3H). $^{13}$C NMR (DMSO-$d_6$): δ 174.38, 156.11, 150.82, 139.48, 116.39, 113.52, 75.92, 67.31, 61.80, 51.36, 44.22, 29.29, 15.76, 15.36.

Example 28

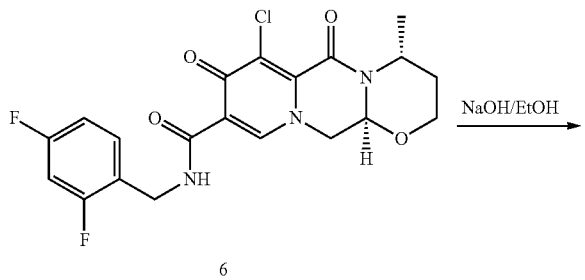

The transformation of 6 to dolutegravir with sodium hydroxide in ethanol was monitored for the interconversion of intermediates. The suspension of 6 (0.44 g) and solid sodium hydroxide (0.20 g) in ethanol (3.33 mL) was stirred at 22° C. Samples of the reaction mixture were taken after 3, 8 and 24 h for UPLC analysis. After 24 h, the reaction mixture was quenched with 2 M $H_2SO_4$ (5 mL), and left stirring at room temperature. The reaction mixture was filtered through fritted funnel, the product rinsed with water (30 mL) and dried in vacuo at 50° C. overnight to afford dolutegravir as a white solid (0.27 g, 64%).

The results of reaction monitoring:

| Entry | Time (h) | UPLC analysis (area %) | | |
|---|---|---|---|---|
| | | compound 6 | compound 29 | dolutegravir |
| 1 | 3 h | 37.50 | 20.63 | 39.99 |
| 2 | 8 h | 0.78 | 15.46 | 80.32 |
| 3 | 24 h | 0.31 | 8.56 | 88.21 |

Example 29

The effect of added water and reaction temperature was evaluated by monitoring 4 reactions in parallel. To the suspensions of 27 (0.86 g) in MeOH were added solid sodium hydroxide (0.40 g) or aqueous solution of NaOH (5 M, 2 mL) (see Table below). The reactions were stirred in parallel at 50° C. or 22° C. Samples were taken in timely intervals for UPLC analysis.

The results of reaction monitoring demethylation of 27 in MeOH:

| Entry | NaOH (5 eq) | MeOH (mL) | T (° C.) | UPLC analysis (area % of dolutegravir) | | | | | |
|---|---|---|---|---|---|---|---|---|---|
| | | | | 1 h | 2 h | 3 h | 5 h | 7 h | 24 h |
| 1 | solid | 5 | 50 | 48.21 | 58.81 | 73.89 | 84.17 | 89.10 | 94.59 |
| 2 | 5M aq. | 3 | 50 | 22.84 | 24.89 | 47.65 | 61.72 | 77.08 | 92.67 |
| 3 | solid | 5 | 22 | 6.74 | 9.32 | 12.60 | 16.95 | 22.79 | 47.16 |
| 4 | 5M aq. | 3 | 22 | 0.56 | 0.63 | 1.70 | 1.24 | 2.39 | 5.04 |

Example 30

Example 31

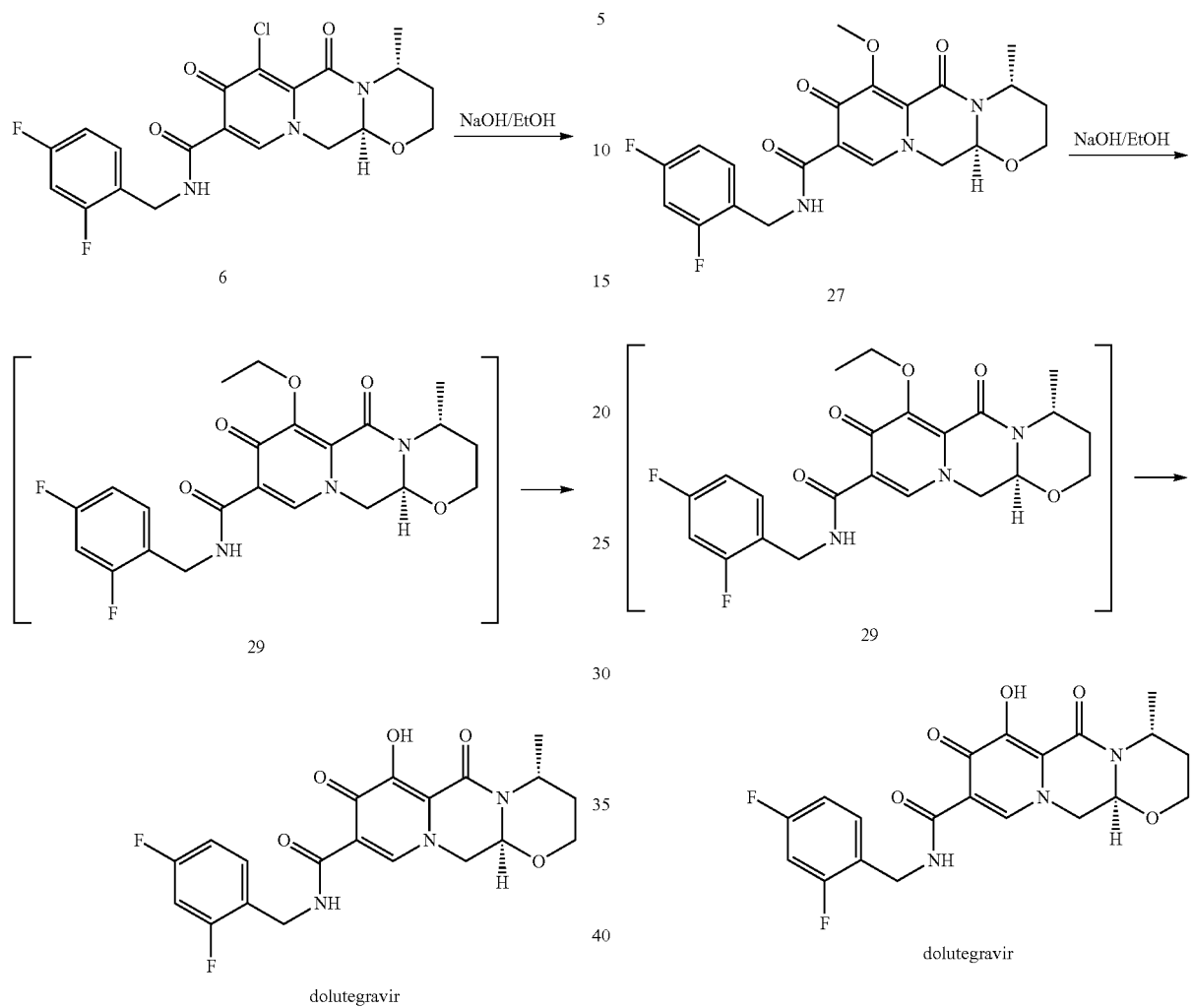

dolutegravir

The effect of added water and reaction temperature was evaluated by monitoring 4 reactions in parallel. To the suspensions of 6 (0.88 g) in EtOH were added solid sodium hydroxide (0.40 g) or aqueous solution of NaOH (5 M, 2 mL) (see Table below). The reactions were stirred in parallel at 50° C. or 22° C. Samples were taken in timely intervals for UPLC analysis. The results of reaction monitoring of the transformations of 6 in ethanol with NaOH:

The effect of added water and reaction temperature was evaluated by monitoring 4 reactions in parallel. To the suspensions of 27 (0.88 g) in EtOH were added solid sodium hydroxide (0.40 g) or aqueous solution of NaOH (5 M, 2 mL) (see Table below). The reactions were stirred in parallel at 50° C. or 22° C. Samples were taken in timely intervals for UPLC analysis.

The results of reaction monitoring of the transformations of 27 in ethanol with NaOH:

|  |  |  |  | UPLC analysis (area %) | | | | | | | | |
|---|---|---|---|---|---|---|---|---|---|---|---|---|
|  |  |  | 1 h | | 2 h | | 3 h | | 5 h | | 7 h | |
| Entry | NaOH (5 eq) | EtOH (mL) | T (° C.) | 29 | dol. | 29 | dol. | 29 | dol. | 29 | dol. | 29 | dol. |
| 1 | solid | 5 | 50 | 3.87 | 84.66 | 2.04 | 88.00 | 1.74 | 88.90 | 1.63 | 89.42 | 1.66 | 89.25 |
| 2 | 5M aq. | 3 | 50 | 1.49 | 19.51 | 1.82 | 35.65 | 3.24 | 48.30 | 4.11 | 68.23 | 3.57 | 73.64 |
| 3 | solid | 5 | 22 | 0 | 2.73 | 4.78 | 10.92 | 5.04 | 17.97 | 6.35 | 40.32 | 5.67 | 44.38 |
| 4 | 5M aq. | 3 | 22 | 0 | 0.89 | 1.63 | 1.90 | 0.17 | 3.30 | 0.28 | 5.84 | 0.32 | 7.76 | dol. = dolutegravir

| | | | UPLC analysis (area %) | | | | | | | |
|---|---|---|---|---|---|---|---|---|---|---|
| | NaOH | EtOH | T | 1 h | | 2 h | | 3 h | | 5 h | | 7 h | |
| Entry | (5 eq) | (mL) | (° C.) | 29 | dol. | 29 | dol. | 29 | dol. | 29 | dol. | 29 | dol. |
| 1 | solid | 5 | 50 | 1.58 | 95.70 | 1.40 | 95.88 | 1.25 | 96.26 | 1.00 | 96.31 | 1.53 | 94.88 |
| 2 | 5M aq. | 3 | 50 | 69.29 | 26.41 | 50.59 | 45.82 | 36.36 | 59.24 | 20.20 | 73.61 | 10.48 | 83.50 |
| 3 | solid | 5 | 22 | 77.91 | 14.10 | 78.94 | 16.46 | 74.58 | 21.02 | 60.32 | 35.92 | 53.36 | 43.16 |
| 4 | 5M aq. | 3 | 22 | 33.39 | 2.22 | 60.52 | 4.29 | 68.84 | 4.97 | 73.4 | 5.66 | 76.26 | 7.42 | dol. = dolutegravir

Example 32

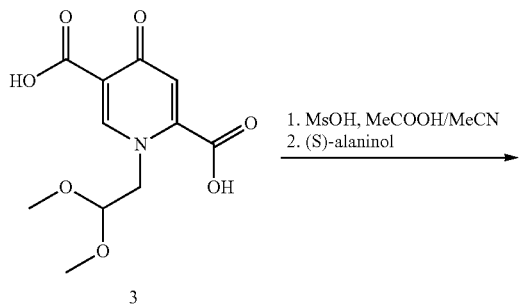

Example 33

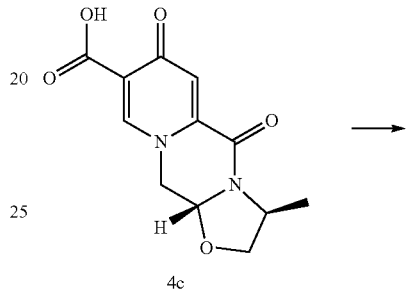

Compound 3 (30 g, 110 mmol; assay 99%) was suspended in acetonitrile (450 mL), acetic acid (73 mL) and methanesulfonic acid (25 mL) were added. The reaction mixture was stirred 4 h at 70° C. The clear red solution was cooled to 25° C. Triethylamine (77 mL) and (S)-2-aminopropanol (17 mL) were added and the mixture was stirred at reflux temperature for 20 h. The reaction mixture was cooled to 25° C. and the insoluble product filtered, washed with 1M HCl(aq) (60 mL), water (3×60 mL) and dried to give 4c (19.49 g, 67%): mp=313-315° C.;

$^1$H NMR (DMSO-d$_6$): δ 1.31 (d, J=6.3 Hz, 3H), 3.65 (dd, J=8.6, 6.8 Hz, 1H), 4.13 (dd, J=11.7, 10.3 Hz, 1H), 4.28 (m, 1H), 4.39 (dd, J=8.6, 6.8 Hz, 1H), 4.92 (dd, J=12.3, 4.2 Hz, 1H), 5.45 (dd, J=10.2, 4.1 Hz, 1H), 7.16 (s, 1H), 8.84 (s, 1H), 15.74 (s, 1H); $^{13}$C NMR (DMSO-d$_6$) 16.5, 51.6, 52.9, 72.4, 81.6, 115.8, 118.1, 141.5, 147.6, 153.4, 165.3, 179.0.

Compound 4c (2.78 g) was suspended in dimethylformamide (40 mL), cooled to 0° C., then triethylamine (3.52 mL) was added, followed by ethyl chloroformate (1.31 mL). After 10 min there was added 2,4-difluorobenzylamine (1.57 mL). The mixture was then stirred at 25° C. for 1 h. Water (150 mL) was added and the mixture extracted with dichloromethane (50 mL). The organic phase was separated, washed with water (2×50 mL), dried over sodium sulfate and evaporated under reduced pressure. The residue (4.31 g) was treated with boiling 2-propanol (40 mL), the suspension cooled, the product filtered and dried to give the product 5c as a white powder (2.70 g, 69%): 99.80 area % by HPLC at 258 nm; mp=222-223° C.; MS (ESI) m/z=390 [MH]$^+$; $^1$H NMR (DMSO-d$_6$): δ 1.30 (d, J=6.3 Hz, 3H), 3.63 (dd, J=8.6, 6.8 Hz, 1H), 4.02 (m, 1H), 4.26 (m, 1H), 4.37 (dd, J=8.6, 6.8 Hz, 1H), 4.53 (d, J=6.0 Hz, 2H), 4.84 (dd, J=12.2, 4.2 Hz, 1H), 5.40 (dd, J=12.2, 4.2 Hz, 1H), 6.91 (s, 1H), 7.05 (m, 1H), 7.24 (m, 1H), 7.38 (m, 1H), 8.62 (s, 1H), 10.43 (t, J=6.0 Hz, 1H).

Example 34

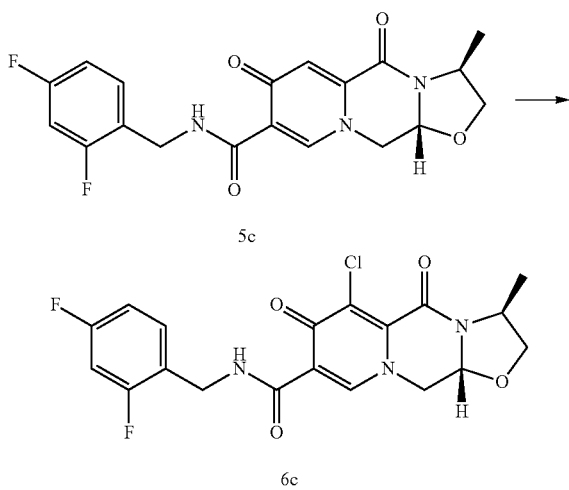

To a suspension of 5c (2.70 g, 6.9 mmol) in acetonitrile (32 mL) was added DABCO (39 mg, 5 mol %) and TCCA (1.01 g, 4.3 mmol). The mixture was stirred 20 h at 40° C. protected from light and then quenched with a mixture of DMSO (0.81 mL) and water (0.20 mL). The insoluble cyanuric acid was removed by filtration and washed with acetonitrile (10 mL). The filtrate was evaporated under reduced pressure to give viscous oil that was crystallized from a mixture of methanol (10 mL) and water (5 mL), by slowly cooling the solution from 60° C. to room temperature. The product 6c was filtered, washed with cold methanol (8 mL) and dried to give an off-white powder (1.20 g, 41%): mp=225-227° C.; MS (ESI) m/z=424 [MH]$^+$; $^1$H NMR (DMSO-d$_6$): δ 1.28 (d, J=6.3 Hz, 3H), 3.65 (dd, J=8.6, 6.9 Hz, 1H), 4.09 (m, 1H), 4.26 (m, 1H), 4.35 (dd, J=8.6, 6.6 Hz, 1H), 4.54 (d, J=5.9 Hz, 2H), 4.85 (dd, J=12.3, 3.8 Hz, 1H), 5.42 (dd, J=10.1, 3.8 Hz, 1H), 7.06 (m, 1H), 7.24 (m, 1H), 7.40 (m, 1H), 8.67 (s, 1H), 10.24 (t, J=6.0 Hz, 1H).

Example 35

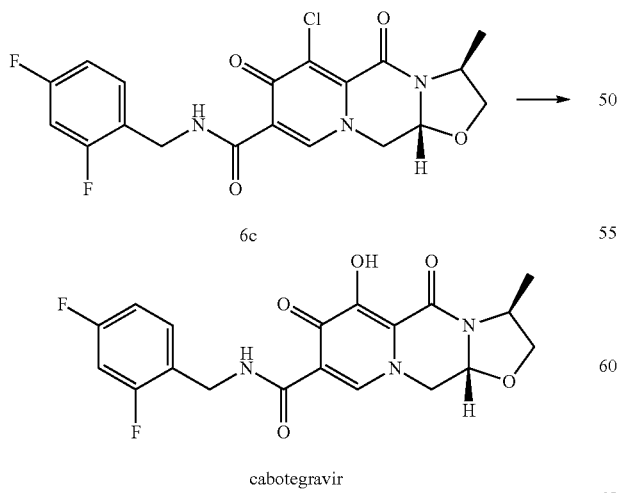

The suspension of 6c (1.00 g, 2.4 mmol) and sodium hydroxide (0.57 g, 14.2 mmol) in absolute ethanol (7 mL) was stirred at 40° C. for 16 h. The reaction was quenched with 0.5M H$_2$SO$_4$ (15 mL), extracted with dichloromethane (20 mL), the extract washed with water (20 mL) and evaporated under reduced pressure. The residue was triturated in MTBE (10 mL), the product filtered, washed with MTBE (10 mL) and dried to give cabotegravir as an off-white solid (0.74 g, 77%): MS (ESI) m/z=405 [MH]$^+$.

The invention claimed is:

1. A process for preparing a compound of formula (I) or a salt thereof

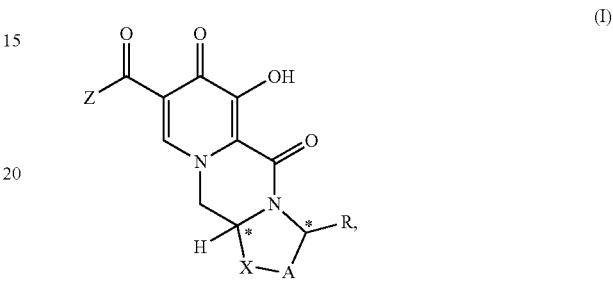

wherein
A represents CH$_2$ or CH$_2$—CH$_2$,
R represents H, C$_1$-C$_4$ alkyl or unsubstituted or substituted phenyl,
X represents O, S, or N—R$^5$, wherein R$^5$ is H or C$_1$-C$_4$ alkyl,
Z represents hydroxy, C$_1$-C$_4$ alkoxy, phenoxy, benzoxy, —NH—Ar or —NH—CH$_2$—Ar,
wherein Ar represents unsubstituted or substituted phenyl, and
* represents a chirality center, which is of (R) or (S) configuration,
the process comprising the steps of
(a) providing a compound of formula (II) or a salt thereof,

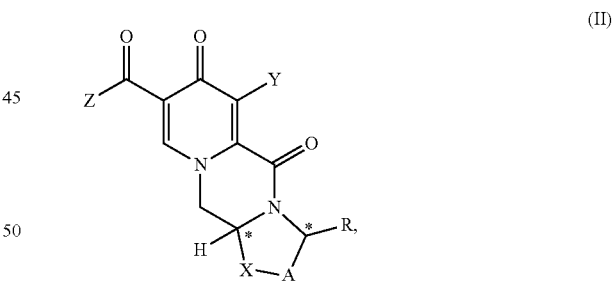

wherein A, R, X, Z, and * have the same meaning as above and
Y represents Cl or O—R$_a$,
wherein R$_a$ represents C$_1$-C$_4$ alkyl or benzyl,
and
(b) carrying out a chemical transformation to obtain the compound of formula (I) and/or a salt thereof,
wherein the transformation is carried out in the presence of a hydroxide and methanol and/or ethanol.

2. The process according to claim 1, wherein hydroxide is alkali hydroxide.

3. The process according to claim 1, wherein the compound of formula (I) is a compound of formula (Ia) or a salt thereof

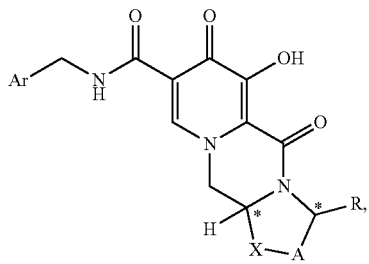

(Ia)

and wherein the compound of formula (II) is a compound of formula (IIa) or a salt thereof

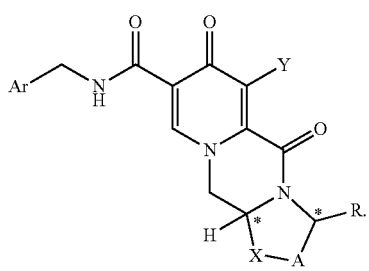

(IIa)

4. The process according to claim 1, wherein Y is Cl.

5. The process according to claim 4, wherein the compound of formula (II) is provided by carrying out a chlorination reaction on a compound of formula (III) or a salt thereof.

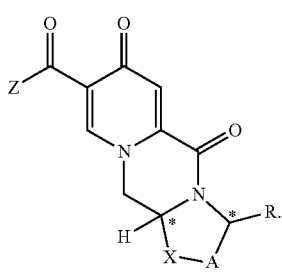

(III)

6. The process according to claim 4, wherein the compound of formula (II) is provided by carrying out a chlorination reaction on a compound of formula (V) or a salt thereof.

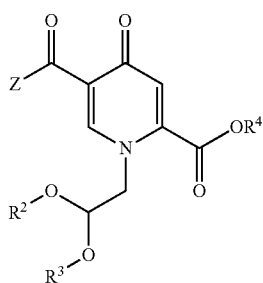

(V)

to obtain a compound of formula (IV) or a salt thereof

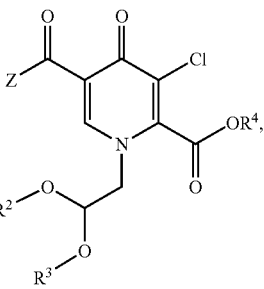

(IV)

and by subsequently transforming the compound of formula (IV) or a salt thereof to the compound of formula (II) or a salt thereof, wherein $R^2$ and $R^3$ independently represent H, $C_1$-$C_4$ alkyl or benzyl or are fused to represent a $C_2$-$C_4$ alkylene chain, and $R^4$ represents H or $C_1$-$C_4$ alkyl.

7. The process according to claim 5, wherein chlorination is carried out by a chlorinating agent selected from a compound of formula (CA1)

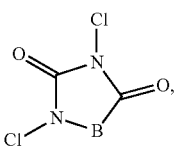

(CA1)

wherein B represents —CO—NH—, —CO—NCl—, or —$CR^6R^7$—, wherein $R^6$ and $R^7$ independently represent $C_1$-$C_4$ alkyl or phenyl, in the presence of a solvent.

8. The process according claim 1, wherein dolutegravir or a pharmaceutically acceptable salt or solvate thereof or cabotegravir or a pharmaceutically acceptable salt or solvate thereof is prepared.

9. A process for preparing dolutegravir or a pharmaceutically acceptable salt or a solvate thereof, the process comprising the steps of:

(i) providing a compound of formula (5) or a salt thereof

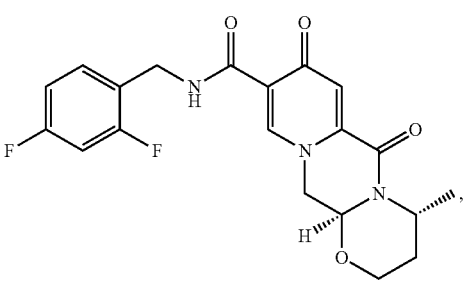

5

(ii) converting the compound of formula (5) or a salt thereof to a compound of formula (6) or a salt thereof

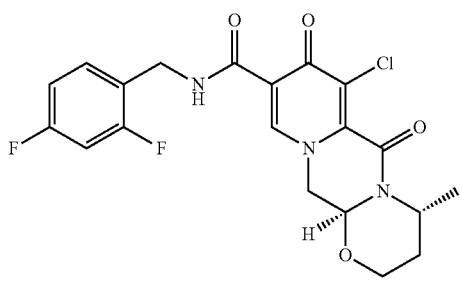

6 by carrying out a chlorination reaction, and (iii) converting the compound of formula (6) or a salt thereof to dolutegravir and/or a pharmaceutically acceptable salt or a solvate thereof, wherein the transformation is carried out in the presence of a hydroxide, optionally in the presence of methanol and/or ethanol.

10. A process for preparing cabotegravir or a pharmaceutically acceptable salt or a solvate thereof, the process comprising the steps of:

(i) providing a compound of formula (5c) or a salt thereof

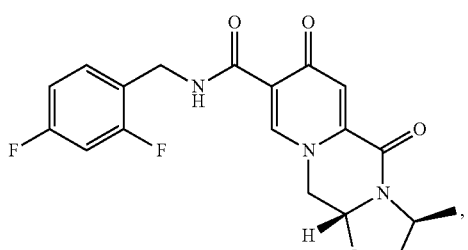

5c (ii) converting the compound of formula (5c) or a salt thereof to a compound of formula (6c) or a salt thereof

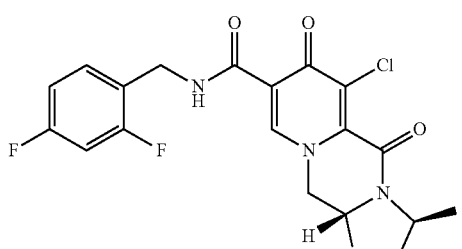

6c by carrying out a chlorination reaction, and (iii) converting the compound of formula (6c) or a salt thereof to cabotegravir and/or a pharmaceutically acceptable salt or a solvate thereof, wherein the transformation is carried out in the presence of a hydroxide, optionally in the presence of methanol and/or ethanol.

11. The process according to claim 9, wherein the compound of formula (5) is provided by converting a compound of formula (3)

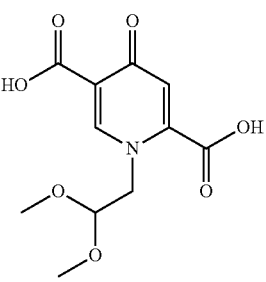

3 to a compound of formula (4)

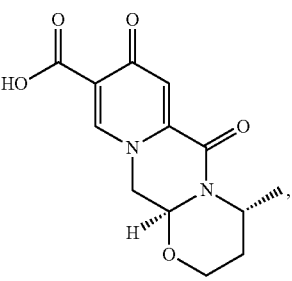

4 wherein the conversion comprises cyclocondensation with (R)-3-aminobutanol, and by subsequently converting the compound of formula (4) to the compound of formula (5) by amidation with 2,4-difluorobenzylamine.

12. The process according to claim 10, wherein the compound of formula (5c) is provided by converting a compound of formula (3)

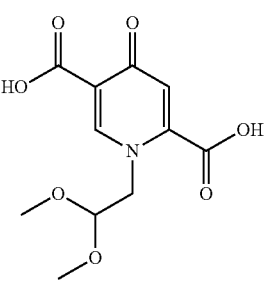

3 to a compound of formula (4c)

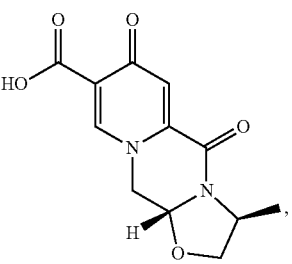

4c wherein the conversion comprises cyclocondensation with (S)-alaninol, and by subsequently converting the compound of formula (4c) to the compound of formula (5c) by amidation with 2,4-difluorobenzylamine.

13. The process according to claim 11, wherein the compound of formula (3) is prepared by converting a compound of formula (1)

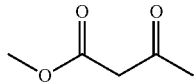

1 with N,N-dimethylformamide dimethyl acetal (DMFDMA) followed by substitution with aminoacetaldehyde dimethyl acetal to obtain a compound of formula (2)

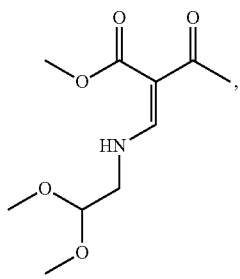

2 and by subsequently converting the compound of formula (2) through a cyclocondensation with dimethyl oxalate in the presence of sodium methylate to obtain the compound of formula (3).

14. A process for the preparation of a compound of formula (II) or a salt thereof

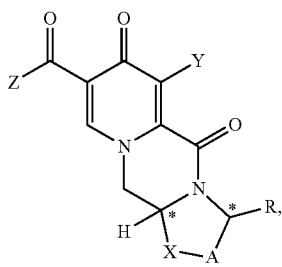

(II)

wherein

A represents $CH_2$ or $CH_2$—$CH_2$,

R represents H, $C_1$-$C_4$ alkyl or unsubstituted or substituted phenyl,

X represents O, S, or N—$R^5$, wherein $R^5$ is H or $C_1$-$C_4$ alkyl,

Z represents hydroxy, $C_1$-$C_4$ alkoxy, phenoxy, benzoxy, —NH—Ar or —NH—$CH_2$—Ar, wherein Ar represents unsubstituted or substituted phenyl,

* represents a chirality center, which is of (R) or (S) configuration, and Y represents Cl, wherein the compound of formula (II) or a salt thereof is prepared by carrying out a chlorination reaction on a compound of formula (III)

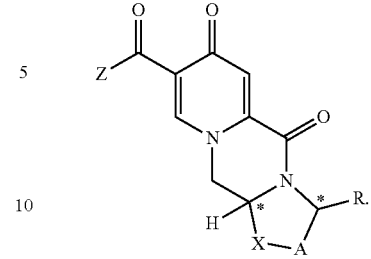

(III)

15. A process for the preparation of a compound of formula (IV) or a salt thereof,

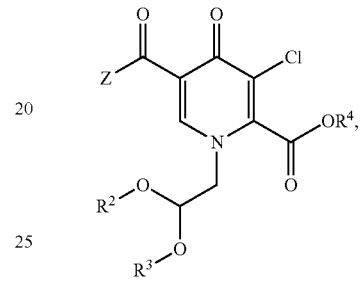

(IV)

wherein $R^2$ and $R^3$ independently represent H, $C_1$-$C_4$ alkyl or benzyl or are fused to represent a $C_2$-$C_4$ alkylene chain, $R^4$ represents H or $C_1$-$C_4$ alkyl, and Z represents hydroxy, $C_1$-$C_4$ alkoxy, phenoxy, benzoxy, —NH—Ar or —NH—$CH_2$—Ar, wherein Ar represents unsubstituted or substituted phenyl, and wherein the compound of formula (IV) or a salt thereof is prepared by carrying out a chlorination reaction on a compound of formula (V)

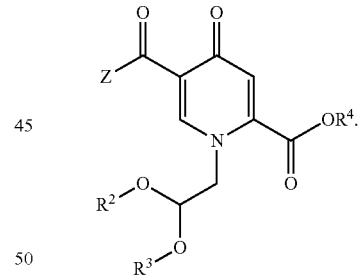

(V)

16. A compound selected from a compound of formula (IIa-1) or a salt thereof

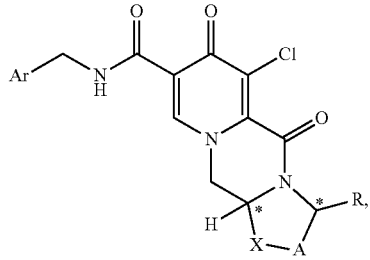

(IIa-1)

wherein A, R, X, Ar and * are defined as set forth in claim 1, and a compound of formula (6) or a salt thereof
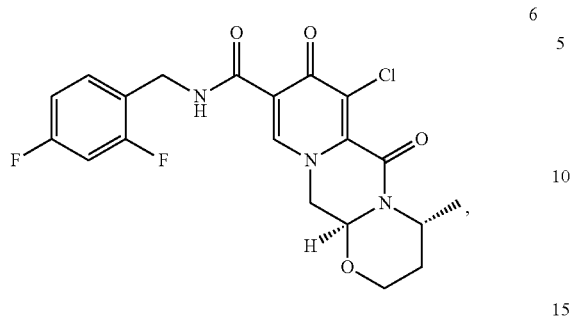
6
and a compound of formula (6c) or a salt thereof
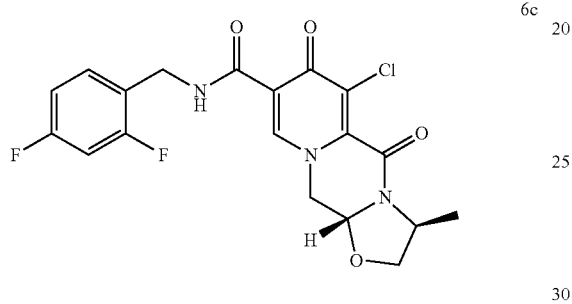
6c
* * * * *